(12) United States Patent
Hiatt et al.

(10) Patent No.: US 6,808,709 B1
(45) Date of Patent: Oct. 26, 2004

(54) IMMUNOGLOBULINS CONTAINING PROTECTION PROTEINS AND THEIR USE

(75) Inventors: Andrew C. Hiatt, San Diego, CA (US); Julian K.-C. Ma, London (GB); Thomas Lehner, Herts (GB); Keith E. Mostov, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 143 days.

(21) Appl. No.: 09/717,888

(22) Filed: Nov. 20, 2000

Related U.S. Application Data

(63) Continuation of application No. 09/312,157, filed on May 14, 1999, now Pat. No. 6,303,341, which is a continuation of application No. 08/434,000, filed on May 4, 1995, now Pat. No. 6,046,037, which is a continuation-in-part of application No. 08/367,395, filed on Dec. 30, 1994, now abandoned.

(51) Int. Cl.$^7$ .............................................. A61K 39/395
(52) U.S. Cl. .................................. 424/130.1; 424/147.1
(58) Field of Search .......................... 424/130.1, 147.1, 424/204.1; 435/69.1, 70.21; 536/23.5, 23.53

(56) References Cited

U.S. PATENT DOCUMENTS

| | | |
|---|---|---|
| 4,594,244 A | 6/1986 | Lehner et al. |
| 4,607,388 A | 8/1986 | Koiyumaki et al. |
| 4,652,448 A | 3/1987 | Sadowski |
| 4,736,866 A | 4/1988 | Leder et al. |
| 4,870,009 A | 9/1989 | Evans et al. |
| 4,873,191 A | 10/1989 | Wagner et al. |
| 5,034,322 A | 7/1991 | Rogers et al. |
| 5,183,756 A | 2/1993 | Schlom |
| 5,188,642 A | 2/1993 | Shah et al. |
| 5,202,422 A * | 4/1993 | Hiatt et al. ............... 530/387.3 |
| 5,349,124 A | 9/1994 | Fischloff et al. |
| 5,352,440 A | 10/1994 | Gilchrest et al. |
| 5,352,446 A | 10/1994 | Lehner |
| 5,352,605 A | 10/1994 | Fraley et al. |
| 5,854,402 A * | 12/1998 | Lehner et al. ............ 530/388.4 |

FOREIGN PATENT DOCUMENTS

| | | |
|---|---|---|
| EP | 484 148 A1 | 5/1992 |
| EP | 0 371 017 B1 | 9/1994 |
| EP | 480014 B1 | 11/1996 |
| WO | 87/00551 | 1/1987 |
| WO | WO 88/06455 * | 9/1988 |
| WO | 90/14430 | 11/1990 |
| WO | 91/06320 | 5/1991 |
| WO | 91/16061 | 10/1991 |

OTHER PUBLICATIONS

Huang, Ann L. et al., "Glucocorticoid Regulation of the Ha–MuSV p21 Gene Conferred by Sequences from Mouse Mammary Tumor Virus," Cell, 27:245–255 (1981).

Odell, Joan T. et al., "Identification of DNA sequences required for activity of the cauliflower mosaic virus 35S promoter," Nature, 313:810–812 (1985).

Ma, J. K–C. et al., "Assembly of monoclonal antibodies with IgG1 and IgA heavy chain domains in transgenic tobacco plants," Eur. J. Immunol. 24:131–138 (1994).

Neuhaus, G. et al., "Transgenic rapeseed plants obtained by the microinjection of DNA into microspore–derived embryoids," Theor. Appl. Genet., 75:30–36 (1987).

Abdullah, Ruslan et al., "Efficient Plant Regeneration from Rice Protoplasts Through Somatic Embryogenesis," Biotechnology, 4:1087–1090 (1986).

Bakos et al. Expression and purification of biologically active domain 1 of the human polymeric immunoglobulin receptor. Molecular Immunology. vol. 31, No. 2, pp. 165–168, May 1994.

Banting, George et al., "Intracellular targetting signals of polymeric immunoglobulin receptors are highly conserved between species," FEBS Letters, 254:177–183 (1989).

Barnes, Wayne M., "Variable patterns of expression of luciferase in transgenic tobacco leaves," Proc. Natl. Acad. Sci. USA, 87:9183–9187 (1990).

Benbrook, Charles M. et al., "Herbicide Resistance: Environmental and Economic Issues," in Proceedings Bio Expo 1986, Butterworth, Stoneham, MA, pp. 27–54 (1986).

Benfey, Philip N. et al., "Regulated Genes in Transgenic Plants," Science, 244:174–181 (1989). Mostov, Keith E. et al., "The receptor for transepithelial transport of IgA and IgM contains multiple immunoglobulin–like domains," Nature, 308:37–43 (1984).

Benfey, Philip N. et al., "The Cauliflower Mosaic Virus 35S Promoter: Combinatorial Regulation of Transcription in Plants," Science, 250:959–966 (1990).

Brandtzaeg, P. & Prydz, H., "Direct evidence for an integrated function of J chain and secretory component in epithelial transport of immunoglobulins," Nature, 311:71–73 (1984).

(List continued on next page.)

*Primary Examiner*—Ali R. Salimi
(74) *Attorney, Agent, or Firm*—Morrison & Foerster LLP

(57) ABSTRACT

The immunoglobulins of the present invention are useful therapeutic immunoglobulins against mucosal pathogens such as *S. mutans*. The immunoglobulins contain a protection protein that protects the immunoglobulins in the mucosal environment. The invention also includes the greatly improved method of producing immunoglobulins in plants by producing the protection protein in the same cell as the other components of the immunoglobulins. The components of the immunoglobulin are assembled at a much improved efficiency. The method of the invention allows the assembly and high efficiency production of such complex molecules. The invention also contemplates he production of immunoglobulins containing protection proteins in a variety of cells, including plant cells, that can be selected for useful additional properties. The use of immunoglobulins containing protection proteins a therapeutic antibodies against mucosal and other pathogens is also contemplated.

3 Claims, 1 Drawing Sheet

OTHER PUBLICATIONS

Bytebier, Benny et al., "T–DNA organization in tumor cultures and transgenic plants of the monocotyledon Asparagus officinalis," Proc. Natl. Acad. Sci. USA, 84:5345–5349 (1987).

Callis, Judy et al., "Introns increase gene expression in cultured maize cells," Genes and Development, 1:1183–1200 (1987).

Carayannopoulos, L. et al., "Recombinant human IgA expressed in insect cells," Proc. Natl. Acad. Sci. U.S.A., 91:8348–8352 (1994).

Corthesy, B. et al., "Biochemical Characterisation of Recombinant Secretory component," Experientai, 50:A27, Abstract S08–08 (1994).

Crago et al., "Antisera to the secretory component recognize the murine Fc receptor for IgA," Journal of Immunology 142(11):3909–3912 (1989).

de la Pena, A. et al., "Transgenic rye plants obtained by injecting DNA into young floral tillers," Nature, 325:274–276 (1987).

During et al. Synthesis and self–assembly of a functional monoclonal antibody in transgenic Nicotiana tabacum. Plant Molecular Biology 15: 281–293, 1990.

During et al., "Synthesis and self–assembly of a functional monoclonal antibody in transgenic Nicotiana tabacum," Plant Molecular Biology 15:281–293 (1990).

During, "Wundinduzierbare expression und sekretion von T4 lysozym and monoklonalen antikorpern in Nicotiana tabacum," Inaugral Dissertation (1988).

Eliasson et al., "Chimeric IgG–binding receptors engineered from staphylococcal protein A and streptococcal protein G," Journal of Biological Chemistry 263(9):4323–4327 (1989).

Fraley, Robert T. et al., "Expression of bacterial genes in plant cells," Proc. Natl. Acad. Sci. U.S.A., 80:4803–4807 (1983).

Fromm, Michael E. et al., "Stable transformation of maize after gene transfer by electroporation," Nature, 319:791–793 (1986).

Hein, Mich B. et al., "Evaluation of Immunoglobulins from Plant Cells," Biotechnol. Prog., 7:455–461 (1991).

Hess, Dieter, "Pollen–Based Techniques in Genetic Manipulation," International Review of Cytology, 107:367–395 (1987).

Hiatt et al., "Characterization and Applications of Antibodies Produced in Plants," Intern. Rev. Immunol. 10: 139–152 (1993).

Hiatt, A. and M. Hein, "Structure, Function and Uses of Anitbodies from Transgenic Plants and Animals," The Pharmacology of Monoclonal Antibodies, Chapter 12, pp. 317–330, M. Rosenberg and G.P. Moore eds., Springer–Verlag, Berlin (1994).

Hiatt, A. et al., "Monoclonal antibody engineering in plants," FEBS Letters, 307(1):71–75 (1992).

Hiatt, Andrew, "Production of antibodies in transgenic plants," Nature, 342:76–78 (1989).

Horsch, R. B. et al., "A Simple and General Method for Transferring Genes into Plants," Science, 227:1229–1231 (1985).

Huse, William D. et al., "Generation of a Large Combinatorial Library of the Immunboglobulin Repertoire in Phage Lambda," Science, 246:1275–1281 (1989).

Jorgensen, Richard et al., "T–DNA is organized predominantly in inverted repeat structures in plants transformed with Agrobacterium tumefaciens C58 derivatives," Mol. Gen. Genet., 207:471–477 (1987).

Klein, T. M. et al., "High–velocity microprojectiles from delivering nucleic acids into living cells," Nature, 327:70–73 (1987).

Klein, Theodore M. et al., "Stable genetic transformation of intact Nicotiana cells by the particle bombardment process," Proc. Natl. Acad. Sci. U.S.A., 85:8502–8505 (1988).

Kobayashi, Kunihiko et al., "Studies on human secretory IgA (II). Comparative studies on a fragment of secretory component derived from secretory IgA and fragments obtained by enzymatic digestion of free secretory component," Immunochemistry, 10:73–80 (1973).

Koshland, Marian Elliot, "The Immunoglobulin Helper: The J Chain." Immunoglobulin Genes, Chap. 18, pp. 345–359, Academic Press (Honjo, Alt and Rabbits, Eds. 1989).

Kraehenbuhl, Jean–Pierre et al., "Transepithelial transport and mucosal defence II: secretion of IgA," Trends in Cell Biol., 2:170–174 (1992).

Kraehenbul et al, "Receptor–mediated transepithelial transport of secretory antibodies and engineering of mucosal antibodies," Advances in Experimental Medicine and Biology 216B:1053–1060 (1987).

Krajci, Peter et al., "Molecular cloning and exon–intron mapping of the gene encoding human transmembrane secretory component (the poly–Ig receptor)," Eur. J. Immunol., 22:2309–2315 (1992).

Krajci, Peter et al., "Molecular cloning of the human transmembrane secretory component (poly–Ig receptor) and its mRNA expression in human tissues," Biochem. Biophys. Res. Comm., 158:783–789 (1989).

Larrick, J. W. and R. Balint, "Recombinant Therapeutic Human Monoclonal Antibodies," The Pharmacology of Monoclonal Antibodies, Chapter 2, pp. 23–48, M. Rosenberg and G.P. Moore eds., Springer–Verlag, Berlin (1994).

Lee, C. K. et al., "Oral Administration of Polymeric Immunoglobulin A Prevents Colonization with Vibrio cholerae in Neonatal Mice," Infection and Immunity, 62(3):887–891 (1994).

Lindh, E., "Increased Resistance of Immunoglobulin A Dimers to Proteolytic Degradation After Binding of Secretory Component," The Journal of Immunology, 114(1):284–286 (1975).

Lorz, Horst et al., "Gene transfer to cereal cells mediated by protoplast transformation," Mol. Gen. Genet., 199:178–182 (1985).

Luo, Zhong–xun et al., "A Simple Method for the Transformation of Rice Via the Pollen–Tube Pathway," Plant Mol. Biol. Reporter, 6:165 (1988).

Ma, J. K.–C. et al., "Generation and Assembly of Secretory Antibodies in Plants," Science, 268:716–719 (1995).

Ma, J. K–C. et al., "Specificity of monoclonal antibodies in local passive immunization against Streptococcus mutans," Clin. Exp. Immunol. 77:331–337 (1989).

Marcotte, Jr., William R. et al., "Regulation of a wheat promoter by abscisic acid in rice protoplasts," Nature, 335:454–457 (1988).

Mark, G. E. and E. A. Padlan, "Humanization of Monoclonal Antibodies," The Pharmacology of Monoclonal Antibodies, Chapter 4, pp. 105–134, M. Rosenberg and G.P. Moore eds., Springer–Verlag, Berlin (1994).

Marshall, R. D., "Glycoproteins," Annual Review of Biochemistry, 41:673–702, Annual Reviews Inc. (Snell, Boyer, Meister, and Sinsheimer, Eds. 1972).

Marshall, R. D., "The Nature and Metabolism of the Carbohydrate–Peptide Linkages of Glycoproteins," Biochem. Soc. Symp., 40:17–26 (1974).

Matsuuchi, Linda et al., "Immunoglobulin J chain gene from the mouse," Proc. Natl. Acad. Sci. U.S.A., 83:456–460 (1986).

McCabe, Dennis E. et al., "Stable transformation of soybean (glycine max) by particle acceleration," Biotechnology, 6:923–926 (1988).

McNabb, Paul C. et al., "Host Defense Mechanisms at Mucosal Surfaces," Ann. Rev. Microbiol., 35:477–496 (1981).

Mostov, Keith A., "Transepithelial transport of immunoglobulins," Ann. Rev. Immol., 12:63–84 (1994).

Orlandi, Rosaria et al., "Cloning immunoglobulin variable domains for expression by the polymerase chain reaction," Proc. Natl. Acad. Sci. U.S.A., 86:3833–3837 (1989).

Paszkowski, Jerzy et al., "Direct gene transfer to plants," The EMBO Journal, 3:2717–2722 (1989).

Piskurich, J. F. et al., "Molecular Cloning of Mouse Polymeric Ig Receptor cDNA," J. Immunol., 150:38, Abstract 203 (1993).

Potrykus, Ingo et al., "Direct gene transfer to cells of a graminaceous monocot," Mol. Gen. Genet., 199:183–188 (1985).

Rogers, S. G. et al., "Improved Vectors for Plant Transformation: Expression Cassette Vectors and New Selectable Markers," Methods in Enzymology, 153:253–277 (1987).

Cocking and Davey, "Gene Transfer in Cereals," Science, 236:1259–1262 (1987).

Silbart, Lawrence K. et al., "Reduction of Intestinal Carcinogen Absorption by Carcinogen–Specific Secretory Immunity," Science, 243:1462–1464 (1989).

Smith, Roberta and T. Lehner, "Characterisation of monoclonal antibodies to common protein epitopes on the cell surface of Streptococcus mutans and Streptocuccus sobrinus," Oral Microbiol. Immunol., 4:153–158 (1989).

Solari et al., "Cellular location of the cleavage event of the polymeric immunoglobulin receptor and fate of its anchoring domain in the rat hepatocyte," Biochemical Journal 257:759–768 (1989).

Spielmann, Albert et al., "T–DNA structure in transgenic tobacco plants with multiple independent integration sites," Mol. Gen. Genet., 205:34–41 (1986).

Toriyama, Kinya et al., "Haploid and diploid plant regeneration from protoplasts of anther callus in rice," Theor. Appl. Genet., 73:16–19 (1986).

Uchimiya, Hirofumi et al., "Expression of a foreign gene in callus derived from DNA–treated protoplasts of rice (Oryza sativa L.)," Mol. Gen. Genet., 204:204–207 (1986).

Vasil. Indra K., "Progress in the regeneration and genetic manipulation of cereal crops," Biotechnology, 6:397–402 (1988).

Verbeet et al., GenBank Accession No. X81371.

Williams, Alan F. et al., "The Immunoglobulin Superfamily" Immunoglobulin Genes, Chap. 19, pp. 361–387, Academic Press (Honjo, Alt and Rabbits, Eds. 1989).

Zhou, Guang–Yu et al., "Introduction of Exogenous DNA into Cotton Embryos," Methods in Enzymology, 101:433–481 (1983).

\* cited by examiner

SYNTHETIC OLIGONUCLEOTIDE:

31 ACC<u>AGATCT</u>ATGGAATGGACCTGGGTTTTTC
32 CCC<u>AAGCTT</u>GGTTTTGGAGATGGTTTTCTC
33 GAT<u>AAGCTT</u>GGTCCTACTCCTCCTCCTA
34 AAT<u>CTCGAG</u>TCAGTAGCAGATGCCATCTCC
35 GGA<u>AAGCTT</u>TGTACATATGCAAGGCTTACA

AMPLIFICATION BY PCR:

RECOMBINANT HEAVY CHAINS:

PLANT G13

PLANT G1/A

PLANT G2/A

IMMUNOGLOBULINS CONTAINING PROTECTION PROTEINS AND THEIR USE

CROSS REFERENCE TO RELATED APPLICATIONS

This a continuation of application Ser. No. 09/312,157, filed May 14, 1999, now U.S. Pat. No. 6,303,341, which is a continuation of application Ser. No. 08/434,000, filed May 4, 1995, now U.S. Pat. No. 6,046,037, which is a continuation-in-part of application Ser. No. 08/367,395 filed Dec. 30, 1994, now abandoned, each of which is hereby incorporated by reference in its entirety including drawings.

FIELD OF INVENTION

The present invention relates to expression of immunoglobulins in plants that contain a protection protein as well as to transgenic plants that express such immunoglobulins. The therapeutic use of these immunoglobulins is also contemplated.

BACKGROUND TO THE INVENTION

Monoclonal antibodies have great potential for numerous therapeutic purposes. The advantages of monoclonal antibody therapeutics over conventional pharmaceuticals include their exquisite selectivity, multiple effector functions, and ease of molecular manipulation such as radioisotope labelling and other types of conjugation. A wide variety of target antigens have been used to generate specific monoclonal antibodies. See for example *Therapeutic Monoclonal Antibodies,* C. A. K. Borrebaeck and J. W. Larrick eds., Stockton Press, New York, 1990, and *The Pharmacology of Monoclonal Antibodies,* M. Rosenberg and G. P. Moore eds., Springer-Verlag, Berlin, 1994.

One therapeutic application of monoclonal antibodies is passive immunotherapy in which the exogenously produced immunoglobulins are administered directly to the animal being treated by injection or by ingestion. To be successful, passive immunotherapy must deliver an appropriate amount of an immunoglobulin to the animal, because passive immunotherapy does not rely on an immune response in the animal being treated. The immunoglobulins administered must be specific for the pathogen or molecule desired to effect treatment. One advantage of passive immunotherapy is the speed at which the antibody can be contacted with the target compared to a normal immune response. Passive immunotherapy can also be used as a prophylaxis to prevent the onset of diseases or infections.

A major potential use of passive immunotherapy is in combating bacterial infections. Recent emergence of antibiotic resistant bacteria make treatment of bacterial infections with passive immunotherapy desirable. Antibiotic treatment targeted to a single pathogen often involves eradication of a large population of normal microbes, and this can have undesired side effects. An alternative approach has been to utilize the inherent specificity of immunoglobulins to inhibit a specific pathogenic function in very specific microbial populations. In this strategy, purified immunoglobulins of the appropriate specificity would be administered in order to provide a passive barrier to pathogen invasion.

In addition, the immunoglobulins used for passive immunotherapies for example, for oral administration of immunoglobulins must meet certain requirements. First, the immunoglobulin must be functional in very harsh environments, such as the gastrointestinal tract. Second, the immunoglobulin must be resistant to the actions of proteases so that it will not be degraded prior to inactivating the target.

Certain types of cells, including epithelial cells and hepatocytes, are capable of assembling immunoglobulin molecules which have been specifically adapted to function in harsh environments. These immunoglobulins are referred to as secretory immunoglobulins (SIg) and include both secretory IgA (SIgA) and secretory IgM (SIgM). The protection provided by endogenous secretory immunoglobulins have been demonstrated. Several mechanisms for protection from bacterial infection by secretory immunoglobulins have been proposed, including, but not limited to, direct killing, agglutination, inhibition of epithelial attachment and invasion, inactivation of enzymes and toxins, opsonization, and complement activation. In an animal, endogenously produced SIgA are exposed to very harsh environments where numerous proteases, such as intestinal and bacterial enzymes are extremely active and denaturants, such as stomach acid, are also present.

One component of secretory immunoglobulins, the secretory component, helps to protect the immunoglobulin against these inactivating agents thereby increasing the biological effectiveness of secretory immunoglobulin.

The mechanism of synthesis and assembly of these secretory immunoglobulins, such as SIgA or SIgM is extremely complex. In animal cells, secretory immunoglobulins are assembled in a process involving different cells types. Each secretory immunoglobulin is made up of immunoglobulin heavy and light chains, joining chain (J chain) and a secretory component. The immunoglobulin producing B cells make and assemble the immunoglobulin heavy and light chain together with J chain to produce dimeric or polymeric IgM or IgA. The secretory component is produced by a second type of cell, either epithelial cells or hepatocytes, and secretory immunoglobulin is assembled in and secreted from these cells. The mechanism by which these cells assemble and secrete the secretory immunoglobulin is extremely complex and requires a unique microenvironment provided, for example, by mucosal tissues. The microenvironment places the B cells that produce the polymeric immunoglobulin near the cells that assemble and secrete secretory immunoglobulin onto the mucosal surface of an animal.

The epithelial cells have a receptor, the polyimmunoglobulin receptor (pIgR), that specifically recognizes and binds polymeric immunoglobulin/containing J chain, internalizing it and transporting it through the epithelial cell. Expressed on the basolateral cell surface, the pIgR has an N-terminal signal peptide of 18 amino acids, an extracellular polyimmunoglobulin binding portion of 629 amino acids, a membrane spanning segment of 23 hydrophobic residues, and a cytoplasmic tail of 103 amino acids. The extra-cellular portion contains five immunoglobulin-like domains of 100–111 amino acids each and constitutes the secreted form of the molecule. See for example, Mostov, *Ann. Rev. Immol.,* 12:63–84 (1994) The site at which the polyimmunoglobulin receptor is cleaved to generate mature secretory component has not been accurately determined.

The polyimmunoglobulin receptor is located on the basolateral surface of epithelial cells in animals. Polymeric, J chain-containing immunoglobulins produced in B cells interact with and are bound by the receptor resulting in vesicularization, transport across the epithelial cell, and ultimate secretion to the mucosal surface. Transepithelial transport also involves proteolysis and phosphorylation to produce the mature SIg containing the secretory component. The close association of the required cells found in the mucosal microenvironment, specifically the B lymphocytes and epithelial cells, is required for secretory immunoglobulin assembly.

The targeting of the production of immunoglobulins in transgenic organisms, such as mice, is extremely difficult and transgenic organisms made from fungus or plants do not contain the proper cell types and mucosal microenvironment to produce secretory immunoglobulins. The production of large amounts of secretory immunoglobulins in transgenic organisms and cell culture has, before this invention, been impossible. One desiring to produce a secretory immunoglobulin in cell culture or a transgenic organism must express the immunoglobulin heavy chain, the immunoglobulin light chain, and J chain in a B lymphocyte. To mimic the proper mucosal microenvironment a cell having the pIgR receptor on its surface would also have to be present and be in close association with that B lymphocyte to even attempt to assemble a functional secretory immunoglobulin.

This elaborate process required for natural secretory immunoglobulin assembly is extremely difficult to duplicate in cell culture or transgenic organisms. Production of SIg in cell culture or transgenic organisms would require coupling the functions of cells producing immunoglobulin with the functions of epithelial cells in artificial (in vitro) systems. Moreover, if the desired transgenic organism is a fungus, a bacterium, or a plant, the cell types and pathways of receptor-mediated cellular internalization, transcytosis, and secretion simply are not present. Those organisms lack epithelial cells and the required mucosal microenvironment.

To date only the assembly of immunoglobulins having light, heavy and J chain within the same cell has been reported. See Carayannopoulos et al. *Proc. Nat Acad. Sci., U.S.A.,* 91:8348–8352 (1994). However, the assembly of an immunoglobulin having the additional protein component, secretory component, within a single cell has not been described.

The present invention discloses a novel method for the assembly of these complex molecules. Rather than assemble the tetrameric complex at the epithelial cell surface by the interaction of a membrane bound polyimmunoglobulin receptor with immunoglobulin, we have assembled secretory immunoglobulin composed of alpha, J, and kappa immunoglobulin chains associated with a protection protein derived from pIgR. This invention produces transgenic plants that assemble secretory immunoglobulins with great efficiency. The present invention makes passive immunotherapy economically feasible.

SUMMARY OF THE INVENTION

The present invention contemplates a new type of immunoglobulin molecule. Immunoglobulins of the present invention contain a protection protein in association with an immunoglobulin derived heavy chain having at least a portion of an antigen binding domain. In other embodiments, the immunoglobulin of the present invention further comprise an immunoglobulin derived light chain having at least a portion of an antigen binding domain associated with the immunoglobulin derived heavy chain.

The protection proteins of the present invention give the immunoglobulins containing these protein useful properties including resistance to chemical and enzymatic degradation and resistance to denaturation. These protection proteins enhanced the resistance of the immunoglobulins to environmental conditions.

The protection proteins of the proteins of the present invention comprise at least a segment of amino acid residues 1 to 606 of native polyimmunoglobulin receptor (pIgR) of any species. Other useful protection proteins include protection proteins that contain portions of the pIgR molecule. For example, the protection protein may comprise all or part of: amino acids 1–118 (domain I of rabbit pIgR), amino acids 1 to 223 (domains I and II of rabbit pIgR); amino acids 1 to 332 (domains I, II, III of rabbit pIgR); amino acids 1 to 441 (domains I, II, III, and IV rabbit of pIgR); amino acids 1 to 552 (domains I, II, III, IV and V of rabbit pIgR); and amino acids 1 to 606 or 1 to 627 of pIgR. Additional amino acids, derived either from the pIgR sequence 653–755, or from other sources, may be included so long as they do not constitute a functional transmembrane spanning segment.

In other preferred embodiments, the immunoglobulins of the present invention have a protection protein which has a first amino acid sequence which substantially corresponds to at least a portion of the amino acid residues 1 to 606 or 1 to 627 of the rabbit polyimmunoglobulin receptor and has a second amino acid residue sequence contiguous with said first amino acid sequence, wherein said second amino acid residue sequence does not have an amino acid residue sequence corresponding to the transmembrane segment of the rabbit polyimmunoglobulin receptor.

In more preferred embodiments, the second amino acid residue sequence has at least a portion of an amino acid sequence which corresponds to amino acid residues 655 to 755 of a polyimmunoglobulin receptor. In other preferred embodiments, the second amino acid residue is at least a portion of one or more of the following: an intracellular domain of a polyimmunoglobulin molecule, a domain of a member of the immunoglobulin gene superfamily, an enzyme, a toxin, or a linker.

The present invention contemplates protection proteins which do not have an amino acid residue corresponding to the transmembrane segment of rabbit polyimmunoglobulin receptor but may have amino acid residues corresponding to the intracellular domain of the rabbit polyimmunoglobulin receptor and this are deletion mutants of the receptor.

The present invention also contemplates immunoglobulins containing protection proteins which have an amino acid sequence which does not contain amino acid residues of a polyimmunoglobulin receptor from a species which are analogous to amino acid residues 288 to 755 of the rabbit immunoglobulin receptor, but does contain at least a portion of the amino acid residues or the domains from a polyimmunoglobulin receptor of a species which are analogous to one or more of these amino acid segments: Amino acids corresponding to amino acid residues 20–45 of the rabbit polyimmunoglobulin receptor; amino acids corresponding to or analogous to amino acid residues 1 to 120 of the rabbit polyimmunoglobulin receptor: amino acids corresponding to or analogous to amino acid residues numbers 120–230 of the rabbit immunoglobulin receptor; amino acids corresponding to or analogous to amino acid residues numbers 230–340 of the rabbit polyimmunoglobulin receptor; amino acids corresponding to or analogous to amino acid residues 340–456 of the rabbit polyimmunoglobulin receptor; amino acids corresponding to or analogous to amino acid residues numbers 450–550 to 570 of the rabbit polyimmunoglobulin receptors; amino acids corresponding to or analogous to amino acid residues 550 to 570–606 to 627 of the rabbit polyimmunoglobulin receptor.

The protection proteins of the present invention may be derived from many species and include protection proteins derived from mammals, rodents, humans, bovine, porcine, ovine, fowl, caprine, mouse, rat, guinea pig, chicken or other bird and rabbit.

In preferred embodiments, the immunoglobulins of the present invention contain two or four immunoglobulin derived heavy chains having at least a portion of an antigen binding domain associated with the protection protein and two or four immunoglobulin derived light chains having at least a portion of an antigen binding domain bound to the each of the immunoglobulin derived heavy chains.

In other preferred embodiments, the immunoglobulins of the present invention further comprise immunoglobulin J chain bound to at least one of the immunoglobulin derived heavy chains. In preferred embodiments, the component parts of the immunoglobulins of the present invention are bound together by hydrogen bonds, disulfide bonds, covalent bonds, ionic interactions or combinations of said bonds. In other preferred embodiments, the immunoglobulin of the present invention contain protection proteins and/or immunoglobulin derived heavy, light or J chains that are free from N-linked and/or O-linked oligosaccharides.

The immunoglobulins of the present invention may be used as therapeutic immunoglobulins against, for example, mucosal pathogen antigens. In preferred embodiments, the immunoglobulins of the present invention are capable of preventing dental caries by binding to an antigen from *S. mutans* serotypes c, e and f; and *S. sobrinus* stereotype d and g, using older nomenclature *S. mutans* a, c, d, e, f, g and h.

The present invention also contemplates a eukaryotic cell, including a plant cell, containing an immunoglobulin of the present invention. Eukaryotic cells, including plant cells, containing a nucleotide sequence encoding a protection protein and a nucleotide sequence encoding an immunoglobulin derived heavy chain having at least a portion of an antigen binding domain is also contemplated. Eukaryotic cells, including plant cells, that additionally contain a nucleotide sequence encoding an immunoglobulin derived light chain having at least a portion of an antigen binding domain is also contemplated. In preferred embodiments, the eukaryotic cells, including plant cells, of the present invention contain nucleotide sequences that encode immunoglobulins that have an antigen binding domain is capable of binding an antigen from *S. mutans* serotypes a, c, d, e, f, and g, h (*S. mutans* serotypes c, e and f and *S. sobrinus* serotypes d and g under new nomenclature. The nucleotide sequences include RNA and appropriate DNA molecules arranged for expression.

In preferred embodiments, the plant cells of the present invention are part of a plant such as a whole plant. The present invention contemplates the use of all types of plants, both dicotyledonous and monocotyledonous including alfalfa, and tobacco.

The present invention also contemplates compositions comprising an immunoglobulin of the present invention and plant macromolecules derived from one of the plants useful in practicing the present invention. Particularly contemplated are compositions containing ribulose bisphosphate carboxylase, light harvesting complex, pigments, secondary metabolites or chlorophyll and an immunoglobulin of the present invention. Preferred compositions have an immunoglobulin concentration of between 0.001% and 99.9% mass excluding water. In more preferred embodiments, the immunoglobulin concentrations present in the composition is between 0.1% and 99%. Other preferred compositions have plant macromolecules present in a concentration of between 1% and 99% mass excluding water.

The present invention also contemplates methods for making an immunoglobulin of the present invention comprising introducing into a plant cell an expression vector having a nucleotide sequence encoding a protection protein operably linked to a transcriptional promoter; and introducing into the same plant cell an expression vector containing a nucleotide sequence encoding an immunoglobulin derived heavy chain having at least a portion of an antigen binding domain, operably linked to a transcriptional promoter. Other methods that further include the step of introducing into the same plant cell an expression vector containing a nucleotide sequence encoding an immunoglobulin derived light chain having at least a portion of an antigen binding domain, operably linked to a transcriptional promoter. Other preferred methods include also introducing into a plant cell an expression vector containing a nucleotide sequence encoding an immunoglobulin J chain operably linked to a transcriptional promoter.

The present invention also contemplates methods for producing assembled immunoglobulins having heavy, light and J chains and a protection protein by introducing into a eukaryotic cell nucleotide sequences operatively linked for expression to encode an immunoglobulin derived heavy chain having at least a portion of an antigen binding domain, an immunoglobulin light chain having at least a portion of an antigen binding domain, and immunoglobulin J chain, and a protection protein. The method further comprises maintaining the eukaryotic cell under conditions allowing the production and assembly of the immunoglobulin derived heavy and light chains together with the immunoglobulin J chain and the protection protein to form an immunoglobulin containing a protection protein.

The present invention also contemplates methods of making an immunoglobulin resistant to various environmental conditions (more stable) and harsh conditions by operatively linking a nucleotide sequence encoding at least a portion of a desirable antigen binding domain derived from an immunoglobulin heavy chain to a nucleotide sequence encoding at least one domain derived from an immunoglobulin $\mu$ or $\alpha$ (IgM or IgA) heavy chain (or other immunoglobulin having increased stability in the environment) to form a nucleotide sequence encoding a chimeric immunoglobulin heavy chain and expressing that nucleotide sequence in a eukaryotic which also contains at least one molecule from the following list: a protection protein, an immunoglobulin derived light chain having at least a portion of an antigen binding domain and an immunoglobulin J chain. The method further comprises allowing the chimeric immunoglobulin heavy chain to assemble with the other molecule present in the same cell to form an immunoglobulin which is resistant to environmental conditions and more stable.

The large scale production of immunoglobulins of the present invention is contemplated by growing the plants of the present invention and extracting the immunoglobulins from those plants. In preferred embodiments, the method of producing therapeutic immunoglobulin compositions containing plant macromolecules includes the step of shearing under pressure a portion of a plant of the present invention to produce a pulp containing a therapeutic immunoglobulin and plant macromolecules in an liquid derived from the apoplast or symplast of the plant and solid plant derived material. Further processing steps are contemplated which include separating the solid plant derived material from the liquid and using a portion of the plant including a leaf, stem, root, tuber, flower, fruit, seed or entire plant. The present invention contemplates the use of a mechanical device or enzymatic method which releases liquid from the apoplast or symplast of said plant followed optionally by separating using centrifugation, settling, flocculation or filtration.

The present invention contemplates immunoglobulins that are chimeric and thus they contain immunoglobulin domains derived from different immunoglobulin molecules.

Particularly preferred are immunoglobulins containing domains from IgG, IgM and IgA.

The present invention contemplates immunoglobulins where the immunoglobulin derived heavy chain is comprised of immunoglobulin domains from two different isotopes of immunoglobulin. In preferred embodiments, the immunoglobulin domains used include at least the $C_H1$, $C_H2$, or $C_H3$ domain of mouse IgG, IgG1, IgG2a, IgG2b, IgG3, IgA, IgE, or IgD or the Cvar domain. In other preferred embodiments, the immunoglobulin heavy chain is comprised of at least the $C\mu1$, $C\mu2$, $C\mu3$ or $C\mu4$ domain of mouse IgM.

The present invention also contemplates immunoglobulin derived heavy chains made up of immunoglobulin domains include at least the $C_H1$, $C_H2$, or $C_H3$ domain of a human IgG, IgG1, IgG2, IgG3, IgG4, IgA1, IgA2, or IgD; or least the $C\mu1$, $C\mu2$, $C\mu3$ or $C\mu4$ domain of human IgM; or the Cvar domain. The use of immunoglobulin domains derived from mammals, animals or rodents including any IgG isotype, any Iga isotype, IgE, IgM or IgD is contemplated.

The present invention also contemplates tetratransgenic organisms which are comprised of cells containing four different transgenes each encoding a different polypeptide of a multipeptide molecule wherein at least one of those peptides is associated together to form a multipeptide molecule. The transgenic organisms contemplated by the present invention include transgenic organisms which contain as one of the four transgenes present a transgene encoding a protection protein. The protection protein present in the transgenic organism's cells is able to assemble together with immunoglobulin heavy chains when present to form immunoglobulins which contain the protection protein.

In preferred transgenic organisms, the cells of the organism express four transgenes which encode an immunoglobulin derived heavy chain having at least a portion of an antigen binding domain, an immunoglobulin derived light chain having at least a portion of an antigen binding domain, an immunoglobulin J chain, and a protection protein. In other preferred transgenic organisms, the cells contain a transgene which encodes a chimeric immunoglobulin heavy chain, an immunoglobulin heavy chain derived form an IgA heavy chain, an immunoglobulin derived from an IgM heavy chain or an immunoglobulin derived from some other isotype of heavy chain.

In the most preferred embodiment, the transgenic organisms of the present invention are a plant. Various types and species of plants are contemplated by the present invention. In addition, the present invention also contemplates mammals which are transgenic organisms containing the various molecules of the present invention. Mammalian transgenic organisms are contemplated by the present invention and include mammalian transgenic organisms which contain four transgenes encoding different polypeptides.

BRIEF DESCRIPTION OF THE DRAWINGS

The drawings will first briefly be described.

DETAILED DESCRIPTION OF THE INVENTION

A. Definitions

Figure 1:
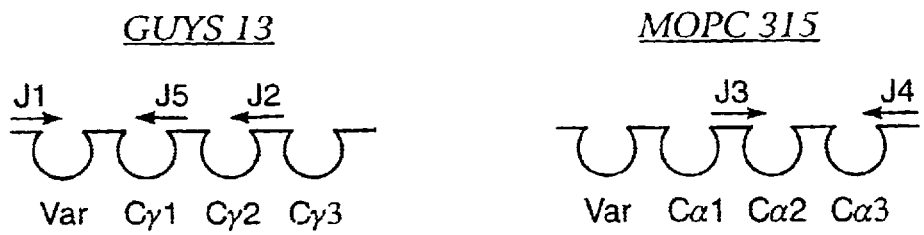
FIG. 1 illustrates synthetic oligonucleotides J1–J5 (restriction enzyme sites are underlined) that were used to amplify DNA fragments for Guy's 13 and alpha chain domains in the construction of hybrid IgG/A heavy chains. The relative positions of the areas encoded by each oligonucleotide are shown diagrammatically The resulting recombinant heavy chains produced by combining various DNA fragments expressed in plants are also shown.
Figure 1:
Figure 1:
Figure 1:

Dicotyledon (dicot): A flowering plant whose embryos have two seed halves or cotyledons. Examples of dicots are: tobacco; tomato; the legumes including alfalfa; oaks; maples; roses; mints; squashes; daisies; walnuts; cacti; violets; and buttercups.

Monocotyledon (monocot): A flowering plant whose embryos have one cotyledon or seed leaf. Examples of monocots are: lilies; grasses; corn; grains, including oats, wheat and barley; orchids; irises; onions and palms.

Lower plant: Any non-flowering plant including ferns, gymnosperms, conifers, horsetails, club mosses, liver warts, hornworts, mosses, red algaes, brown algaes, gametophytes, sporophytes of pteridophytes, and green algaes.

Eukaryotic hybrid vector: A DNA by means of which a DNA coding for a polypeptide (insert) can be introduced into a eukaryotic cell.

Extrachromosomal ribosomal DNA (rDNA): A DNA found in unicellular eukaryotes outside the chromosomes, carrying one or more genes coding for ribosomal RNA and replicating autonomously (independent of the replication of the chromosomes).

Palindromic DNA: A DNA sequence with one or more centers of symmetry.

DNA: Deoxyribonucleic acid.
T-DNA: A segment of transferred DNA.
rDNA: Ribosomal DNA.
RNA: Ribonucleic acid.
rRNA: Ribosomal RNA.
Ti-plasmid: Tumor-inducing plasmid.
Ti-DNA: A segment of DNA from Ti-plasmid.
Insert: A DNA sequence foreign to the rDNA, consisting of a structural gene and optionally additional DNA sequences.

Structural gene: A gene coding for a polypeptide and being equipped with a suitable promoter, termination sequence and optionally other regulatory DNA sequences, and having a correct reading frame.

Signal Sequence: A DNA sequence coding for an amino acid sequence attached to the polypeptide which binds the polypeptide to the endoplasmic reticulum and is essential for protein secretion.

(Selective) Genetic marker: A DNA sequence coding for a phenotypical trait by means of which transformed cells can be selected from untransformed cells.

Promoter: A recognition site on a DNA sequence or group of DNA sequences that provide an expression control element for a gene and to which RNA polymerase specifically binds and initiates RNA synthesis (transcription) of that gene.

Inducible promoter: A promoter where the rate of RNA polymerase binding and initiation is modulated by external stimuli. Such stimuli include light, heat, anaerobic stress, alteration in nutrient conditions, presence or absence of a metabolite, presence of a ligand, microbial attack, wounding and the like.

Viral promoter: A promoter with a DNA sequence substantially similar to the promoter found at the 5' end of a viral gene. A typical viral promoter is found at the 5' end of the gene coding for the p21 protein of MMTV described by Huang et al., Cell, 27:245 (1981). Other examples include the promoters found in the 35S transcript of the cauliflower mosaic virus as described by Benfey et al., Science, 250:959 (1990).

Synthetic promoter: A promoter that was chemically synthesized rather than biologically derived. Usually synthetic promoters incorporate sequence changes that optimize the efficiency of RNA polymerase initiation.

Constitutive promoter: A promoter where the rate of RNA polymerase binding and initiation is approximately constant and relatively independent of external stimuli. Examples of constitutive promoters include the cauliflower mosaic virus 35S and 19S promoters described by Poszkowski et al., *EMBO J.*, 3:2719 (1989) and Odell et al., *Nature,* 313:810 (1985).

Regulated promoter: A promoter where the rate of RNA polymerase binding and initiation is modulated at a specific time during development, or in a specific structure of an organism or both of these types of modulation. Examples of regulated promoters are given in Chua et al., *Science,* 244:174–181 (1989).

Single-chain antigen-binding protein: A polypeptide composed of an immunoglobulin light-chain variable region amino acid sequence ($V_L$) tethered to an immunoglobulin heavy-chain variable region amino acid sequence ($V_H$) by a peptide that links the carboxyl terminus of the $V_L$ sequence to the amino terminus of the $V_H$ sequence. Generally any combination of the heavy chain and light chain antigen binding domains into the same polypeptide using a linker polypeptide to allow the binding domains to assume a useful conformation. Such combinations include $V_H$-Linker-$V_L$, $V_H$-Linear-Light chain, or $V_L$-Linear-Fd.

Single-chain antigen-binding protein-coding gene: A recombinant gene coding for a single-chain antigen-binding protein.

Polypeptide and peptide: A linear series of amino acid residues connected one to the other by peptide bonds between the alpha-amino and carboxy groups of adjacent residues.

Protein: A linear series of greater than about 50 amino acid residues connected one to the other as in a polypeptide.

Immunoglobulin product: A polypeptide, protein or protein containing at least the immunologically active portion of an immunoglobulin heavy chain and is thus capable of specifically combining with an antigen. Exemplary immunoglobulin products are an immunoglobulin heavy chain, immunoglobulin molecules, substantially intact immunoglobulin molecules, any portion of an immunoglobulin that contains the paratope, including those portions known in the art as Fab fragments, Fab' fragment, F(ab')$_2$ fragment and Fv fragment.

Immunoglobulin molecule: A protein containing the immunologically active portions of an immunoglobulin heavy chain and immunoglobulin light chain covalently coupled together and capable of specifically combining with antigen.

Immunoglobulin derived heavy chain: A polypeptide that contains at least a portion of the antigen binding domain of an immunoglobulin and at least a portion of a variable region of an immunoglobulin heavy chain or at least a portion of a constant region of an immunoglobulin heavy chain. Thus, the immunoglobulin derived heavy chain has significant regions of amino acid sequence homology with a member of the immunoglobulin gene superfamily. For example, the heavy chain in an Fab fragment is an immunoglobulin derived heavy chain.

Immunoglobulin derived light chain: A polypeptide that contains at least a portion of the antigen binding domain of an immunoglobulin and at least a portion of the variable region or at least a portion of a constant region of an immunoglobulin light chain. Thus, the immunoglobulin derived light chain has significant regions of amino acid homology with a member of the immunoglobulin gene superfamily.

Antigen binding domain: The portion of an immunoglobulin polypeptide that specifically binds to the antigen. This antigen is typically bound by antigen binding domains of the immunoglobulin heavy and light chain. However, antigen binding domains may be present on a single polypeptide.

J chain: Is a polypeptide that is involved in the polymerization of immunoglobulins and transport of polymerized immunoglobulins through epithelial cells. See, The Immunoglobulin Helper: The J Chain in *Immunoglobulin Genes,* at pg. 345, Academic Press (1989). J chain is found in petameric IgM and dimeric IgA and typically attached via disulphide bonds. J chain has been studied in both mouse and human.

Fab fragment: A protein consisting of the portion of an immunoglobulin molecule containing the immuno-logically active portions of an immunoglobulin heavy chain and an immunoglobulin light chain covalently coupled together and capable of specifically combining with antigen. Fab fragments are typically prepared by proteolytic digestion of substantially intact immunoglobulin molecules with papain using methods that are well known in the art. However an Fab fragment may also be prepared by expressing in a suitable host cell the desired portions of immunoglobulin heavy chain and immunoglobulin light chain using methods well known in the art.

$F_V$ fragment: A protein consisting of the immunologically active portions of an immunoglobulin heavy chain variable region and an immunoglobulin light chain variable region covalently coupled together and capable of specifically combining with antigen. $F_v$ fragments are typically prepared by expressing in suitable host cell the desired portions of immunoglobulin heavy chain variable region and immunoglobulin light chain variable region using methods well known in the art.

Asexual propagation: Producing progeny by regenerating an entire plant from leaf cuttings, stem cuttings, root cuttings, single plant cells (protoplasts) or callus.

Self-pollination: The transfer of pollen from male flower parts to female flower parts on the same plant. This process typically produces seed.

Cross-pollination: The transfer of pollen from the male flower parts of one plant to the female flower parts of another plant. This process typically produces seed from which viable progeny can be grown.

Epitope: A portion of a molecule that is specifically recognized by an immunoglobulin product. It is also referred to as the determinant or antigenic determinant.

Chimeric immunoglobulin heavy chain: An immunoglobulin derived heavy chain having at least a portion of its amino acid sequence derived from an immunoglobulin heavy chain of a different isotype or subtype or some other peptide, polypeptide or protein. Typically, a chimeric immunoglobulin heavy chain has its amino acid residue sequence derived from at least two different isotypes or subtypes of immunoglobulin heavy chain.

Transgene: A gene that has been introduced into the germ line of an animal. The gene may be introduced into the animal at an early developmental stage. However, the gene could be introduced into the cells of an animal at a later stage by, for example, a retroviral vector.

Multiple molecule: A molecule comprised of more than one peptide or polypeptide associated together by any means including chemical bonds.

B. Immunoglobulins Containing Protection Proteins

The present invention provides novel methods for producing immunoglobulin molecules containing protection proteins. The immunoglobulins contain a protection protein in association with an immunoglobulin derived heavy chain that has at least a portion of an antigen binding domain.

The protection proteins of the present invention have an amino acid sequence substantially corresponding to or analogous to at least a portion of residues 1 to 627 of the amino acid residue sequence of the rabbit polyimmunoglobulin receptor and is derived from a precursor protein that does not contain the amino acid residue sequence greater than amino acid residue 627 or analogous to amino acid residue 627 of the rabbit polyimmunoglobulin receptor. The nucleotide sequence and the amino acid sequence of the rabbit polyimmunoglobulin receptor are now and have been described by the Mostov et al., Nature, 308:37 (1984) and EMBL/Gene Bank K01291. The nucleotide sequence of the polyimmunoglobulin receptor is SEQ ID NO. 1 and the corresponding amino acid residue sequence is SEQ ID NO. 2.

The polyimmunoglobulin receptors from any species may be used as a protection protein and these protection proteins do not contain and are derived from a precursor protein that does not contain amino acids having numbers greater than the amino acid number analogous to amino acids 1–627 of the rabbit immunoglobulin sequence. In preferred embodiments, the protection protein is derived from any species and precursor protein that contains amino acids analogous to at least a portion of amino acids 1–606 of the rabbit polyimmunoglobulin receptor and does not contain amino acid residues analogous to residues 607–755 of the rabbit polyimmunoglobulin receptor.

The human polyimmunoglobulin receptor sequence has been determined and reported by Krajci et al., Eur. J. Immunol., 22:2309–2315 (1992) and Krajci et al., Biochem. Biophys. Res. Comm., 158:783–789 (1989) and EMBL/Gene Bank Accession No. X73079. The nucleotide sequence of the human polyimmunoglobulin receptor is SEQ ID NO. 3 and the corresponding amino acid residue sequence is SEQ IS NO. 4. The human polyimmunoglobulin receptor shows extensive sequence homology and has an analogous domain structure to that of the rabbit polyimmunoglobulin receptor. See, Kraehenbuhl et al., Trends in Cell Biol., 2:170 (1992). The portions of the human polyimmunoglobulin receptor which are analogous to the domains and/or amino acid residues sequence of the rabbit polyimmunoglobulin receptor are shown in Table 1.

The rat polyimmunoglobulin receptor sequence has been determined and reported by Banting et al., FEBS Lett., 254:177–183 (1989) and EMBL/Gene Bank Accession No. X15741. The nucleotide of the rat polyimmunoglobulin receptor nucleotide sequence is SEQ ID NO. 9 and the corresponding amino acid residue sequence is SEQ ID NO 10. The rat polyimmunoglobulin receptor shows extensive sequence homology and has an analogous domain structure to that of the rabbit and human polyimmunoglobulin receptor. See, Kraehenbuhl et al., T. Cell Biol., 2:170 (1992). The portions of the rat polyimmunoglobulin receptor which are analogous to the domains and/or amino acid residue sequence of the rabbit polyimmunoglobulin receptor are shown in Table 1.

The bovine polyimmunoglobulin receptor sequence has been determined and reported in EMBL/Gene Bank Accession No. X81371. The bovine polyimmunoglobulin receptor nucleotide sequence is SEQ ID NO. 5 and the corresponding amino acid residue sequence is SEQ ID NO. 6. The bovine polyimmunoglobulin receptor shows extensive sequence homology and has an analogous domain structure to that of the rabbit and human polyimmunoglobulin receptor. The portions of the bovine polyimmunoglobulin receptor which are analogous to the domains and/or amino acid residues sequence of the rabbit polyimmunoglobulin receptor are shown in Table 1.

The mouse polyimmunoglobulin receptor sequence has been determined and reported by Piskurich et al., J. Immunol., 150:38 (1993) and EMBL/Gene Bank U06431. The mouse polyimmunoglobulin receptor nucleotide is SEQ ID NO. 7 and the corresponding amino acid residue sequence is SEQ ID NO. 8. The mouse polyimmunoglobulin receptor shows extensive sequence homology and has an analogous domain structure to that of the rabbit and human polyimmunoglobulin receptor. The portions of the mouse polyimmunoglobulin receptor which are analogous to the domains and/or amino acid residue sequence of the rabbit polyimmunoglobulin receptor are shown in Table 1.

In addition to the above-identified nucleic acid and corresponding amino acid residue sequences of the polyimmunoglobulin receptor from a variety of species, the present invention contemplates the use of a portion of a polyimmunoglobulin in receptor from any species. The conserved domain structure of the polyimmunoglobulin receptor between species allows the selection of analogous amino acid residue sequences within each polyimmunoglobulin receptor from different species. The present invention contemplates the use of such analogous amino acid residue sequences from any polyimmunoglobulin receptor. The analogous sequences from several polyimmunoglobulin receptor amino acid sequences is as shown in Table 1.

TABLE 1

Analogous Regions of the Amino Acid Residue Sequence of The Polyimmunoglobulin Receptor of Several Species. The nucleotide sequence coordinates approximately define the boundaries of the domains of molecules.

| Rabbit (SEQ ID NO.2) | Bovine (SEQ ID NO.6) | Human (SEQ ID NO.4) | Rat (SEQ ID NO.10) | Mouse (SEQ ID NO.8) |
|---|---|---|---|---|
| Immunoglobulin Binding Residues of Domain I 21–43 | about 13–45 | about 13–45 | about 13–45 | about 13–45 |
| domain I 1–118 | 1–120 | 1–120 | 1–120 | 1–120 |
| domain II 119–223 | 110–230 | 110–230 | 110–230 | 110–230 |
| domain III 224–332 | 210–340 | 210–340 | 210–340 | 210–340 |
| domain IV 333–441 | 320–450 | 320–450 | 320–450 | 320–450 |
| domain V 442–552 | 440–570 | 440–550 | 440–550 | 440–550 |
| External Portions of domain VI 553–606 & | 550–606 | 550–606 | 550–606 | 550–606 & |
| domain VI 553–627 | 550–627 | 550–627 | 550–627 | 550–627 |
| transmembrane segment 630–652 | 625–660 | 625–660 | 625–660 | 626–660 |
| intracellular portion 653–755 | 650–end | 650–end | 653–end | 653–end |

The protection proteins of the present invention may contain substantially less than the entire amino acid residue sequence of the polyimmunoglobulin receptor. In preferred embodiments the protection protein contains at least a portion of the amino acid residues 1 to 606 of the native polyimmunoglobulin receptor of rabbit. Unlike the native polyimmunoglobulin receptor, the protection proteins of the present invention are derived from precursor proteins that do not contain the entire amino acid residue sequence greater than the amino acid residue 627 derived from the native polyimmunoglobulin receptor and thus may contain more amino acids or fewer amino acids than secretory components. In preferred embodiments, the protection proteins of the present invention do not contain the entire amino acid residue sequence greater than amino acid residue 606 of the native polyimmunoglobulin receptor of rabbit. The present invention contemplates using only portions of the native polyimmunoglobulin receptor sequence as a protection protein. In other embodiments, it is contemplated that the protection protein may end at any amino acid between amino acid residue 606 to 627, including every amino acid position between 606 and 627, such as 607, 608, 609, 610, 611, 612, 613, 614, 615, 616, 617, 618, 619, 620, 621, 622, 623, 624, 625, 626.

In preferred embodiments, a protection protein of the present invention has an amino acid sequence which corresponds to one or more of the following amino acid segments:

1) amino acids (AA) corresponding to AA 21–43 of domain I of the rabbit polyimmunoglobulin receptor;
2) amino acids (AA) corresponding to AA 1–118 of domain I of the rabbit polyimmunoglobulin receptor;
3) amino acids (AA) corresponding to AA 119–223 of domain II of the rabbit polyimmunoglobulin receptor;
4) amino acids (AA) corresponding to AA 224–332 of domain III of the rabbit polyimmunoglobulin receptor;
5) amino acids (AA) corresponding to AA 333–441 of domain IV of the rabbit polyimmunoglobulin receptor;
6) amino acids (AA) corresponding to AA 442–552 of domain V of the rabbit polyimmunoglobulin receptor;
7) amino acids (AA) corresponding to AA of 553 to 606 or 553 to 627 of domain VI of the rabbit polyimmunoglobulin receptor; and does not contain amino acid residues corresponding to AA residues 607 to 755 or 638 to 755 of the rabbit polyimmunoglobulin receptor.

It should be noted the exact boundary of a domain may vary within approximately 20 amino acids. However, the domain structure and boundaries will be understood by one skilled in the art.

In addition, the present invention contemplates protection protein ending at the following amino acid residues of the rabbit polyimmunoglobulin receptor or at an amino acid residue which corresponds to the following residues but is in the polyimmunoglobulin receptor of another species: 580–605.

In other preferred embodiments, a protection protein has an amino acid sequence which corresponds to the amino acid sequence of a polyimmunoglobulin receptor for a particular species and which is analogous to the following amino acid segments:

i) amino acids (AA) corresponding to AA 21–43 of domain. I of the rabbit polyimmunoglobulin receptor;
2) amino acids (AA) corresponding to AA 1–118 of domain I of the rabbit polyimmunoglobulin receptor;
3) amino acids (AA) corresponding to AA 119–223 of domain II of the rabbit polyimmunoglobulin receptor;
4) amino acids (AA) corresponding to AA 224–332 of domain III of the rabbit polyimmunoglobulin receptor;
5) amino acids (AA) corresponding to AA 333–441 of domain IV of the rabbit polyimmunoglobulin receptor;
6) amino acids (AA) corresponding to AA 442–552 of domain V of the rabbit polyimmunoglobulin receptor;
7) amino acids (AA) corresponding to AA of 553–606 or 553–627 of domain VI of the rabbit polyimmunoglobulin receptor; and does not contain amino acid residues analogous to amino acid residues 607–755 or 630–755 of the rabbit polyimmunoglobulin receptor.

In other preferred embodiments, the protection protein comprises domains I, IV, V and AA 550–606 or 550–627 of domain VI of the rabbit polyimmunoglobulin receptor or the amino acid sequence from analogous domains and regions of a polyimmunoglobulin receptor from a different species.

In other embodiments, a protection protein of the present invention has an amino acid residue sequence which substantially corresponds to at least a portion of the amino acid residues from the polyimmunoglobulin receptor of a species which are analogous to amino acid residues 1–627 of the rabbit polyimmunoglobulin receptor. This portion of the amino acid sequence would correspond to at least a portion of the extracellular domains of the receptor of that species.

In preferred embodiments, a protection protein of the present invention has an amino acid sequence which substantially corresponds to at least a portion of the amino acid residues from the polyimmunoglobulin receptor of a species which are analogous to amino acid residues 1–606 of the rabbit polyimmunoglobulin receptor.

In other preferred embodiments, a protection protein of the present invention has an amino acid residue sequence which substantially corresponds to or is analogous to (if from a species other than rabbit) at least a portion of the following amino acid residue sequences:

1) amino acids (AA) corresponding to AA 21–43 of domain I of the rabbit polyimmunoglobulin receptor;
2) amino acids (AA) corresponding to AA 1–118 to of domain I of the rabbit polyimmunoglobulin receptor;
3) amino acids (AA) corresponding to AA 119–223 of domain II of the rabbit polyimmunoglobulin receptor;
4) amino acids (AA) corresponding to AA 224–332 of domain III of the rabbit polyimmunoglobulin receptor;
5) amino acids (AA) corresponding to AA 333–441 of domain IV of the rabbit polyimmunoglobulin receptor;
6) amino acids (AA) corresponding to AA 442–552 of domain V of the rabbit polyimmunoglobulin receptor;
7) amino acids (AA) corresponding to AA of 553–606 or 553–627 of domain VI of the rabbit polyimmunoglobulin receptor; and does not contain amino acid residues corresponding to AA 628 to 755 of the rabbit polyimmunoglobulin receptor.

In other preferred embodiments, the immunoglobulins of the present invention have a protection protein which has a first amino acid sequence which substantially corresponds to at least a portion of the amino acid residues 1 to 606 or 1 to 627 of the rabbit polyimmunoglobulin receptor and has a second amino acid residue sequence contiguous with said first amino acid sequence, wherein said second amino acid residue sequence does not have an amino acid residue sequence corresponding to the transmembrane segment of the rabbit polyimmunoglobulin receptor.

In more preferred embodiments, the second amino acid residue sequence has at least a portion of an amino acid sequence which corresponds to amino acid residues 655 to 755 of a polyimmunoglobulin receptor. In other preferred embodiments, the second amino acid residue is at least a portion of one or more of the following: an intracellular domain of a polyimmunoglobulin molecule, a domain of a member of the immunoglobulin gene superfamily, an enzyme, a toxin, or a linker.

The present invention contemplates protection proteins which do not have an amino acid residue corresponding to the transmembrane segment of rabbit polyimmunoglobulin receptor but may have amino acid residues corresponding to the intracellular domain of the rabbit polyimmunoglobulin receptor and this are deletion mutants of the receptor.

In other embodiments, protection proteins of the present invention have an amino acid sequence which substantially corresponds to at least one of the extracellular domains of polyimmunoglobulin receptor of a particular species. The protection protein, may have an amino acid sequence of which a segment of that amino acid sequence which substantially corresponds to an extracellular domain of the polyimmunoglobulin receptor of one species, and a different segment of that amino acid sequence may be from a second species and substantially correspond to an extracellular domain from a different species. This invention contemplates embodiments in which a protection protein has an amino acid sequence which has one amino acid sequence segment which corresponds to the amino acid sequence of the polyimmunoglobulin receptor from one species and has a second amino acid sequence within the same domain which corresponds to the amino acid and sequence of the polyimmunoglobulin receptor of a different species. Thus, the protection protein may have individual domains or portions of a particular domain that are comprised of amino acid sequences which correspond to the polyimmunoglobulin receptor from different species.

Other embodiments are contemplated in which protection protein has portions of its amino acid sequence derived from a molecule which is a member of the immunoglobulin superfamily. See, Williams and Barclay, "The Immunoglobulin Superfamily." In *Immunoglobulin Genes*, p. 361, Academic Press (Honjo Alt and Rabbits Eds. 1989). These derived portions may include amino acid sequences encoding peptides, domains or multiple domains from an immunoglobulin superfamily molecule.

The present invention also contemplates a nucleotide sequence encoding a protection protein which has a first nucleotide sequence encoding at least a portion of amino acids 1–606 or 1–627 of the rabbit polyimmunoglobulin receptor nucleotide sequence and which does not have a nucleotide sequence which encodes a functional transmembrane segment 3' of the first nucleotide sequence. Further preferred embodiments include a second nucleotide sequence located 3' of the first nucleotide sequence which encodes the amino acids 1–606 or 1–627 of the rabbit polyimmunoglobulin receptor sequence. This second nucleotide sequence may encode a variety of molecules including portions of the intracellular domain of rabbit polyimmunoglobulin receptor or another polyimmunoglobulin receptor or a portion of an immunoglobulin superfamily molecule. In addition, embodiments are contemplated in which this second nucleotide sequence encodes various effector molecules, enzymes, toxins and the like. Preferred embodiments include a second nucleotide sequence which encodes amino acid residues which correspond to amino acid residues 655 to 775 of the rabbit polyimmunoglobulin receptor or polyimmunoglobulin receptor from another species.

The present invention also contemplates expression vectors containing a nucleotide sequence encoding a protection protein which has been operatively linked to for expression. These expression vectors place the nucleotide sequence to be expressed in a particular cell 3' of a promoter sequence which causes the nucleotide sequence to be transcribed and expressed. The expression vector may also contain various enhancer sequences which improve the efficiency of this transcription. In addition, such sequences as terminators, polydenylation (poly A) sites and other 3' end processing signals may be included to enhance the amount of nucleotide sequence transcribed within a particular cell.

In preferred embodiments, the protection protein is part of an immunoglobulin that is in association with an immunoglobulin derived heavy chain having at least a portion of an antigen binding domain. Immunoglobulin derived heavy chains containing at least a portion of an antigen binding domain are well known in the art and have been described, for example, by Huse et al., *Science*, 246:1275 (1989), and by Lerner and Sorge, PCT Application WO 90/14430, published Nov. 29, 1990. The disclosure of these documents are hereby incorporated by reference.

In other embodiments, the immunoglobulins of the present invention contain a protection protein and immunoglobulin derived heavy chain and immunoglobulin derived light chain that contain at least a portion of an antigen binding site in association with the immunoglobulin derived heavy chain. Immunoglobulin light chains having at least a portion of an antigen binding domain are well known in the art and are described in available sources. See, for example, Early and Hood, *Genetic Engineering*, Setlow & Hollaender, (eds.), Vol. 3, Plenum Publishing Corp., New York (1981), pages 157–188; and Kabat et al., *Sequences of Immunologic Interest*, National Institutes of Health, Bethesda, Md. (1987). The disclosures of all references cited herein are hereby incorporated by reference.

The immunoglobulin components of the complex (alpha, J, kappa or lambda) can contain all or part of the full length polypeptide. Parts of these chains may be used to substitute for the whole chain. For instance, the entire immunoglobulin alpha heavy chain may be replaced by the variable region and only a portion of the alpha constant region sufficient to enable assembly with the other components. Likewise, a truncated kappa or lambda chain, containing only a small section of constant region can replace the full length kappa or lambda chains. The prerequisite of any complex is the ability to bind the protection protein.

In addition to truncated components, the present invention contemplates the combination of different types of immunoglobulins. For example, a heavy chain constant region comprising the $C_H1$ and $C_H2$ regions of IgG followed by the $C_H2$ and $C_H3$ regions derived from an IgA will form a stable complex containing the protection protein. This is specifically described as an example.

The immunoglobulins containing the protection proteins of the present invention preferably contain at least a portion of an IgM or IgA heavy chain which allows that immunoglobulin heavy chain to bird to immunoglobulin J chain and thereby bind to the protection protein. It is contemplated that the immunoglobulin heavy chain of the present invention may be comprised of individual domains selected from the IgA heavy chain or the IgM heavy chain or from some other isotype of heavy chain. It is also contemplated that an immunoglobulin domain derived from an immunoglobulin heavy chain other than IgA or IgM may be molecularly engineered to bind immunoglobulin J chain and thus may be used to produce immunoglobulins of the present invention.

One skilled in the art will understand that immunoglobulins consist of domains which are approximately 100–110 amino acid residues. These various domains are well known in the art and have known boundaries. The removal of a single domain and its replacement with a domain of another antibody molecule is easily achieved with modern molecular biology. The domains are globular structures which are stabilized by intrachain disulfide bonds. This confers a discrete shape and makes the domains a self-contained unit that can be replaced or interchanged with other similarly shaped domains. The heavy chain constant region domains of the immunoglobulins confer various properties known as antibody effector functions on a particular molecule containing that domain. Example effector functions include complement fixation, placental transfer, binding to staphyloccal protein, binding to streptococcal protein G, binding to mononuclear cells, neutrophils or mast cells and basophils. The association of particular domains and particular immunoglobulins isotopes with these effector functions is well known and for example, described in *Immunology*, Roitt et al., Mosby St. Louis, Mo. (1993 3rd Ed.)

The immunoglobulins of the present invention may, in addition to the protection protein, contain immunoglobulin heavy chains, immunoglobulin light chains, or immunoglobulin J chain bound to the immunoglobulin derived heavy chains. In preferred embodiments, the immunoglobulin of the present invention comprises two or four immunoglobulin derived heavy chains, together with two or four immunoglobulin light chains and an immunoglobulin J chain bound to at least one of the immunoglobulin derived heavy chains. The immunoglobulin J chain is described and known in the art. See, for example. M. Koshland, *The Immunoglobulin Helper: The J Chain.* in *Immunoglobulin Genes.* Academic Press, London, Pg. 345, (1989) and Matsuuchi et al., *Proc. Natl. Acad. Sci, U.S.A.*, 83:456–460 (1986). The sequence of the immunoglobulin J chain is available on various data bases in the United States.

The immunoglobulin of the present invention has a protection protein associated with at least an immunoglobulin derived heavy chain. This association may occur by hydrogen bonds, disulfide bonds, covalent bonds, ionic interactions or combinations of these various bonds. Typically, immunoglobulin molecules are held together by disulfide bonds between the immunoglobulin heavy chains and immunoglobulin light chains. The interaction of the protection protein with the immunoglobulin is by non-covalent or disulfide bonding.

The immunoglobulins of the present invention containing the protection protein, the immunoglobulin derived heavy chain and optionally an immunoglobulin derived light chain, and J chain are typically bonded together by one of the following: hydrogen bonds, disulfide bonds, covalent bonds, ionic interactions or combinations of these bonds. The present invention contemplates molecules in which the required portions of the immunoglobulin heavy, light and/or J chain have been placed into a single polypeptide and function to bind antigen and protection protein. Examples of such proteins are single-chain antigen-binding proteins.

The present invention contemplates a method of assembling a multimeric immunoglobulin comprising the steps of: introducing into an organism a DNA segment encoding all or part of an immunoglobulin J chain, and a DNA segment encoding all, or part of an immunoglobulin alpha chain, and a DNA segment encoding all or part of either an immunoglobulin kappa chain or an immunoglobulin lambda chain; and introducing into the same organism a protector, protein, said protection protein comprising at least a segment of the amino acid residues 1 to residue 606 of the rabbit polyimmunoglobulin receptor (pIgR) amino acid residue sequence or analogous amino acid residues from other species such that the segment is derived from a precursor protein that does not contain the amino acid residues comprising a functional membrane spanning region nor is the segment derived from a precursor protein in which the sequence of amino acid residues from the beginning of the membrane spanning region (approximately residue 630 of rabbit polyimmunoglobulin receptor) to the carboxyl end of the protein (approximately residue 755 of the rabbit polyimmunoglobulin receptor) are fully intact. In preferred embodiments the precursor protein does not contain amino acid residues greater than 606 of the rabbit polyimmunoglobulin receptor or analogous amino acid residues from other species.

As is understood by those of ordinary skill in the art, a membrane spanning region or functional transmembrane segment consists of a contiguous section of amino acid residues containing from about 20 to about 30 amino acids in which none of the residues is charged, virtually all of the residues are hydrophobic or non-polar, and the segment forms an alpha helix. A functional transmembrane segment is capable of spanning a biomembrane. Membrane spanning regions can be bounded by charged residues. An example of a membrane spanning region of pIgR is residues 630 to 653 of the polyimmunoglobulin receptor amino acid residue sequence of rabbit.

The chains that comprise the immunoglobulin containing the protection protein may be derived from precursors containing a signal sequence at the amino terminal of the protein. Each component can thereby be synthesized into an endomembrane system where assembly occurs. In addition to a signal sequence, the various components of the complex may or may not contain additional signals for N terminal glycosylation or for various other modifications which can affect the structure of the complex. In one embodiment of the invention, the signals for glycosylation (i.e. asparagine-X-serine or threonine or the signals for O-linked glycosylation) are not present or present in more or less places within the nucleotide sequence. The resulting antibody therefore would contain no carbohydrate, which may be advantageous for applications in which carbohydrates elicit an immune response.

In preferred embodiments, the immunoglobulin of the present invention contains a protection protein associated with an immunoglobulin derived heavy chain and the protection protein is free from N-linked and/or O-linked oligosaccharides. One skilled in the art will understand that a gene coding for a polypeptide having within its amino acid residue sequence the N-linked glycosylation signal asparagine-X-serine/threonine where X can be any amino acid residue except possibly proline and aspartic acid, when introduced into a plant cell would be glycosylated via oligosaccharides linked to the asparagine residue of the sequence (N-linked). See, Marshall, *Ann. Rev. Biochem.*, 41:673 (1972) and Marshall, *Biochem. Soc. Symp.*, 40:17 (1974) for a general review of the polypeptide sequences that function as glycosylation signals. These signals are recognized in both mammalian and in plant cells. One skilled in the art will understand that the N-linked glycosylation signal may be easily removed using common mutagenesis procedures to change the DNA sequence encoding the protection protein of the present invention. This mutagenesis typically involves the synthesis of oligonucleotide having the N-linked glycosylation signal deleted and then preparing a DNA strand with that oligonucleotide sequence incorporated into it. Such mutagenesis procedures and reagents are commercially available from many sources such as Stratagene (La Jolla, Calif.).

Assembly of the individual polypeptides that form a multi-peptide molecule (for example immunoglobulin) may be obtained by expressing in a single cell by directly introducing all the transgenes encoding the individual polypeptides into that cell either sequentially or all at once. The transgenes encoding the polypeptides may be present on individual constructs or DNA segments or may be contained in a DNA segment or construct together with one or more other transgenes.

Assembly of these components can be by cross pollination as originally described by Mendel to produce a population of segregants expressing all chains. Previous disclosures have demonstrated this to be an adequate method for the assembly and co-segregation of multimeric glycoconjugates. The disclosure of U.S. Pat. No. 5,202,422 is hereby incorporated by reference and describes these methods. In a preferred embodiment of the present invention, the antibody molecules contain a reduced number of glycans and antibody molecules with no glycans are contemplated.

The immunoglobulins of the present invention containing the protection protein, the immunoglobulin derived heavy chain and optionally an immunoglobulin derived light chain, and J chain may contain a protection protein that is free from N-linked oligosaccharides.

The immunoglobulins of the present invention that contain the protection protein are preferably therapeutic immunoglobulins that are useful in preventing a disease in an animal. In preferred embodiments, the immunoglobulins of the present invention are therapeutic immunoglobulins which are capable of binding to mucosal pathogen antigens. In other preferred embodiments, the therapeutic immunoglobulins of the present invention are capable of preventing dental caries. In the most preferred embodiment, the immunoglobulin of the present invention containing the protection protein contains an antigen binding domain that is capable of binding to an antigen from S. muans serotypes a, c, d, e, f, g and h (S. mutans c, e and f and S. sobrinus serotypes d and g under new nomenclature). Such antigen binding domains are known in the art and include, for example, the binding domains described in U.S. Pat. No. 5,352,446, J. K-C. Ma et al., Clin. Exp. Immunol. 77:331 (1989); and J. K-C. Ma et al., Eur. J. Immunol. 24:131–138 (1994); U.S. Pat. No. 5,352,446; U.S. Pat. No. 4,594,244; and European Patent Publication 371 017 B1. The disclosures of these documents are hereby incorporated by reference. In preferred embodiments, the immunoglobulins of the present invention are part of a composition that has a therapeutic activity on either animals or humans. Examples of therapeutic immunoglobulins are numerous, however, we envision the most appropriate therapeutic effect to be prophylaxis for mucosal and enteric pathogens by direct oral administration of the composition derived from an edible plant.

Administration of the therapeutic composition can be before or after extraction from the plant or other transgenic organism. Once extracted the immunoglobulins may also be further purified by conventional techniques such as size exclusion, ion exchange, or affinity chromatography. In the preferred embodiment, the transgenic organism is an edible plant and administration of the complex is by ingestion, after partial purification. Plant molecules may be co-administered with the complex.

The present invention also contemplates that the relative proportion of plant-derived molecules and animal-derived molecules can vary. Quantities of specific plant proteins, such as RuRisCo, or chlorophyll may be as little as 1% of the mass or as much as 99.9% of the mass of the extract, excluding water.

The present invention also contemplates the use of the therapeutic plant extract containing immunoglobulins having a protection protein directly without any further purification of the specific therapeutic component, e.g. the antibody. Administration may be by topical application, oral ingestion or any other method appropriate for delivering the antibody to the mucosal target pathogen. This form of administration is distinct from parenteral applications involving direct ingestion or commingling of the therapeutic plant extract with the blood stream.

The present invention also contemplates the use of the therapeutic plant extract containing immunoglobulins having a protection protein after manipulating the taste or texture of the extract. Appropriate quantities of gelling substances or flavorings could be added to enhance the contact of the antibody with the target pathogen in, for example, direct oral applications.

In preferred embodiments, the immunoglobulins of the present invention are used to passively immunize an animal against a preselected ligand by contacting a composition comprising an immunoglobulin containing a protection protein of the present invention that is capable of binding a preselected ligand with a mucosal surface of an animal. Passive immunization requires large amounts of antibody and for wide-spread use this antibody must be inexpensive.

Immunoglobulin molecules containing protection proteins that are capable of binding a preselected antigen can be efficiently and economically produced in plant cells. In preferred embodiments, the immunoglobulin molecule is either IgA, IgM, secretory IgM or secretory IgA or an immunoglobulin having a chimeric immunoglobulin heavy or light chain.

The immunoglobulins containing protection proteins are more resistant to proteolysis and denaturation and therefore are desirable for use in harsh environments. Contemplated harsh environments include acidic environments, protease containing environments, high temperature environments, and other harsh environments. For example, the gastrointestinal trace of an animal is a harsh environment where both proteases and acid are present. See, Kobayashi et al., Immunochemistry, 10;73 (1973).

Passive immunization of the animal using these more resistant immunoglobulins of the present invention is produced by contacting the immunoglobulin containing the protection protein with a mucosal surface of the animal. Animals have various mucosal surfaces including the lungs, the digestive tract, the nasopharyngeal cavity, the urogenital system, and the like. Typically, these mucosal surfaces contain cells that produce various secretions including saliva, lacrimal fluid, nasal fluid, tracheobronchial fluid, intestinal fluid, bile, cervical fluid and the like.

In preferred embodiments the immunoglobulins that contain the protection protein are immunospecific for a preselected antigen. Typically, this antigen is present on a pathogen that causes a disease that is associated with the mucosal surface such as necrotizing enterocolitis, diarrheal disease, ulcers, and cancer caused by carcinogen absorption in the intestine. See e.g., McNabb and Tomasi, Ann. Revl. Microbiol., 35:477 (1981) and Lawrence et al., Science, 243:1462 (1989). Typical pathogens that cause diseases associated with a mucosal surface include both bacterial and viral pathogens, such as E. coli. S. typhimurium, V. cholera, H. pylori, and S. mutans. See also. European Patent Application 484, 148 A1, published May 6, 1992 and hereby incorporated by reference. The immunoglobulins of the present invention are capable of binding to these pathogens and preventing them from causing mucosal associated diseases.

Immunoglobulins capable of binding to S. mutans and preventing dental caries have been described in European Patent Specification 371,017 which is hereby incorporated by reference. The disclosure of U.S. Pat. No. 5,352,440 is also hereby incorporated by reference.

Therapeutic immunoglobulins of the present invention that contain protection proteins that would be effective against bacterial infection or carcinomas are contemplated. Monoclonal antibodies with therapeutic activity have been described in U.S. Pat. Nos. 4,652,448, 4,443,549 and 5,183,756 which are hereby incorporated by reference.

In preferred embodiments, the immunoglobulin of the invention are part of a composition which is contacted with the animal mucosal surface comprises plant material and an immunoglobulin of the present invention that is capable of binding a preselected ligand. The plant material present may be plant cell walls, plant organelles, plant cytoplasms, intact plant cells, viable plants, and the like. This plant cell material is present in a ratio from about 10,000 grams of plant material to about 100 nanograms of immunoglobulin to about 100 nanograms of plant material for each 10 grams of immunoglobulin present. In more preferred embodiments, the plant material is present in a ratio from about 10,000 grams of plant material for each 1 gram of immunoglobulin present to about a ratio of 100 nanograms of plant material present for each gram of immunoglobulin present. In other preferred embodiments, the plant material is present in a ratio from about 10,000 grams of plant material for each milligram of immunoglobulin present to about 1 milligram of plant material present for each 500 milligram of immunoglobulin present.

In preferred embodiments, the composition containing the immunoglobulins of the present invention is a therapeutic composition. The preparation of therapeutic compositions which contain polypeptides or proteins as active ingredients is well understood in the art. Therapeutic compositions may be liquid solutions or suspensions, solid forms suitable for solution in, or suspension in a liquid prior to ingestion may also be prepared. The therapeutic may also be emulsified. The active therapeutic ingredient is typically mixed with inorganic and/or organic carriers which are pharmaceutically acceptable and compatible with the active ingredient. The carriers are typically physiologically acceptable excipients comprising more or less inert substances when added to the therapeutic composition to confer suitable consistencies and form to the composition. Suitable carriers are for example, water, saline, dextrose, glycerol, and the like and combinations thereof. In addition, if desired the composition can contain minor amounts of auxiliary substances such as wetting or emulsifying agents and pH buffering agents which enhance the effectiveness of the active ingredient. Therapeutic compositors containing carriers that have nutritional value are also contemplated.

In embodiments in which a composition containing an immunoglobulin having a protection protein of the present invention is applied to the tooth or mouth of a mammal, any convenient method may be used. Methods for applying such a composition to the teeth are well known and utilize various materials for a variety of purposes. For example, the composition may be directly applied to the tooth by painting the surface of the tooth with that composition. Alternatively, the composition of the present invention may be included in a toothpaste, mouthwash, chewing gum, lozenge or gel that will result in it being applied to the teeth. In some formulations, it may be desirable to provide for a formulation that prolongs the contact of the composition and therefore the immunoglobulin having the protection protein with the tooth surface. Formulations for this purpose are well known and include such formulations that may be placed in various dental trays that are used to cover the tooth and other dental apparatuses that are used in adjusting various conditions with the teeth.

The exact amount of a composition that must be applied to the teeth during any particular application is not critical because such treatment may be easily repeated at a given interval. For example, compositions present in toothpaste would be applied to the teeth each time that toothpaste is used, typically twice per day. For example, the order of 10 to 100 micrograms of an immunoglobulin having a protection protein can be applied to each tooth on each occasion the composition is applied to the teeth. However, this in no way should be taken as a limitation on a range that may be applied during any particular application as applications of a composition having more or less immunoglobulin of the present invention may be used without detrimental effect. The use of much lower concentrations of an immunoglobulin of the present invention would result in, at some point, a reduction in the protection provided by such formulation.

The exact formulation for the composition of the present invention may vary and will depend on the method of application to be used and the frequency of that application. In general, it may be any formulation which has an appropriate pH and which is free of material which would render the immunoglobulin having the protection protein of the present invention ineffective. For example, the compositions of the present invention may be applied as a simple aqueous solution in which the composition is disbursed at anywhere from 0.1 to 10 milligrams of immunoglobulin per 100 microliters of that solution. Generally, such a solution would be applied during dental surgery at a rate of approximately 1 to 10 microliters of the solution per tooth.

The formulations of the compositions of the present invention which are designed to be self-administered may vary and will be formulated taking in to account the frequency of application of the particular product in which is it used.

In preferred embodiments, a composition containing an immunoglobulin of the present invention comprises an immunoglobulin molecule that is immunospecific for a pathogen antigen. Pathogens are any organism that causes a disease in another organism. Particularly preferred are immunoglobulins that are immunospecific for a mucosal pathogen antigen. A mucosal pathogen antigen is present on a pathogen that invades an organism through mucosal tissue or causes mucosal associated diseases. Mucosal pathogens include lung pathogens, nasal pathogens, intestinal pathogens, oral pathogens, and the like. For a general discussion of pathogens, including mucosal pathogens, see, Davis et al., *Microbiology*, 3rd ed., Harper and Row, Hagerstown, Md. (1980).

Antibodies immunospecific for a pathogen may be produced using standard monoclonal antibody production techniques. See, *Antibodies: A Laboratory Manual*, Harlow et al., eds., Cold Spring Harbor, N.Y. (1988). The genes coding for the light chain and heavy chain variable regions can then be isolated using the polymerase chain reaction and appropriately selected primers. See, Orlandi et al., *Proc. Natl. Acad. Sci., U.S.A.*, 86:3833 (1989) and Huse et al., *Science*, 246:1275 (1989). The variable regions are then inserted into plant expression vectors, such as the expression vectors described by Hiatt et al., *Nature*, 342:76–78 (1989).

In a preferred embodiment, the immunoglobulin of the present invention is immunospecific for an intestinal pathogen antigen. Particularly preferred are immunoglobulins immunospecific for intestinal pathogens such as bacteria, viruses, and parasites that cause disease in the gastrointestinal tract, such as *E. coli, Salmonellae, Vibrio cholerae, Salmonellae typhimurin,* Shiaella and *H. pylori.*

In other preferred embodiments, the immunoglobulin containing the protection protein present in the composition is an immunoglobulin molecule that is immuno-specific for a dental pathogen such as *Streptococcus mutans* and the like. Particularly preferred are immunoglobulins immunospecific for a *Streptococcus mutans* antigen such as the immunoglobulin produced by hybridoma 15B2 (ATCC No. HB 8510);

the hybridoma deposited as European Collection of Animal cells Deposit No. 86031901; and the Guy's 13 monoclonal antibody described by Ma et al., *Eur. J. Immunol.*, 24:131 (1994) and Smith and Lehner, *Oral Micro. Immunol.*, 4:153 (1989).

The present invention contemplates producing passive immunity in an animal, such as vertebrate. In preferred embodiments, passive immunity is produced in fish, birds, reptiles, amphibians, or insects. In other preferred embodiments passive is produced in an mammal, such as a human, a domestic animal, such as a ruminant, a cow, a pig, a horse, a dog, a cat, and the like. In particularly preferred embodiments, passive immunity is produced in an adult or child mammal.

In preferred embodiments, passive immunity is produced in an animal, such as a mammal that is weaned and therefore no longer nurses to obtain milk from its mother. Passive immunity is produced in such an animal by administering to the animal a sufficient amount of composition containing an immunoglobulin containing a protection protein immunospecific for a preselected ligand to produce a prophylactic concentration of the immunoglobulin within the animal. A prophylactic concentration of an immunoglobulin is an amount sufficient to bind to a pathogen present and prevent that pathogen from causing detectable disease within the animal. The amount of composition containing the immunoglobulin of the present invention required to produce a prophylactic concentrations will vary as is well known in the art with the size of the animal, the amount of pathogen present, the affinity of the particular immunoglobulin for the pathogen, the efficiency with which the particular immunoglobulin is delivered to its active location within the animal, and the like.

C. Eukaryotic Cells Containing Immunoglobulins Having a Protection Protein

The present invention contemplates eukaryotic cells, including plant cells, containing immunoglobulins of the present invention. The present invention also contemplates plant cells that contain nucleotide sequences encoding the various components of the immunoglobulins of the present invention. One skilled in the art will understand that the nucleotide sequences that encode the protection protein and the various immunoglobulin heavy and light chains and J chain will typically be operably linked to a promoter and present as part of an expression vector or cassette.

After the immunoglobulin heavy and light chain genes, and J chain genes are isolated, they are typically operatively linked to a transcriptional promoter in an expression vector.

Expression of the components in the organism of choice can be derived from an independently replicating plasmid, or from a permanent component of the chromosome, or from any piece of DNA which may transiently give rise to transcripts encoding the components. Organisms suitable for transformation can be either prokaryotic or eukaryotic. Introduction of the components of the complex can be by direct DNA transformation, by ballistic delivery into the organism, or mediated by another organism as for example by the action of recombinant Agrobacteria on plant cells. Expression of proteins in transgenic organisms usually requires co-introduction of an appropriate promoter element and polyadenylation signal. In one embodiment of the invention, the promoter element potentially results in the constitutive expression of the components in all of the cells of a plant. Constitutive expression occurring in most or all of the cells will ensure that precursors can occupy the same cellular endomembrane system as might be required for assembly to occur.

Expression vectors compatible with the host cells, preferably those compatible with plant cells are used to express the genes of the present invention. Typical expression vectors useful for expression of genes in plants are well known in the art and include vectors derived from the tumor-inducing (Ti) plasmid of *Agrobacterium tumefaciens* described by Rogers et al., *Meth. in Enzymol.*, 153:253–277 (1987). However, several other expression vector systems are known to function in plants. See for example, Verma et al., PCT Publication. No. WO087/00551; and Cocking and Davey. *Science*, 236:1259–1262 (1987).

The expression vectors described above contain expression control elements including the promoter. The genes to be expressed are operatively linked to the expression vector to allow the promoter sequence to direct RNA polymerase binding and synthesis of the desired polypeptide coding gene. Useful in expressing the genes are promoters which are inducible, viral, synthetic, constitutive, and regulated. The choice of which expression vector and ultimately to which promoter a nucleotide sequence encoding part of the immunoglobulin of the present invention is operatively linked depends directly, as is well known in the art, or the functional properties desired, e.g. the location and timing of protein expression, and the host cell to be transformed, these being limitations inherent in the art of constructing recombinant DNA molecules. However, an expression vector useful in practicing the present invention is at least capable of directing the replication, and preferably also the expression of the polypeptide coding gene included in the DNA segment to which it is operatively linked.

In preferred embodiments, the expression vector used to express the genes includes a selection marker that is effective in a plant cell, preferably a drug resistance selection marker. A preferred drug resistance marker is the gene whose expression results in kanamycin resistance, i.e., the chimeric gene containing the nopaline synthase promoter. Tn5 neomycin phospho-transferase II and nopaline synthase 3' nontranslated region described by Rogers et al., in *Methods For Plant Molecular Biology*, a Weissbach and H. Weissbach, eds., Academic Press Inc., San Diego, Calif. (1988). A useful plant expression vector is commercially available from Pharmacia, Piscataway, N.J.

Expression vectors and promoters for expressing foreign proteins in plants have been described in. U.S. Pat. Nos. 5,188,642; 5,349,124; 5,352,605, and 5,034,322 which are hereby incorporated by reference.

A variety of methods have been developed to operatively link DNA to vectors via complementary cohesive termini. For instance, complementary homopolymer tracks can be added to the DNA segment to be inserted and to the vector DNA. The vector and DNA segment are then joined by hydrogen bonding between the complementary homopolymeric tails to form recombinant DNA molecules.

Alternatively, synthetic linkers containing one or more restriction endonuclease sites can be used to join the DNA segment to the expression vector. The synthetic linkers are attached to blunt-ended DNA segments by incubating the blunt-ended DNA segments with a large excess of synthetic linker molecules in the presence of an enzyme that is able to catalyze the ligation of blunt-ended DNA molecules, such as bacteria phage T4 DNA ligase. Thus, the products of the reaction are DNA segments carrying synthetic linker sequences at their ends. These DNA segments are then cleaved with the appropriate restriction endonuclease and ligated into an expression vector that has been cleaved with an enzyme that produces termini compatible with those of the synthetic linker. Synthetic linkers containing a variety of restriction endonuclease sites are commercially available from a number of sources including New England BioLabs, Beverly, Mass.

The nucleotide sequences encoding the protection protein and any other of the immunoglobulins of the present invention are introduced into the same plant cell either directly or by introducing each of the components into a plant cell and regenerating a plant and cross-hybridizing the various components to produce the final plant cell containing all the required components.

Any method may be used to introduce the nucleotide sequences encoding the components of the immunoglobulins of the present invention into a eukaryotic cell. For example, methods for introducing genes into plants include *Agrobacterium*-mediated plant transformation, protoplast transformation, gene transfer into pollen, injection into reproductive organs and injection into immature embryos. Each of these methods has distinct advantages and disadvantages. Thus, one particular method of introducing genes into a particular eukaryotic cell or plant species may not necessarily be the most effective for another eukaryotic cell or plant species.

*Agrobacterium tumefaciens*-mediated transfer is a widely applicable system for introducing genes into plant cells because the DNA can be introduced into whole plant tissues, bypassing the need for regeneration of an intact plant from a protoplast. The use of *Agrobacterium*-mediated expression vectors to introduce DNA into plant cells is well known in the art. See, for example, the methods described by Fraley et al., *Biotechnology*, 3:629 (1985) and Rogers et al., *Methods in Enzymology*, 153:253–277 (1987). Further, the integration of the Ti-DNA is a relatively precise process resulting in few rearrangements. The region of DNA to be transferred is defined by the border sequences and intervening DNA is usually inserted into the plant genome as described by Spielmann et al., *Mol. Gen. Genet.*, 205:34 (1986) and Jorgensen et al., *Mol. Gen. Genet.*, 207:471 (1987). Modern *Agrobacterium* transformation vectors are capable of replication in *Escherichia coli* as well as *Agrobacterium*, allowing for convenient manipulations as described by Klee et al., in *Plant DNA Infectious Agents*, T. Hohn and J. Schell, eds., Springer-Verlag, New York (1985) pp. 179–203. Further recent technological advances in vectors for *Agrobacterium*-mediated gene transfer have improved the arrangement of genes and restriction sites in the vectors to facilitate construction of vectors capable of expressing various polypeptide coding genes. The vectors described by Rogers et al., *Methods in Enzymology*, 153:253 (1987), have convenient multi-linker regions flanked by a promoter and a polyadenylation site for direct expression of inserted polypeptide coding genes and are suitable for present purposes.

*Agrobacterium*-mediated transformation of leaf disks and other tissues appears to be limited to plant species that *Agrobacterium tumefaciens* naturally infects. Thus, *Agrobacterium*-mediated transformation is most efficient in dicotyledonous plants. However, the transformation of Asparagus using *Agrobacterium* can also be achieved. See, for example, Bytebier, et al., *Proc. Natl. Acad. Sci.*, 84:5345 (1987).

In those plant species where *Agrobacterium*-mediated transformation is efficient, it is the method of choice because of the facile and defined nature of the gene transfer. However, few monocots appear to be natural hosts for *Agrobacterium*, although transgenic plants have been produced in asparagus using *Agrobacterium* vectors as described by Bytebier et al., *Proc. Natl. Acad. Sci. U.S.A.*, 84:5345 (1987). Therefore, commercially important cereal grains such as rice, corn, and wheat must be transformed using alternative methods. Transformation of plant protoplasts can be achieved using methods based on calcium phosphate precipitation, polyethylene glycol treatment, electroporation, and combinations of these treatments. See, for example, Potrykus et al., *Mol. Gen. Genet.*, 199:183 (1985); Lorz et al., *Mol. Gen. Genet.*, 199:178 (1985); Fromm et al., *Nature*, 319:791 (1986); Uchimiya et al., *Mol. Gen. Genet.*, 204:204 (1986); Callis et al., *Genes and Development*, 1:1183 (1987); and Marcotte et al., *Nature*, 335:454 (1988).

Application of these systems to different plant species depends upon the ability to regenerate that particular plant species from protoplasts. Illustrative methods for the regeneration of cereals from protoplasts are described in Fujimura et al., *Plant Tissue Culture Letters*, 2:74 (1985); Toriyama et al., *Theor Appl. Genet.*, 73:16 (1986); Yamada et al., *Plant Cell Rep.*, 4:85 (1986); Abdullah et al., *Biotechnology*, 4:1087 (1986).

To transform plant species that cannot be successfully regenerated from protoplast, other ways to introduce DNA into intact cells or tissues can be utilized. For example, regeneration of cereals from immature embryos or explants can be effected as described by Vasil, *Biotechnology*, 6:397 (1988). In addition, "particle gun" or high-velocity microprojectile technology can be utilized as well. Using such technology, DNA is carried through the cell wall and into the cytoplasm on the surface of small (0.525 um) metal particles that have been accelerated to speeds of one to several hundred meters per second as described in Klein et al., *Nature*, 327:70 (1987); Klein et al., *Proc. Natl. Acad. Sci. U.S.A.*, 85:8502 (1988); and McCabe et al., *Biotechnology*, 6:923 (1988). The metal particles penetrate through several layers of cells and thus allow the transformation of cells within tissue explants. Metal particles have been used to successfully transform corn cells and to produce fertile, stably transformed tobacco and soybean plants. Transformation of tissue explants eliminates the need for passage through a protoplast stage and thus speeds the production of transgenic plants.

DNA can be introduced into plants also by direct DNA transfer into pollen as described by Zhou et al., *Methods in Enzymology*, 101:433 (1983); D. Hess, *Intern Rev. Cytol.*, 107:367 (1987); Luo et al., *Plant Mol. Biol. Reporter*, 6:165 (1988). Expression of polypeptide coding genes can be obtained by injection of the DNA into reproductive organs of a plant as described by Pena et al., *Nature*, 325:274 (1987). DNA can also be injected directly into the cells of immature embryos and the rehydration of desiccated embryos as described by Neuhaus et al., *Theor. Apl. Genet.*, 75:30 (1987); and Benbrook et al., in *Proceedings Bio Expo 1986*, Butterworth, Stoneham, Mass., pp. 27–54 (1986).

The regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil.

The regeneration of plants containing the foreign gene introduced by *Agrobacterium tumefaciens* from leaf explants can be achieved as described by Horsch et al., *Science*, 227:1229–1231 (1985). In this procedure, transformants are grown in the presence of a selection agent and in a medium that induces the regeneration of shoots in the plant species being transformed as described by Fraley et al., *Proc. Natl. Acad. Sci. U.S.A.*, 80:4803 (1983). This procedure typically produces shoots within two to four weeks and these transformant shoots are then transferred to an appropriate root-inducing medium containing the selective agent and an antibiotic to prevent bacterial growth. Transformant shoots that rooted in the presence of the selective agent to form plantlets are then transplanted to soil to allow the production of roots. These procedures will vary depending upon the particular plant species employed, such variations being well known in the art.

The immunoglobulins of the present invention may be produced in any plant cell including plant cells derived from plants that are dicotyledonous or monocotyledonous, solanaceous, alfalfa, legumes, or tobacco.

Transgenic plants of the present invention can be produced from any sexually crossable plant species that can be transformed using any method known to those skilled in the art. Useful plant species are dicotyledons including tobacco, tomato, the legumes, alfalfa, oaks, and maples; monocotyledons including grasses, corn, grains, oats, wheat, and barley; and lower plants including gymnosperms, conifers, horsetails, club mosses, liver warts, horn warts, mosses, algaes, gametophytes, sporophytes of pteridophytes.

The plant cells of the present invention may in addition to the protection protein and the immunoglobulin derived heavy chain also contains a nucleotide sequence encoding an immunoglobulin derived light chain having at least a portion of an antigen binding domain.

The plant cells of the present invention may have an antigen binding domain that is capable of binding an antigen from *S. mutans* serotypes a, c, d, e, f, g, and h (*S. mutans* serotypes c, e, and f; and *S. sobrinus* serotypes d and g under new nomenclature) on the immunoglobulin derived heavy and light chains. The antigen binding domain present in these plant cells also can be able to bind to the responsible mucosal pathogens and prevent dental caries.

The plant cells of the present invention may be part of a plant and make up one of the following types of plants: dicotyledonous, monocotyledonous, solanaceous, alfalfa, tobacco or other type of plant.

D. Compositions Containing Immunoglobulins Having Protection Proteins

The present invention contemplates compositions of matter that comprise immunoglobulins of the present invention and plant macromolecules. Typically these plant macromolecules are derived from any plant useful in the present invention. The plant macromolecules are present together with an immunoglobulin of the present invention for example, in a plant cell, in an extract of a plant cell, or in a plant. Typical plant macromolecules associated with the immunoglobulins of the present invention in a composition are ribulose bisphosphate carboxylase, light harvesting complex, (LH6) pigments, secondary metabolites or chlorophyll. The compositions of the present invention have an immunoglobulin of the present invention present in a concentration of between 1% and 99% mass excluding water. Other preferred compositions include compositions having the immunoglobulins of the present invention present at a concentration of between 1% and 50% mass excluding water. Other preferred compositions include immunoglobulins at a concentration of 1% to 25% mass excluding water.

The compositions of the present invention contain plant macromolecules at a concentration of between 1% and 99% mass excluding water. Typically the mass present in the composition will consist of plant macromolecules and immunoglobulins of the present invention. When the immunoglobulins of the present invention are present at a higher or lower concentration the concentration of plant macromolecules present in the composition will vary inversely. In preferred embodiments the composition of plant macromolecules are present in a concentration of between 50% and 99% mass excluding water. In the most preferred compositions, the plant macromolecules are present in a concentration of between 75% and 99% mass excluding water.

The present invention contemplates a composition of matter comprising all or part of the following: an IgA heavy chain, a kappa or lambda chain, a J chain. These components form a complex and are attached to the protection protein as defined earlier. The composition also contains molecules derived from a plant. This composition may also be obtained after an extraction process yielding functional antibody and plant-derived molecules.

The extraction method comprises the steps of applying a force to a plant containing the complex whereby the apoplastic compartment of the plant is ruptured releasing said complex. The force involves shear, in dyn/cm2, as the primary method of releasing the apoplastic liquid.

The whole plant or plant extract contains an admixture of antibody and various other macromolecules of the plant. Among the macromolecules contained in the admixture is ribulose bisphosphate carboxylase (RuBisCo) or fragments of RuBisCo. Another macromolecule is LHCP. Another molecule is chlorophyll.

Shear force is a useful component of the overall force applied to the plant for disruption of apoplastic spaces. Other types of force may also be included to optimize the effects of shear. Direct pressure, for example, measured in lbs/in2, may enhance the effects of the apparatus used to apply shear. Commonly used homogenization techniques which are not appropriate for antibody extraction involve the use of high speed blades or cylinders which explosively destroy all plant structures.

The compositions of the present invention may contain an immunoglobulin of the present invention and plant molecules that are derived from a dicotyledonous, monocotyledonous, solanaceous, alfalfa, tobacco or other plant. The plant molecules present in the compositions of the present invention can be ribulose bisphosphate carboxylase, light harvesting complex, pigments, secondary metabolites, chlorophyll or other plant molecules.

Other useful methods for preparing composition containing immunoglobulins having protection protein include extraction with various solvents and application of vacuum to the plant material. The compositions of the present invention may contain immunoglobulins of the present in a concentration of between 1% and 99% mass excluding water. The compositions of the present invention may contain plant macromolecules in a concentration of between 1% and 99% mass excluding water.

Therapeutic compositions containing immunoglobulins of the present invention and plant macromolecules may be produced by processing a plant of the present invention by shearing under pressure a portion of that plant to produce a pulp containing the therapeutic immunoglobulin and plant macromolecules in a liquid derived from the apoplast or symplast of the plant which also contains the solid plant derived material. Further processing may be accomplished by separating the solid plant derived material from the plant derived liquid containing the immunoglobulins of the present invention. The starting material for such a process may include plant leaves, stem, roots, tubers, seeds, fruit or the entire plant. Typically, this processing is accomplished by a mechanical device which releases liquid from the apoplast or symplast of the plant. Additional processing steps may include separation of the solid plant derived material from the liquid using centrification settling flocculation or filtration. One skilled in the art will understand that these separation methods result in removing the solid plant derived material from the liquid including the immunoglobulins of the present invention. The methods of the present invention may produce immunoglobulins containing a protection protein and an immunoglobulin derived heavy chain that is comprised of domains or portions of immunoglobulin alpha chain and immunoglobulin gamma chain. The methods of the present invention may produce immunoglobulins containing a protection protein and an immunoglobulin derived light chain that is comprised of domains or portions of immunoglobulin kappa or lambda chain.

The methods of the present invention are operable on plant cells or part of a plant. The methods of the present invention may also include methods that further comprise growing the plant. The methods of the present invention may be applied to any plant including dicotyledonous, monocotyledonous, solanaceous, leguminous, alfalfa or tobacco plant. The methods of the present invention may be used to extract immunoglobulins from a portion of the plant such as a leaf, stem, root, tuber, seeds, fruit or entire plant. The methods of the present invention may use a mechanical device to shear the plants to release liquid from the apoplast or symplast of the plant. The plant pulp of the present invention may be separated to remove the solid plant material using one of the following methods: centrifugation, settling, flocculation or filtration.

E. Methods of Producing Immunoglobulins Containing Protection Proteins

The present invention contemplates methods of producing an immunoglobulin containing a protection protein comprising the steps of:

(a) Introducing into the plant cell an expression vector containing a nucleotide sequence encoding a protection protein operatively linked to a transcriptional promoter; and (b) Introducing into the same plant cell an expression vector containing a nucleotide sequence encoding an immunoglobulin derived heavy chain having at least a portion of an antigen binding domain operatively linked to a transcriptional promoter.

The methods of the present invention optionally include introducing into the plant cell containing the expression vector with the nucleotide sequences for the protection protein and the immunoglobulin derived heavy chain a nucleotide sequence encoding an immunoglobulin derived light chain at least having a portion of an antigen binding domain operatively linked to a transcriptional promoter. Methods are also contemplated that introduce into a cell that already contains nucleotide sequences and promoters operatively linked to encode a protection protein and an immunoglobulin heavy chain and an immunoglobulin light chain, a promoter operatively linked to a nucleotide sequence encoding J chain. This results in a cell containing the nucleotide sequences operatively linked to promoters for an immunoglobulin heavy chain and an immunoglobulin light chain, J chain and a protection protein.

The plant cells of the present invention may be present as part of a plant that is capable of growth. Particularly useful plants for this invention include dicotyledonous, monocotyledonous, solanaceous, legumes, alfalfa, tomato, and tobacco plants.

The methods of the present invention include producing an assembled immunoglobulin having heavy, light and J chains and a protection protein within a eukaryotic cell. This eukaryotic cell is produced by introducing into that cell nucleotide sequences operatively linked for expression encoding an immunoglobulin derived heavy chain having at least a portion of an antigen binding domain, an immunoglobulin derived light chain having at least a portion of an antigen binding domain, an immunoglobulin J chain, and a protection protein. These nucleotide sequences are operatively linked for expression by attaching appropriate promoters to each individual nucleotide sequence or to more than one nucleotide sequence thereby placing two nucleotide sequences encoding various molecules in tandem.

The eukaryotic cell produced by the present methods which contains these nucleotide sequences encoding the immunoglobulin heavy, light and J chains and the protection protein is maintained under conditions which allow those molecules to reproduce and assemble into an immunoglobulin which contains the protection proteins of the present invention.

The present invention also contemplates methods for making a particular immunoglobulin or antigen binding domain or domains of an immunoglobulin resistant to environmental conditions and more stable by operatively linking a nucleotide sequence encoding at least a portion of an antigen binding domain derived from an immunoglobulin heavy chain to a nucleotide sequence encoding at least one domain derived from an immunoglobulin $\alpha$ or $\mu$ heavy chain to form a nucleotide sequence encoding a chimeric immunoglobulin heavy chain. That nucleotide sequence encoding the chimeric immunoglobulin heavy chain is expressed in a eukaryotic cell which also contains at least one other molecule such as a protection protein, an immunoglobulin derived light chain having at least a portion of an antigen binding domain and an immunoglobulin J chain. In preferred embodiments, the cell contains all of the molecules including an immunoglobulin derived light chain having an antigen binding domain which is complementary to the antigen binding domain present on the immunoglobulin derived heavy chain. This method allows the chimeric immunoglobulin heavy chain to assemble with at least one other molecule, for example, the immunoglobulin derived light chain having the complementary antigen binding domain and an immunoglobulin J chain and the protection protein to form an immunoglobulin containing the protection protein which is resistant to environmental conditions.

These immunoglobulins are resistant to environmental conditions and thus more stable when subjected to elevated or reduced temperatures, high or low pH, high ionic or low ionic concentrations proteolytic enzymes and other harsh conditions. Such harsh conditions are typically found in the environment within natural water sources, within the human body, for example within the gut and on mucosal surfaces, and on the surface of an animal such as a mammal.

F. Chimeric Immunoglobulins Containing Protection Proteins

The present invention contemplates immunoglobulins containing a protection protein in which the immunoglobulin domains comprising the heavy and light chain are derived from different isotopes of either heavy or light chain immunoglobulins. One skilled in the art will understand that using molecular techniques these domains can be substituted for a similar domain and thus produce an immunoglobulin that is a hybrid between two different immunoglobulin molecules. These chimeric immunoglobulins allow immunoglobulins containing protection proteins to be constructed that contain a variety of different and desirable properties that are conferred by different immunoglobulin domains.

The present invention also contemplates chimeric immunoglobulins, including heavy, light and J chain which contain less than an entire domain derived from a different molecule. The same molecular techniques may be employed to produce such chimeric immunoglobulins.

In preferred embodiments, the immunoglobulins of the present invention contain at least the $C_H1$, $C_H2$, $C_H3$, domain of mouse IgG, IgG1, IgG2A, IgG2B, IgG3, IgA, IgE, or IgD. Other preferred embodiments of the present invention contain immunoglobulin domains that include at least the $C\mu1$, $C\mu2$, $C\mu3$, or $C\mu4$ domain of mouse IGM. Preferred immunoglobulins include immunoglobulins that contain the domains of $C\epsilon2$, $C\epsilon3$, and $C\epsilon4$ of mouse immunoglobulin IGE.

The present invention also contemplates chimeric immunoglobulins derived from human immunoglobulins. These chimeric immunoglobulins contain domains from two different isotypes of human immunoglobulin. Preferred immunoglobulins include immunoglobulins that contain immunoglobulin domains including at least the $C_H1$, $C_H2$, or $C_H3$ of human IgG, IgG1, IgG2, IgG3, IgG4, IgA1, IgA2, IgE, or IgD. Other preferred immunoglobulins include immunoglobulins that contain domains from at least the $C_H1$, $C_H2$, $C_H3$, or $C_H4$ domain of human IgM or IgE. The present invention also contemplates immunoglobulins that contain immunoglobulin domains derived from at least two different isotypes of mammalian immunoglobulins. Generally, any of the mammalian immunoglobulins can be used in the preferred embodiments, such as the following isotopes: any isotype of IgG, any isotype of IgA, IgE, IgD or IgM. The immunoglobulins of the present invention contained at least one of the constant region domains from two different isotopes of mammalian immunoglobulin.

The present invention also contemplates immunoglobulins that contain immunoglobulin domains derived from two different isotopes of rodent immunoglobulin. The isotopes of rodent immunoglobulin are well known in the art. The immunoglobulins of the present invention may contain immunoglobulin derived heavy chains that include at least one of the following immunoglobulin domains: the $C_H1$, $C_H2$, or $C_H3$ domain of a mouse IgG, IgG1, IgG2a, IgG2b, IgG3, IgA, IgE, or IgD; the $C_H1$, $C_H2$, $C_H3$, $C_H4$ domain of mouse IgE or IgM; the $C_H1$, $C_H2$, or $C_H3$ domain of a human IgG, IgG1, IgG2, IgG3, IgG4, IgA1, IgA2, or IgD; the $C_H1$, $C_H2$, $C_H3$, $C_H4$ domain of human IgM or IgE; the $C_H1$, $C_H2$, or $C_H3$ domain of an isotype of mammalian IgG, an isotype of IgA, IgE, or IgD; the $C_H1$, $C_H2$, $C_H3$, $C_H4$ domain of a mammalian IgE or IgM; the $C_H1$, $C_H2$, or $C_H3$ domain of an isotype of rodent IgG, IgA, IgE, or IgD; the $C_H1$, $C_H2$, $C_H3$, $C_H4$ domain of a rodent IgE or IgM; the $C_H1$, $C_H2$, or $C_H3$ domain of an isotype of animal IgG, an isotype of IgA, IgE, or IgD; and the $C_H1$, $C_H2$, $C_H3$, $C_H4$ domain of an animal IgE or IgM. The present invention also contemplates the replacement or addition of protein domains derived from molecules that are members of the immunoglobulin superfamily. The molecules that belong to the immunoglobulin superfamily have amino acid residue sequence and nucleic acid sequence homology to immunoglobulins. The molecules that are part of the immunoglobulin superfamily can be identified by amino acid or nucleic acid sequence homology. See, for example, p. 361 of *Immunoglobulin Genes*, Academic Press (1989).

Tetratransgenic Organisms:

The present invention also contemplates a tetratransgenic organism which is comprised of cells having incorporated into the nucleic acid of that cell or plant within the cell four different transgenes, each encoding a different polypeptide. These transgenes are different in that the messenger RNA and polypeptides produced from that transgene are different from the messenger RNA and polypeptides produced from the other of the four transgenes. Thus, the number of transgenes referred to in the present invention does not include multiple copies of the same transgene as is commonly found in transgenic organisms. The present invention is directed to transgenic organisms having four transgenes which are not identical copies of other transgenes. The present invention does not exclude the possibility that each of the four different transgenes may be present in multiple copies. However, at least four separate transgenes that are different are present within the cells of the transgenic organism.

In addition, the present invention contemplates that four different transgenes are related in that the transgenes encode a polypeptide that is part of a multipolypeptide molecule. Therefore, the present invention contemplates that each individual polypeptide chain of a multipeptide molecule would be present on a transgene within a cell of the transgenic organism. The expression of each individual different polypeptide of the multipeptide molecule allows the different polypeptides to associate together to form the multipeptide molecule within the transgenic animal's cells. Thus, the present invention does not include within the four different transgenes in each individual cell, transgenes which encode polypeptides which do not associate together to perform a multipeptide molecule. Examples of such transgenes encoding molecules that do not associate together are polypeptides for antibiotic resistance such as kanamycin or neomycin or thymidine kinase.

In preferred embodiments, the transgenes present within a transgenic organism of the present invention encode the following four different polypeptides: a protection protein; an immunoglobulin derived heavy chain having at least a portion of an antigen binding domain; an immunoglobulin derived light chain having at least a portion of an antigen binding domain; and an immunoglobulin J chain. In other preferred embodiments, one of the transgenes present in the transgenic organism encodes a chimeric immunoglobulin heavy, light or J chain. In other preferred embodiments, a transgene of the transgenic organisms of the present invention encode either an immunoglobulin heavy chain derived at least in part from an IgA or a IgM immunoglobulin. Other preferred embodiments include transgenic organisms containing transgenes which encode at least a portion of the amino acid sequence derived from an immunoglobulin heavy chain derived from either an IgA or IgM immunoglobulin heavy chain.

The present invention contemplates transgenic organisms including mammals, plants, rodents, reptiles, insects, amphibians, fishes or other organisms. In preferred embodiments, the transgenic organism of the present invention is a plant or a mammal. Methods of producing such organisms are well known. See, i.e., U.S. Pat. Nos. 4,736, 866; 4,607,388; 4,870,009 and 4,873,191 which are hereby incorporated by reference.

The present invention also contemplates immunoglobulin that contain immunoglobulin derived heavy or immunoglobulin derived light chains that contain immunoglobulin domains which have been engineered to make those domains less immunogenic in a particular species. Typically, the immunoglobulin molecule is engineered as to be "humanized" in that it appears to be a human immunoglobulin even though derived from various other species.

EXAMPLES

The following examples illustrate the disclosed invention. These examples in no way limit the scope of the claimed invention.

1. Construction of DNA Vectors For Expression of Antibodies in Plants.

a. Isolation of the Nucleotide Sequences Encoding the Guy's 13 Immunoglobulin

Molecular cloning of the gamma and kappa chains of the Guy's 13 anti-S. mutans antibody was done by the procedures described in Ma et al., Eur. J. Immunol., 24:131 (1994). Briefly, mRNA was extracted from the Guy's 13 hybridoma cell line and converted to the cDNA by standard procedures. The cDNA was then amplified with the use of a pair of oligonucleotides specifically complementary to either the gamma or kappa cDNA. Amplification was catalyzed by Taq 1 polymerase using a thermal cycler as described. The amplified cDNAs were then digested with the appropriate restriction endonucleases and ligated into the corresponding restriction site in a standard plant expression vector. Numerous examples of such vectors have been reported in the literature and are generally available. An example of one vector that may be used is pBIN19.

In a related series of experiments, the cDNAs were cloned into the bacterial vector bluescript. Using this construct, the sequence of the gamma and kappa cDNAs was determined using the methods of Maxam and Gilbert.

Procedures for cloning antibody cDNAs involving PCR techniques or by construction of cDNA libraries followed by ligation of the obtained cDNAs into appropriate vectors are commonplace techniques which are familiar to one of ordinary skill in the art.

b) Hybrid cDNAs encoding the Guy's 13 heavy chain variable region, a part of the gamma chain constant region and a part of an alpha chain constant region.

These constructs were synthesized as described in Ma et al., Eur. J. Immunol., 24:131 (1994) and ligated into the appropriate plant expression vectors as described above. The final construct had the structure: Guy's 13 variable region—(IgG1 $C_H1$)—(IgG1 $C_H2$)—(IgA $C_H2$)—(IgA $C_H3$), referred to as IgG2A heavy chain, and Guy's 13 variable region—(IgGlCH$_1$)—(IgACH2)—(IgACH3).

c) The Protection Protein and J chain.

The cloned rabbit polyimmunoglobulin receptor (pIgR) cDNA was described by Mostov, Nature, 308:37 (1984). The protection protein portion was obtained by PCR amplification of a portion of the nucleotide sequence coding for the (pIgR) and ligation into appropriate plant expression vectors ad described above. The protection protein portion the pIgR used in these constructs included the codon for amino acid number 11 to the codon for amino acid number 606. the method to accomplish this construction are well known in the art and the oligonucleotides can be selected using the pIgR nucleic acid sequence.

d) cDNAs encoding aglycosylated derivatives of heavy-chain constant regions.

Mutagenesis procedures were performed either according to Stratagene protocols. In each case (i.e. alpha constant region, or protection protein) the codon for the asparagine utilized as the attachment site for carbohydrates, was changed to a codon for histidine.

2. Production of Transgenic Plants Expressing Therapeutic Antibodies.

Plants and plant cells containing immunoglobulins having a protection protein were produced in the following manner.

a) Transfer of vectors to Agrobacterium tumefaciens

Plant transformation was accomplished by using Agrobacterium tumefaciens. E. coli DH5α bearing the recombinant pMON530 plant expression vector were mated with Agrobacterium in the presence of a helper strain (pRK2013) to provide transfer functions. Alternatively, pMON530 plasmid DNA was introduced into Agrobacteria by direct transformation. In this procedure, the Agrobacterium strain was first grown overnight at 28° C. in YEP medium. 2 ml of the overnight culture was used to inoculate 50 ml of YEP and was grown to an $OD_{600}$ of 1.0. The cells were then chilled to 4° C., pelletted by centrifugation and resuspended in 1 ml of ice cold 20 mM CaCl2. About 1 µg of DNA was added to aliquots of 0.1 ml of ice cold cells. The cells were then rapidly frozen by immersion in liquid nitrogen or in a dry ice ethanol bath. The cells were thawed by incubation at 37° C. for 5 minutes followed by the addition of 1 ml YEP medium. The cells were allowed to incubate for 2–4 hours with gentle shaking. Individual colonies carrying the recombinant vector were isolated by incubation on YEP agar plates containing the appropriate antibiotic.

Agrobacteria containing pMON530 were grown in media containing kanamycin, spectinomycin and chloramphenicol. Small segments of tobacco leaf were then co-cultivated with the Agrobacterium for 2 days after which the leaf segments were transferred to plates containing carbenicillin to kill the Agrobacterium. Regeneration of transformed leaf cells into whole plants was allowed to proceed in the presence of kanamycin selection until the plants were competent for growth in soil.

b) Regeneration of transformed tobacco and petunia plants.

Leaves from greenhouse grown tobacco or petunia plants were sterilized in 20% (by volume) Chlorox bleach, 0.1% sodium dodecyl sulfate at room temperature for 8 minutes. The leaves were then briefly rinsed in 70% ethanol and allowed to dry in sterile Petri plates.

Leaf discs of approximately 0.5 cm diameter were removed with a sterile hole puncher and placed on agar plates containing MS10 medium (MS10 medium per liter: 4.4 g Murashige and Skoog basal salts with minimal organics [Sigma #M68991, 30 g sucrose, 0.2 mg naphthalene acetic acid, 2 mg benzylaminopurine, 0.1 mg nicotinic acid, 0.1 mg pyridoxin, 0.1 mg thiamine, 10 g agar, pH 5.7 with KOH).

A 2 ml aliquot of a suspension of Agrobacterium in LB (approximately $1 \times 10^8$ Agrobacterium per ml) was then added to the leaf pieces. All surfaces of the leaf discs were contacted with Agrobacteria, excess liquid was poured off the plate, and the discs were co-cultivated with the bacteria for 2 days at room temperature. The discs were then transferred to agar plates containing MS10 medium, 50 µg/ml kanamycin and 250 µg/ml carbenicillin (MS10-KC). Regeneration was allowed to proceed with weekly transfer of discs to fresh MS10-KC plates until regenerating shoots were visible. Shoots were then transferred to agar plates containing MSO-KC medium (MSO-KC per liter: 4.4 g Murashige and Skoog basal salts with minimal organics [Sigma #M68991, 30 g sucrose, 1 mg nicotinic acid, 1 mg pyridoxin, 0.1 mg thiamine, 50 µg/ml kanamycin and 250 µg/ml carbenicillin, 10 g agar, pH 5.7 with KOH).

After root formation, plantlets were transferred to soil and grown to maturity.

c) Regeneration of transformed alfalfa Plants.

Alfalfa trifoliates were cut from a greenhouse grown plant and sterilized in 20% (v/v) Chlorox bleach, 0.1% sodium dodecyl sulfate at room temperature for 8 minutes. The trifoliates were then briefly rinsed in 70% ethanol and allowed to dry in sterile Petri plates.

Leaf pieces of approximately 1 cm×4 mm were cut with a sterile scalpel and placed on agar plates containing B5H medium (B5H medium per liter: 3.1 g Gamborg's powdered medium (Sigma #G5893), 500 mg KNO3, 250 mg MgSO4

7H2O, 30 g sucrose, 500 mg proline, 1 mg 2,4-dichlorophenoxyacetic acid, 100 µg kinetin, 100 mg inositol, 1 mg nicotinic add, 1 mg pyridoxin, 10 mg thiamine, 10 g agar, 30 ml stock amino acids, pH 5.7 with KOH; stock amino acids consist of 26.6 g L-glutamine, 3.32 g serine, 16.8 mg adenine, 333 mg glutathione per liter and are added after autoclaving when the medium is approximately 50° C.).

To the leaf pieces was then added 2 ml of a suspension of Agrobacterium in LB (approximately 1×10$^8$ Agrobacteria per ml). All surfaces of the leaf were contacted with Agrobacteria, excess liquid was poured off the plate, and the leaves were co-cultivated with the bacteria for 2 days at room temperature. The leaf pieces were then transferred to agar plates containing B5H medium, 25 µg/ml kanamycin and 250 µg/ml carbenicillin (B5H-KC). Regeneration was allowed to proceed with weekly transfer of leaf pieces to fresh B5H-KC plates until somatic embryos were visible. Embryos were then transferred to agar plates containing BI02Y-KC medium (BI02Y-KC per liter: 25 ml macronutrients, 10 ml micronutrients, 25 ml iron, 1 ml vitamins, 1 ml aminos, 2 g yeast extract, 100 mg myo-inositol, 30 g sucrose, 10 g agar, 25 mg kanamycin, 250 mg carbenicillin, pH 5.9 with KOH; macronutrients consist of 40 g KNO3, 40 g NH4NO3, 13.88 g Ca(NO3)2-4FUO, 1.4 g MgSO4-7H2O, 2.6 g KCl, 12 g Kh2PO4 per liter yielding a 4OX stock; vitamins consist of 100 mg thiamine HCl, 500 mg nicotinic acid, 100 mg pyridoxin-HCl per liter yielding a 100OX stock; aminos consists of 2 g per liter glycine yielding a 100OX stock; micronutrients consist of 580 mg MnSO4-4H2O, 1550 mg ZnSO4-7H2O, 160 mg H3BO3, 80 mg KI per liter yielding a 100X stock; iron consists of 1.28 g NaFeEDTA per liter yielding a 4OX stock).

After root formation, plantlets were transferred to soil and grown to maturity.

d) Regeneration of Transformed Tomato Plants.

Cotyledons from 7 day old tomato seedlings were sterilized in 20% (v/v) Chlorox bleach, 0.1% sodium dodecyl sulfate at room temperature for 8 minutes. The leaves were then briefly rinsed in 70% ethanol and allowed to dry in sterile Petri plates.

Cotyledon pieces of approximately 0.5 cm diameter were cut with a sterile scalpel and placed on agar plates containing MS4 medium (MS4 medium per liter: 4.4 g Murashige and Skoog basal salts with minimal organics [Sigma #M68991, 30 g sucrose, 2 mg zeatin riboside, 5 mg nicotinic acid, 0.5 mg pyridoxin, 0.5 mg thiamine, 1 mM acetosyringone, 10 g agar, pH 5.7 with KOH).

To the leaf pieces was then added 2 ml of a suspension of Agrobacterium in LB (approximately 1×10$^8$ Agrobacteria per ml). All surfaces of the leaf discs were contacted with Agrobacteria, excess liquid was poured off the plate, and the discs were co-cultivated with the bacteria for 2 days at room temperature. The discs were then transferred to agar plates containing MS4 medium minus acetosyringone containing 50 µg/ml kanamycin and 250 µg/ml carbenicillin (MS4-KC). Regeneration was allowed to proceed with weekly transfer of discs to fresh MS4-KC plates until regenerating shoots were visible. Shoots were then transferred to agar plates containing MSO-KC medium (MSO-KC per liter: 4.4 g Murashige and Skoog basal salts with minimal organics [Sigma #M68991, 30 g sucrose, 1 mg nicotinic acid, 1 mg pyridoxin, 10 mg thiamine, 50 µg/ml kanamycin and 250 µg/ml carbenicillin, 10 g agar, pH 5.7 with KOH).

After root formation, plantlets were transferred to soil and grown to maturity.

e) Regeneration of Transformed Arabidopsis Plants.

Intact roots derived from Arabidopsis thalliana plants grown in sterile culture were first pretreated on callus inducing medium (CIM) for 3 days at 28° C. in the dark (CIM medium per liter: 3.1 g Gamborg's powdered medium (Sigma #G5893), 30 g sucrose, 1 mg 2,4-dichlorophenoxyacetic acid, 100 µg kinetin, 1 mg inositol, 0.1 mg nicotinic acid, 0.1 mg pyridoxin, 0.1 mg thiamine, 8 g agar, pH 5.7 with KOH).

To the intact roots was then added 2 ml of a suspension of Agrobacterium in LB (approximately 1×10$^8$ Agrobacteria per ml). All surfaces of the roots were contacted with Agrobacteria and excess liquid was poured off the plate. The intact roots were then cut into 5 mm segments and were co-cultivated with the Agrobacteria for 2 days at 28° C. on CIM plates. The root pieces were then transferred to agar plates containing shoot inducing medium (SIM) containing 50 µg/ml kanamycin and 250 µg/ml carbenicillin (SIM medium per liter: 3.1 g Gamborg's powdered medium (Sigma #G5893), 30 g sucrose, 5 mg N$^6$-(2-isopentenyl) adenine, 150 µg indole-3-acetic acid, 1 mg inositol, 0.1 mg nicotinic acid, 0.1 mg pyridoxin, 0.1 mg thiamine, 8 g agar, pH 5.7 with KOH).

Regeneration was allowed to proceed with weekly transfer of root pieces to fresh SIM plates until green regenerating shoots were visible. Shoots were then transferred to agar plates containing EM medium (MSO-KC per liter: 4.4 g Murashige and Skoog basal salts with minimal organics [Sigma #M6899], 10 g sucrose, 1 mg indole-3-butyric acid 1 mg nicotinic acid, 0.1 mg pyridoxin, 0.1 mg thiamine, 250 µg/ml carbenicillin, 8 g agar, pH 5.7 with KOH).

After root formation, plantlets were transferred to soil and grown to maturity.

3. Identification of Transgenic Plants.

Kanamycin resistant transformants expressing individual immunoglobulin chains were identified by ELISA as described. Further analysis of the transformants included evaluation of RNA by Northern blotting and evaluation of immunoglobulin polypeptides by Western blotting, both as described in Maniatis et al.

For each immunoglobulin chain, antigenic material, RNA or protein were detected by the respective assays. Transformants identified as having the highest levels of immunoglobulin chains were used in cross pollination protocols.

4. Assembly of Antibodies by Cross Pollination of Transformants.

Cross pollinations were performed in order to obtain plants co-expressing the various components of the desired antibodies. These crosses yielded alfalfa, tomato, tobacco and Arabidopsis plants containing the following assembled components, all of which also contained the Guy's 13 antigen binding domain.

| Type of Antibody | Immunoglobulin Components |
| --- | --- |
| 1 | G1 heavy chain, kappa light chain |
| 2 | G2/A heavy chain, kappa light chain |
| 3 | G2/A heavy chain, kappa light chain, J chain |
| 4 | G1/A heavy chain, kappa light, J chain, protection protein |
| 5 | G1/A heavy chain Kappa light chain |

5. Extraction and Evaluation of Guy's 13 Type 1, 2 and 3 & 4 Antibodies From Transgenic Plants.

a) Extraction and enrichment of antibody contained in leaf.

Leaf pieces were chopped into approximately 1 cm² pieces. The pieces were then added to a cold solution of TBS having 10 μg/ml leupeptin (1 ml TBS per gram of leaf) contained in a chilled porcelain mortar both at approximately 4° C. Plant liquid was extracted by pulverizing the pieces with a cold pestle using a circular motion and hand pressure. Pulverizing was continued until the pieces became a nearly uniform pulp (approximately 3 minutes of pulverizing). The pulp was centrifuged at 4° C. and approximately 50,000×g to yield a supernatant devoid of solid plant pieces. Alternatively, the pulp was filtered through a plastic mesh with a pore size of approximately 100 microns.

Depending on the titer of antibody contained in the particular plant, the supernatant was either directly suitable for exposure to antigen or required enrichment to a suitable concentration. Yields of IgGl's or IgG/A's in the crude extract were routinely less than 10 μg/ml and averaged approximately 5 μg/ml. For applications of a Guy's 13 antibody to mucosal surfaces, enrichment to a concentration of 1 to 4 mg/ml may be required. As a Type 1, 2 or 3 construct, Guy's 13 antibody required a ten to forty-fold enrichment to yield the desired concentration. This was accomplished either by affinity adsorption (utilizing either Protein A or Protein G), or by lyophilization to remove water. Size exclusion chromatography was also used for enrichment but required complete fractionation of the crude extract to yield an antibody of the required concentration. By ELISA assay and by polyacrylamide gel electrophoresis, the co-expressed chains assembled into a complex of approximately 180–200 k daltons for types 1 & 2 and approximately 400 k daltons for type 3. Crude extracts were routinely obtained containing approximately of 5–10 μg/ml.

A dramatic increase in antibody accumulation was observed when the protection protein was crossed into a plant containing Type 3 antibody yielding a plant containing a Type 4 antibody. By ELISA assay and by polyacrylamide gel electrophoresis, the co-expressed chains assembled into a complex of approximately 470,000 daltons. Crude extracts were routinely obtained containing in excess of 200 μg/ml with an average of approximately 250 μg/ml. Therefore, the SIgA construct of the Guy's 13 antibody required minimal enrichment to achieve the target concentration. This enrichment could be accomplished by the techniques described above. Alternatively, it was found that the antibody is readily separated from the majority of plant molecules by a one ultrafiltration step using membrane with a molecular exclusion of 200,000 d.

b) Functionality of the Guy's 13 Type 4 Antibody.

Functional antibody studies were carried out by ELISA. All plants expressing antibody light and heavy chains assembled functional antibody that specifically recognized streptococcal antigen (SA I/II). The levels of binding and titration curves were similar to those of mouse hybridoma cell supernatants. No SA I/II binding was detected with plants expressing only J chain or only protection protein. Likewise, wild-type plants expressing no immunoglobulin showed no detectable levels of binding.

In a similar set of experiments, binding of antibody to immobilized purified streptococcal antigen or native antigen on the bacterial cell surface was detected using an anti-secretory component antiserum. In these assays, only the Type 4 antibody binding was detected. The functional Type 1, 2 or 3 antibodies did not bind the anti-secretory component antiserum. These results confirm that the protection protein was assembled with antibody in the plants expressing Type 4 constructs and in a manner which did not interfere with antigen binding.

6. Expression of Chimeric Immunoglobulins.

The genes encoding the heavy and light chains of a murine monoclonal antibody (mAb Guy's 13) have been cloned and expressed in *Nicotiana tabacum.* Transgenic plants have been regenerated that secrete full-length Guy's 13 antibody. By manipulation of the heavy chain gene sequence, constant region domains from an immunoglobulin alpha heavy chain have been introduced, and plants secreting Guy's 13 mAb with chimeric gamma/alpha heavy chains have also been produced. For each plant antibody, light and heavy chains have been detected by Western blot analysis and the fidelity of assembly confirmed by demonstrating that the antibody is fully functional, by antigen binding studies. Furthermore, the plant antibodies retained the ability to aggregate streptococci, which confirms that the bivalent antigen-binding capacity of the full length antibodies is intact.

a) Cloning of heavy and light chain genes

Messenger RNA was purified from the Guy's 13 and a murine IgA (MOPC315) hybridoma cell line, using an acid guanidiniumthiocyanate-phenol-chloroform extraction. Complementary DNA was made using Moloney murine leukemia virus reverse transcriptase (Promega, GB). DNA encoding the gamma and kappa chains of Guy's 13 amplified by polymerase chain reaction (PCR). The degenerate oligonucleotides used in the PCR were designed to incorporate a 5' terminal XhoI, and a 3'-terminal EcoRI restriction site in the amplified DNA fragments. Following restriction enzyme digestion, the immunoglobulin chain encoding DNA was ligated into a constitutive plant expression vector (pMON 530), which contains a mouse immunoglobulin leader sequence upstream of the cloning site. The recombinant vector was used to transform *E. coli* (DH5-α, Gibco BRL) and screening was by Southern blotting, using radiolabeled DNA probes derived from the original PCR products. Plasmid DNA was purified from positive transformants and introduced into *Agrobacterium tumefaciens.*

A similar approach was used to construct two forms of a hybrid Guy's 13 heavy chain. The synthetic oligonucleotides shown in FIG. 1 were used in PCR to amplify the regions: (a) Guy's 13 signal sequence to the 3' end of Cτ1 domain (J1–J5), (b) Guy's 13 signal sequence to the 3' end of Cτ2 domain (J1–J2), and (c) 5'end of Cα2 domain to the 3' terminus of DNA from the MOPC 315 hybridoma (J3–J4). The fragments were purified (Geneclean II, Bio 101, La Jolla, Calif.) and digested with HindIII for 1 h at 37° C. The Guy's 13 fragments were ligated to the MOPC 315 fragment with T4 DNA ligase (Gibco, BRL), at 16° C. for 16 h, and an aliquot of the reaction mixture was used as template DNA for a further PCR, using the 5' terminal oligonucleotide for Guy's 13 (J1) and the 3' terminal oligonucleotide for MOPC 315 (J4). Amplified DNA fragments were purified and ligated into the pMON 530 vector as described above. The vector used in this procedure did not have a previously inserted mouse leader sequence, as in this case, the DNA encoding the native Guy's 13 leader sequence was included in the PCR amplification.

b) Plant transformation and regeneration

Leaf discs, about 6 mm in diameter, were cut from surface-sterilized tobacco leaves (*Nicotiana tabacum,* var. *xanthii*) and incubated overnight at 28° C., with a culture of the recombinant *A. tumefaciens,* containing immunoglobulin cDNA inserts. The discs were transferred to culture plates containing a medium that induces regeneration of shoots, supplemented with kanamycin (200 mg/l) and carbenicillin (500 mg/l). Shoots developing after this stage were excised and transplanted onto a root-inducing medium, supplemented with kanamycin (200 mg/l). Rooted plantlets were transplanted into soil as soon as possible after the appearance of roots. Plants were screened for expression of immunoglobulin chains as described below. Those that expressed heavy chains were crossed with those expressing light chains, by cross-pollination. The resulting seeds were sown in soil and allowed to germinate. Twenty-two transgenic plants were regenerated from transformations with light or heavy chain constructs, as determined by ELISA. Crossing of light and heavy chain-secreting plants resulted in 3/10 F1 progeny plants expressing kappa and gamma chains together, 4/17 plants expressing both kappa and the plant G1/A heavy chain and 3/8 plants expressing both kappa and the plant G2/A heavy chain together.

The three different forms of Guy's 13 monoclonal antibody expressed in plants, therefore, all contain the identical light (kappa) chain, but different heavy chains. These will be abbreviated throughout this report as follows (FIG. 1): Guy's 13 IgG1 with original gamma heavy chain, plant G13, Guy's 13 with IgG/IgA hybrid heavy chain consisting of var-τ1-τ2-α2-α3 domains, plant G2/A. The Guy's 13 hybridoma cell culture supernatant used as a positive control will be abbreviated to Mouse G13. Negative control plants were those that had been transformed with pMON 530 vector containing an insert that encodes an irrelevant mouse protein.

c) Antibody chain detection

Production of either gamma, kappa or the gamma/alpha chain hybrids was detected by ELISA. Microtiter wells were coated with a goat anti-mouse heavy or light chain-specific IgG (Fisher, USA; Sigma, GB; Nordic Pharmaceuticals, GB) in 150 mM NaCl, 20 mM Tris-HCl (pH 8) (TBS). Blocking was with 5% non-fat dry milk in TBS at 4° C. overnight. Plant leaves were homogenized in TBS with leupeptin (10 µg/ml) (Calbiochem, USA). The supernatant was added in serial twofold dilutions to the microtiter plate and incubation was at 4° C. overnight. After washing with TBS with 0.05% Tween 20, bound immunoglobulin chains were detected with the appropriate goat anti-mouse heavy or light chain-specific antibody, conjugated with horseradish peroxidase (Fisher; Sigma; Nordic Pharmaceuticals), for 2 h at 37° C. Detection was with 2.2'-azino-di-(3-ethyl-benzthiazoline-sulfonate) (Boehringer, FRG).

A similar assay was used to determine the concentrations of the murine and plant Guy's 13 antibodies. These were compared with a mouse IgG1 mAb (MOPC 21), and a mouse IgA mAb (TEPC 21) used at known concentrations (Sigma). ELISA plates were coated with an anti-mouse kappa antiserum. After blocking, bound antibody was detected with horseradish peroxidase-labeled anti-mouse gamma or alpha antiserum. Antibody concentration was determined by comparison of binding curves for each antibody.

ELISA was also used to detect the binding function of the assembled antibody. Binding to SA I/II was detected using microtiter plates that had been coated with purified SA I/II at an optimized concentration of 2 µg/ml. The ELISA procedure was as described above. The ability to bind S. mutans or E. coli cells was detected using intact cells (strains Guy's c, S. mutans and DH5-α, E. coli) that had been grown to stationary phase, for 18 h at 37° C. and fixed in 10% formalin. All the antibody solutions were adjusted to an initial concentration of 1.5 µg/ml and used in serial twofold dilutions. Extracts from plants expressing wither Guy's 13 heavy or light chain singly were also included in these assays, to determine if the single immunoglobulin chains exhibited any antigen-binding activity. Antibodies bound to either cells or purified SA I/II were detected using a horseradish peroxidase-conjugated goat anti-mouse light or heavy chain antiserum (Nordic Pharmaceuticals). The results were expressed as mean±standard deviation of duplicate results from three separate assays.

Competition ELISA was performed on microtiter plates coated with purified SA I/II as above. The plates were incubated with plant extracts of Guy's 13 hybridoma supernatant at 1.5 µg/ml and serial twofold dilutions at 37° C. for 1 h and 4° C. overnight. After washing, $^{125}$I-labeled mouse Guy's 13 was added and left to incubate for 2 h at 37° C. The plates were washed again and the bound radioactivity was counted in a gamma counter (Hydragamma 16, Innotec, GB). The results are expressed as % inhibition of labeled mouse Guy's 13 binding, in which 100% is the radioactive count from wells to which no blocking solution had been added.

d) Western blot analysis

Aliquots of 10 µl of leaf homogenates were boiled with 75 mM Tris-HCl (pH 6.8), 2% SDS, under reducing and nonreducing conditions. SDS-PAGE in 10% acrylamide was performed, and the gels were blotted onto nitrocellulose. The blots were incubated for 16 h in TBS with 0.05% Tween 20 and 1% non-fat dry milk, followed by goat anti-mouse IgG1, kappa (Nordic Pharmaceutical) or alpha chain-specific antisera (Sigma), and incubated for 2 h at 37° C. After washing, the second-layer antibody, an alkaline phosphatase-conjugated rabbit anti-goat IgG (Sigma) was applied for 2 hours at 37° C. Antibody binding was detected by incubation with 300 µg/ml nitroblue tetrazolium and 15 p µg/ml 5-bromo-4-chloro-3-idolyl phosphate (Promega).

e) DNA sequencing

The DNA sequence of each cloned immunoglobulin gene insert confirmed that no mutations had occurred during PCR amplification or the cloning procedures. The introduction of the HindIII site in the λ/γ hybrid heavy chains resulted in the predicted addition of the leucine residue between the Cγ2 and Cα2 domains in Plant G2/A and leucine-lysine between the Cγ1 and Cα2 domains in Plant G1/A. The additional Cγ2 domain in the Plant G2/A construct is predicted to increase the length of the heavy chain by 141 amino acid residues (approximately 12000 Da). The plant G1/A heavy chain is predicted to be slightly larger than the native Guy's 13 heavy chain, by 33 amino acids, approximately 3000 Da.

Plasmid DNA that was purified from positive transformants in E. coli was sequenced. The immunoglobulin gene inserts were excised and sub-cloned into Bluescript (Stratagene, USA). The DNA sequence was determined by a di-deoxy termination procedure (Sequenase, USB, USA).

f) Expression of assembled antibody

Western blot analysis on extracts from three representative F1 progeny plants was performed and reported in FIG. 2 of Ma et al., Eur. J. Immunol., 24:131–138 (1994). Samples run under reducing conditions demonstrate the presence of light (kappa) chain at approximately 25 Kd, in the mouse Guy's 13, as well as in the three transgenic plants, but not in the control plant. Guy's 13 heavy (gamma) chain was also detected in plant G13 at approximately 57 Kd, but not in the control plant extract. A single protein species was detected, unlike the hybridoma producing the Guy's 13 antibody cell culture supernatant, in which a two protein species was a consistent finding. The difference in the molecular size of the mouse heavy chains is probably due to glycosylation differences, and the result suggests that in plants the two heavy chains may be glycosylated in the same way.

The heavy chains of plant G1/A and G2/A were detected with an anti-alpha chain antiserum. Compared with the mouse Guy's 13 heavy chain, (approximately 57 Kd), the heavy chain of plant G1/A has a slightly higher relative molecular mass (approximately 60 Kd) and the plant G2/A heavy chain is much larger (approximately 70 Kd). This is consistent with the molecular weights predicted by sequence analysis. Several other protein species were detected in the transgenic plant extracts. These are likely to be proteolytic fragments of either light/heavy chain complexes, or of the heavy chain, as no bands were detected in the extract from the control transgenic plant. The anti-alpha chain antiserum did not cross-react with the mouse Guy's 13, which only contains gamma chain domains.

Samples were also run under nonreducing conditions to confirm the assembly of heavy and light chains into an immunoglobulin molecule and reported in FIG. 3 of Ma et al., *Eur. J. Immunol.*, 24:131–138 (1994). Detection was with a labeled anti-kappa antiserum, and all three transgenic plants had assembled immunoglobulin at the correct $M_r$ of above 150 Kd for full-length antibody. The plant G13 antibody has the same $M_r$ as the mouse G13, but the plant G2/A and plant G1/A antibodies have higher $M_r$ as predicted. A number of smaller proteolytic fragments were also detected, which is consistent with previous findings and the fact that a number of proteases are released by plants during the antibody extraction procedure. That these are antibody fragments, is confirmed by the absence of any detectable bands in the control plant extract.

g) Antigen binding

Ten plants which were producing immunoglobulin were made in total, and the concentration of immunoglobulin in plant extracts varied between 1 and 10 µg/ml (mean 4.5 µg/ml). For the murine antibody and the representative plants used in this study, the concentrations estimated by ELISA were: mouse IgG-15.4 µg/ml, plant IgG-7.7 µg/ml, plant G1/A-1.5 µg/ml and plant G2/A-2.1 µg/ml. The concentrations determined for plant antibodies containing hybrid heavy chains are possibly underestimated, as they do not carry all of the constant region determinants, as compared with the standard mAb IgA used.

Titration curves for extracts from the three representative transgenic plants binding to SA I/II were generated and reported in FIG. 4 of Ma et al., *Eur. J. Immunol.*, 24:131–138 (1994). Specific antibody was detectable in all three transgenic plant extracts, and the titration curves were similar to that of the murine hybridoma cell culture supernatant, used at the same concentration. The binding of the plant G1/A antibody appeared to be slightly lower than the other antibodies, although the titration curve followed a similar pattern. No SA I/II binding activity was detected in the negative control plant nor did extracts from plants individually expressing light or heavy chains have binding activity towards purified SA I/II. These findings demonstrate that the transgenic plants expressing both light and heavy chains have assembled the antibody molecule correctly to form a functional antigen binding site and that single light or heavy chains are not capable of binding the antigen.

The plant antibodies also recognized native antigen on the surface of streptococcal cells as shown in FIG. 5 of Ma et al., *Eur. J. Immunol.*, 24:131–138 (1994) (*S. mutans* serotype c), which further confirms the integrity of the antigen-binding site in the plant antibodies. There were no significant differences between the binding of the different antibodies. Neither extracts from control plants, nor plants expressing only heavy or light chains showed any binding to *S. mutans* cells. There was no binding to *E coli* cells by any of the plant extracts, at concentrations of 1.0 and 0.5 µg/ml.

The plant antibodies competed with the original mouse Guy's 13 mbAb for binding to SA I/II. Up to 85% inhibition of $^{125}$I-labeled mouse Guy's 13 mAb binding to SA I/II was demonstrated using the plant antibodies as shown in FIG. 6 of Ma et al., *Eur. J. Immunol.*, 24:131–138 (1994). As before, the inhibition titration curves of the plant antibodies were similar to each other, and comparable to that of the mouse Guy's 13, whereas the control plant extract gave no inhibition.

h) Aggregation of *S. mutans*

The action of the immunoglobulin produced in plants having the Guy's 13 antigen binding region on bacteria was determined and reported in FIG. 7 of Ma et al., *Eur. J. Immunol.*, 24:131–138 (1994). Plant extracts were sterilized by filtration through a 0.22 µm pore size filter and diluted tenfold with Todd Hewitt broth. The samples were inoculated with 0.05 vol of an overnight *S. mutans* culture and incubated at 37° C. overnight. The samples were Gram stained and examined under oil immersion microscopy. *S. mutans* grown in the presence of mouse Guy's 13, plant Guy's 13, plant G1/A or plant G2/A became aggregated and cell clumping was evident. However, the control plant extract had no effect on *S. mutans* growth. None of the plant mAb appeared to affect *S. mutans* rate of growth, as determined by culture of viable organisms at 8, 12 and 16 h. The result demonstrates not only that the plant antibodies have correctly assembled antigen-binding regions, but also that the antibody molecules bind antigen bivalently.

Example 7

Production of Immunoglobulins Containing Protection Proteins

Four transgenic *Nicotiana tabacum* plants were generated to express (1) a murine monoclonal immunoglobulin kappa chain having the antigen binding site of the Guy's 13 light chain, (2) a hybrid IgA/G murine immunoglobulin heavy chain containing Cγ and Cα chain domains and the antigen binding site of the Guy's 13 heavy chain, (3) a murine J chain and (4) protection protein comprised of amino acids 1–606 of rabbit polyimmunoglobulin receptor and did not contain amino acids 627–675 of the rabbit polyimmunoglobulin receptor. See, Example 1. Successive sexual crosses between these plants resulted in simultaneous expression of all four protein chains in the progeny plants. In some cases, back crossing was used to produce homozygous plants. The four recombinant polypeptides were assembled into a functional, high molecular weight immunoglobulin containing a protection protein of approximately 470,000 Kd. The assembly of the protection protein with the immunoglobulin was dependent on the presence of a J chain, as no association of the protection protein was detected when plants expressing antibody alone were crossed with those expressing the protection protein. Microscopic evaluation of plants expressing the immunoglobulins containing the protection protein demonstrated co-incident expression of protection protein and immunoglobulin heavy chains in single cells. Single cells are able to produce immunoglobulin having a protection protein in transgenic plants, whereas two cells are required for natural production of secretory immunoglobulin in mammals. The results demonstrate that sexual crossing of transgenic plants expressing recombinant sub-units is suitable for large scale production of immunoglobulin containing a protection protein for passive immunotherapy, as well as for expressing other complex protein molecules.

The immunoglobulin which contains the protection protein has the heavy and light chain antigen binding domains from the Guy's 13 monoclonal antibody that specifically recognize the cell surface adhesion molecule SA 1/ll of an oral streptococcus as shown by Smith, R. & Lehner, T. *Oral Microbiol. Immunol.* 4, 153–158 (1989). Transgenic immunoglobulin of this type containing only heavy and light chains has been generated in *Nicotiana tabacum* plants as described in Example 6. A mouse J chain construct containing the coding length cDNA was amplified using synthetic oligonucleotide primers corresponding to the *N terminus* MKTHLL and the *C terminus* SCYPD of mouse J chain as described by Matsuuchi, L., Cann, G. M. & Koshland, M. E. *PNAS* 83, 456–460 (1986). This amplified nucleotide sequence was ligated into a constitutive plant expression vector, pMON 530, that includes the 35S promoter from Cauliflower Mosaic Virus and has been described by Rogers, S. G., Klee, H. J., Horsch, R. B. & Fraley, R. T. *Meth. Enzymol.* 153, 253–276 (1987). Tobacco leaf tissue was transformed using agrobacterium containing the recombinant plasmid as described in the previous Examples. Regenerated plants were screened for the production of messenger RNA encoding J chain and positive transformants were self fertilized in order to generate homozygous progeny. The J chain expressing plants were crossed initially with those expressing the chimeric immunoglobulin heavy chain and kappa chain. Western blot analysis of the plant extract from plants expressing the chimeric immunoglobulin heavy chain with anti-kappa antiserum under non-reducing conditions, revealed a protein species of approximately 210 Kd, which is consistent with the presence of the extra constant region domains present in the chimeric immunoglobulin heavy chain, as compared with the original IgG1 antibody. The progeny from the cross between the plant expressing the immunoglobulin and a J chain plant resulted in the appearance of a major immunoglobulin band at approximately twice the relative molecular mass of approximately 400 Kd, demonstrating that assembly of the 3 polypeptides had occurred to form dimeric immunoglobulin (dIgA/G).

The protection protein construct consisted of a coding length cDNA amplified using synthetic oligonucleotide primers corresponding to the *N terminus* MALFLL and AVQSAE at amino acids 601–606 of the *C terminus* of rabbit polyimmunoglobulin receptor. The nucleotide sequence of the rabbit polyimmunoglobulin receptor was reported by Mostov, K. E., Friedlander, M. & Blobel, G. *Nature* 308, 37–43 (1984). The protection protein was generated in transgenic plants as described above and positive transformants expressing the protection protein were identified by Western blot analysis.

Plants expressing J chain assembled with the immunoglobulin having the IgA/G heavy chains to form dimers were then crossed with a homozygous plant expressing the protection protein. The progeny plants expressing the immunoglobulin having the protection protein contained a higher molecular weight protein species at approximately 470 Kd as determined by Western blot analysis under non-reducing conditions. This molecular size was consistent with that expected for an immunoglobulin containing a protection protein. This high molecular weight protein contained the protection protein as confirmed by Western blotting, using antiserum that specifically recognized the protection protein. The plant extracts also contained a protein species of approximately 400 Kd corresponding to the dimers of IgA/G and a protein species of approximately 210 Kd corresponding to the immunoglobulin with the chimeric heavy chain, but these were only detected by anti-kappa antiserum and not the anti-protection protein antiserum. In the transgenic plant producing the protection protein alone, there was no evidence that the protection protein assembled with endogenous plant proteins or formed multimers, as no high molecular weight proteins were detected in Western blotting under non-reducing conditions. Western blot analysis demonstrated that extracts from the plants expressing immunoglobulin heavy chain (IgA/G, dimeric IgA/G and the immunoglobulin containing a protection protein), but not the plants containing only the protection protein or J chain or wild-type plants, contained identical immunoglobulin derived heavy and light chains. Furthermore, only the plants containing protection proteins and the plants containing the IgG/A immunoglobulin having the protection protein expressed proteins that were recognized by the antiserum that specifically recognized the protection protein. No cross reacting proteins were detected in extracts from the wildtype control plant.

In mammals, the assembly of secretory component with the immunoglobulin requires the presence of J chain as described by Brandtzaeg, P. & Prydz, H. *Nature* 311, 71–73 (1984). Plants expressing immunoglobulins containing a chimeric heavy chain (IgA/G) were crossed with plants expressing protection protein. None of the 10 resulting progeny that expressed immunoglobulin and the protection protein without J chain produced assembled complexes as compared with the 10/10 plants that co-expressed J chain dimerized immunoglobulin and the protection protein without J chain, which assembled the $M_r$ 470 Kd immunoglobulin containing the protection protein. This confirms that J chain is required for the protection protein association with immunoglobulin as found in mammals. Only the approximately 210 Kd monomeric form of the immunoglobulin was recognized by anti-kappa antiserum, and the antisera that specifically bound the protection protein, recognized free protection protein, but no immunoglobulin heavy or light chains proteins.

Functional studies were carried out using the immunoglobulin produced in the 5 plant constructs using ELISA. All plants expressing immunoglobulin light and heavy chains, assembled functional immunoglobulin that specifically recognized streptococcal antigen (SA I/II). The levels of binding and titration curves were similar to those of the native mouse hybridoma cell supernatant. No SA I/II binding was detected in plants expressing only J chain or only protection protein or in wildtype plants. Binding of the immunoglobulins to immobilized purified streptococcal antigen or to native antigen on the bacterial cell surface was also detected using the antiserum which specifically binds the protection protein. In these assays, the binding of the immunoglobulin containing the protection protein to the streptococcal antigen was specifically detected. These results confirmed that the protection protein was assembled with the immunoglobulin to produce an immunoglobulin containing a protection protein in a manner which did not interfere with antigen binding.

The assembly of heavy and light chains into functional immunoglobulin molecules in plants is very efficient as shown by Hiatt, A. C., Cafferkey, R. & Bowdish, K. *Nature* 342, 76–78 (1989). A signal peptide must be present on both heavy and light chain constructs to direct the recombinant proteins to the endoplasmic reticulum antibody for assembly to take place in plants as was previously shown by Hiatt, A. C., Cafferkey, R. & Bowdish, K. *Nature* 342, 76–78 (1989). This study has demonstrated the fidelity of immunoglobulin assembly which includes dimerization of monomeric antibody by J chain in the transgenic plants. These results demonstrated that in plants the dimeric immunoglobulin population represents a major proportion (approx. 57%) of the total antibody. These results also demonstrate the production of an assembled immunoglobulin containing a protection protein which binds the corresponding antigen as well as the parent murine monoclonal antibody, which makes up a major proportion of the total antibody when the protection protein is incorporated (approximately 45%).

Co-expression of dimeric immunoglobulin with the protection protein in plants has led to assembly of a functional immunoglobulin containing a protection protein. All four transgenes for this complex protein were introduced into plants with the identical pMON530 expression cassette and native leader sequences. This vector contains a promoter sequence derived from the 35S transcript of the cauliflower mosaic virus which directs expression of transgenes in a variety of cell types of most plant organs as has been described by Benfey, P. N. & Chua, N-H. *Science* 250, 959–966 (1990); and Barnes, W. M. PNVAS 87, 9183–9187 (1990). Directing expression of all four transgenes with the same promoter maximized the likelihood of coincidental expression in a common plant cell. Microscopic observation of plants expressing an immunoglobulin containing a protection protein revealed that many cell types of the leaves contain the individual protein components that make up the immunoglobulin. These proteins accumulated at highest concentration in bundle sheath cells and were confined by the cell walls of these and other cells, but were not found in intercellular spaces. Restriction of the largest immunoglobulin components, the protection protein and the chimeric immunoglobulin heavy chain, within the confines of a protoplastic or apoplastic compartment of individual cells would constrain the assembly of the secretory immunoglobulin to those cells in which all the component molecules are synthesized. The subcellular site(s) and mechanism of assembly remain to be determined, assembly of IgG heterotetramers in plants requires targeting of both proteins to the endomembrane system as has been previously shown by Hiatt, A. C., Cafferkey, R. & Bowdish, K. *Nature* 342, 76–78 (1989); and Hein, M. B., Tang, Y., McLeod, D. A., Janda, K. D. & Matt, A. C. *Biotechnol Prog.* 7, 455–461 (1991).

In addition, we have demonstrated that a protection protein derived from mature secretory component devoid of signals for membrane integration, transcytosis or subsequent proteolysis can be assembled with chimeric immunoglobulin heavy chain containing immunoglobulin gamma and alpha protein domains. These results demonstrate that the inherent functions of IgG constant regions (protein A binding, complement fixation, Fc receptor activity) may be maintained in a dimeric immunoglobulin, capable of binding to a protective protein. These additional capabilities may be employed to enhance the function of an immunoglobulin used for passive immunotherapy and the development of plants capable of generating a functional immunoglobulin containing a protection protein will have significant implications in passive immunotherapy. The level of expression of the immunoglobulin containing a protection protein is high and the production can be scaled up to agricultural proportions, to allow economical production of monoclonal antibodies.

Methods

The following methods were used to prepare and analyze the Immunoglobulin of this Example.

i) Antibody assembly in transgenic *Nicotiana tabacum.*

Leaf segments were homogenized in 150 mM NaCl 20 mM Tris-HCI (pH8) (TBS), with leupeptin (10 μg/ml). The extracts were boiled for 3 minutes, in 75 mM Tris-HCI (pH6.8), 2% SDS, under non-reducing conditions and SDS-PAGE in 4% acrylamide was performed. The gels were blotted onto nitrocellulose. The blots were incubated for 2 hrs in TBS with 0.05% Tween 20 and 1% non-fat dry milk, followed by the appropriate antiserum and incubated for 2 hrs at 37° C. After washing, the second layer alkaline phosphatase conjugated antibody was applied for 2 hrs at 37° C. Antibody binding was detected by incubation with 300 mg/ml nitroblue tetrazolium and 150 mg/ml 5-bromo-4-chloro 3-indolyl phosphate.

These extracts were analyzed using western analysis to determine whether the immunoglobulins were assembled into immunoglobulin molecules by analyzing Western blots of plant extracts prepared under non-reducing conditions, were with anti-kappa antiserum (Bradsure, UK) and an antiserum which specifically recognizes protection protein. The immunoglobulins produced in the plants were compared to the monoclonal IgG1 Guys 13 immunoglobulin described by Smith, R. & Lehner, T. *Oral Microbiol. Immunol.* 4, 153–158 (1989).

ii) Western Analysis

Western analysis was performed on each of the plant extracts prepared under reducing conditions to identify individual protein components of the immunoglobulin. Samples of the various plant extracts were prepared as described previously, but with the addition of 5% β-mercaptoethanol. SDS-PAGE in 10% acrylamide was performed and the protein in the gels transferred to nitrocellulose. Individual proteins were detected using anti-mouse γ1 heavy chain (Sigma, UK); anti-mouse kappa chain (Bradsure, UK); or an antiserum that specifically recognized the protection protein, followed by the appropriate alkaline phosphatase conjugated antibody.

iii) Western Analysis to Show Production of Immunoglobulin Having a Protection Protein Western analysis of transgenic plant extract was performed as described in ii) above. The plant extracts from plants expressing the immunoglobulin containing the protection protein were subjected to SDS-PAGE under both non-reducing and reducing conditions and the proteins transferred to nitrocellulose. The immunoglobulin components were detected with an anti-kappa antiserum or with a sheep antiserum which specifically recognized the protection protein followed by an appropriate alkaline phosphatase labeled 2° antibody.

iv) Expression of Antigen-Specific Immunoglobulin Containing a Protection Protein in transgenic *Nicotiana tabacum.*

To demonstrate that the plants were producing antigen-specific immunoglobulin, plant extract binding to purified streptococcal antigen (SA) I/II, detected with horseradish peroxidase labeled anti-kappa chain antiserum was determined. The presence of a protection protein in the antigen-specific immunoglobulin was demonstrated by plant extract binding to purified streptococcal antigen I/II and streptococcal cells detected with a sheep antiserum immunospecific for a protection protein, followed by alkaline phosphatase labeled donkey anti-sheep antiserum. These tests for antigen-specific immunoglobulin were carried out in microtitre plates that were coated with purified SA I/II (2 μg/ml) in TBS, or log phase growth Strep, *mutans* (NCTC 10449), in bicarbonate buffer (pH 9.8). Blocking was with 5% non-fat dry milk in TBS at room temperature for 2 hours. Plant leaves were homogenized in TBS with 10 μg/ml leupeptin (Calbiochem, USA). Mouse Guy's 13 hybridoma cell culture supernatant (IgG) was used as a positive control. The supernatants were added in serial two-fold dilutions to the microtitre plate and incubation was at room temperature for 2 hours. After washing with TBS with 0.05% Tween 20, bound immunoglobulin chains were detected with either a goat anti-mouse light chain specific antibody, conjugated with horseradish peroxidase (Nordic Pharmaceuticals, UK), or a sheep anti-SC antiserum, followed by an alkaline phosphatase labeled donkey anti-sheep antibody for 2 hours at room temperature. Detection was with 2.2'-azino-di-[3-ethyl-benzthiazolin-sulphonate (Boehringer, W. Germany) for HRPO conjugated antibody or disodium p-nitrophenyl phosphate (Sigma, UK) for alkaline phosphatase conjugated antibody.

v) Localization of Immunoglobulin Components in Plants

Photomicrographs of transgenic plants expressing immunoglobulins containing protection proteins and control *Nicotiana tabacum* leaf were prepared using immunogold detection of murine alpha chain. Briefly, leaf blades were cut into 2 mm×10 mm segments and fixed in 3% (w/v) paraformaldehyde, 0.5% (w/v) glutaraldehyde, 5% (w/v) sucrose in 100 mM sodium phosphate (pH 7.4). After dehydration in anhydrous ethanol, leaf segments were infiltrated with xylene, embedded in paraffin and cut into 3 mm sections and mounted on glass slides for immunochemical staining. The leaf sections were incubated with primary antibodies, affinity purified rabbit anti-mouse alpha chain (which reacts with the A/G hybrid heavy chain) or sheep anti-rabbit SC, and then with secondary antibody; goat anti-rabbit-10 mn gold or rabbit anti-sheep-10 mn gold. The immunogold signal was intensified by silver enhancement. The plants were visualized using both Phase contrast and bright field microscopy on the same leaf cross section. Immunolocalization of the protection protein on serial sections was used to show the same cellular localization for heavy chain as immunoglobulin. The analysis was carried out on the following cells and cell compartments: spongy mesophyll cells, epidermal cells, intercellular spaces, palisade parenchyma cells, and vascular bundles.

Further analysis of the exact localization of immunoglobulin components was carried out by analyzing serial sections of *Nicotiana tabacum* vascular bundle and control *Nicotiana tabacum* vascular bundle with immunogold detection for each of the components of the immunoglobulin. Serial sections of a transgenic plant leaves from plants expressing secretory immunoglobulin were incubated with an antibody that specifically recognizes the protection protein or with anti-IgA antibody followed by the appropriate gold-labeled secondary antibody. A control leaf section from a transgenic plant that did not contain any immunoglobulin coding sequences was also incubated with anti-IgA antibody, followed by gold-labeled goat anti-rabbit antiserum, or with the gold-labeled secondary antibodies alone and confirmed the specificity of staining. Both Phase contrast illumination of a minor vascular bundle and Bright field illumination of the same field were used to show immunogold localization of the protection protein. Bright field illumination of a serial leaf cross section of the vascular bundle demonstrated the same immunogold localization of the immunoglobulin heavy chain as was shown for the protection protein.

Example 8

Production of a Useful Plant Extract Containing Immunoglobulins Having a Protection Protein Plant pieces (either leaf, stem, flower, root, or combinations) from plants producing immunoglobulins containing a protection protein were mixed with homogenization buffer (2 milliliter buffer per gram of plant material; homogenization buffer: 150 mM NaCl, 20 mM Tris-Cl, pH 7.5), homogenized into a pulp using a Waring blender and centrifuged at 10,000×g to remove debris. The supernatant was then extracted with an equal volume of HPLC-grade ethyl acetate by shaking at room temperature, followed by centrifugation at 10,000×g. The aqueous phase was transferred to another container, remaining ethyl acetate was removed from the aqueous phase by placing the solution under vacuum. The resulting crude extract consistently contained 100 µg immunoglobulin having a protection protein per ml. This method is useful for any plant containing an immunoglobulin having a protection protein.

A number of methods for homogenization have been used including a mortar and pestle or a Polytron and can be performed either in the cold or at room temperature.

The extract may be further purified by delipidation, by extraction with hexane or other organic solvents. Delipidation is not essential for deriving a useful product from the plant extract but is advantageous in cases where the final product is a purified immunoglobulin having a protection protein. In many instances the crude extract will contain a sufficiently high quantity of immunoglobulin having a protection protein (i.e. 100 μg/mL) to be useful without any further purification or enrichment. For an oral application, the extract would be mixed with commonly used flavorings and stabilizers. For a dental application, the extract would in addition be mixed with a gelling reagent to maintain contact of the extract with teeth. For a gastric application, the flavored extract could be swallowed directly.

Example 9

Stability of an Immunoglobulin Containing a Protection Protein

Two sets of crude plant extracts were prepared as described above. The first extract was derived from a plant expressing an IgG1 antibody and the second extract was derived from a plant expressing an immunoglobulin containing a protection protein. Crude plant extracts of this type from plants are known to contain a variety of proteolytic enzymes. Prolonged incubation of extracts at room temperature or at 37° C. therefore constitutes a proteolytic digestion.

Using ELISA the quantity of gamma-kappa complexes in the two extracts was determined as a function of time at both room temperature and 37° C. In these assays, an anti-kappa chain antibody was used to coat the plate followed by incubation with the plant extract at 37° C. for 1 hour. An anti-gamma chain antibody conjugated to HRPO was used for detection of immunoglobulin derived from the plant. The quantity of immunoglobulin having a protection protein contained in the extract immediately after the extract was prepared was taken to be 100%. After 3 hours at room temperature, the IgG1 contained 40% and the immunoglobulin containing the protection protein contained >95%. After 6 hours, the remaining IgG1 antibody was 20% and the immunoglobulin containing the protection protein abundance was still >95%. After 12 hours, there was no detectable IgG1 whereas ~90% of the immunoglobulin containing the protection protein remained. A significant decrease (to ~70%) in the abundance of protected antibody was not observed until 48 hours after the extract was prepared.

Example 10

Eukaryotic Tetratransgenic Cells Expressing Immunoglobulins Containing Protection Protein.

The four chains comprising the immunoglobulin containing a protection protein can also be expressed in other cell types either in in vitro (cell cultures) or in vivo (transgenic animals). See, *Manipulating the Mouse Embryo; A Laboratory Manual*, B. Hogan et al., Cold Spring Harbor Laboratory (1986). In the case of transgenic animals, purified preparations of appropriate vector DNAs are adjusted to a final concentration of 2 ng/µl in 10 mM Tris, 0.2 mM EDTA, pH 7.4. Pronuclear injections are performed using zygotes prepared from inbred animals. Injected eggs are then transferred to pseudopregnant females using standard techniques. Live born animals are then screened for the presence of transgenes using any of a number of commonly used techniques such as PCR and ELISA. Members of the pedigree expressing different components of the immunoglobulin containing the protection protein are then mated to produce multi-transgene animals. Progeny from these crosses are then screened to identify those that express all four chains. Depending on the type of vector used for zygotic injections various cell types can be identified in the transgenic animals which assemble the complete immunoglobulin containing a protection protein. These vector DNAs can consist of specific promoter elements which allow transcription of the transgene in particular cell types or tissues. Each vector could express a single component of the protected antibody (IgG/A, J chain, protection protein, or kappa chain) or could potentially express more than one component. In this instance, the vector would contain an appropriate number of promoter regions and restriction sites to allow for transcription of each transgene.

Expression of all four chains in a cell culture system can be achieved using a DNA vector from which each component can be individually promoted. This would require four expression cassettes (containing promoter, multiple cloning site, and polyadenylation region) on the same vector DNA. Alternatively, individual cell lines can be sequentially transfected with individual vectors expressing single chains so long as each vector confers a selective resistance onto the cell line.

Commonly available vectors, such as pMAMneo (Clontech) can be adapted either for multiple expression or as a series of vectors expressing distinct selectable markers.

Transfection of any eukaryotic cells, such as fibroblasts, is done by conventional techniques. Briefly, cells are split 1:20 the day before transfection and are transfected at approximately 30% confluency using 125 mM CaCl2, 140 mM NaCl, 25 mM Hepes, 0.75 mM NaHPO4, pH 7.05, and 5 µg DNA/10 cm dish. After 16 hours of DNA incubation, cells are shocked by 10% dimethyl sulfoxide for 3 minutes. Forty eight hours after transfection, cells are subjected to selection by growth in the appropriate medium containing an antibiotic or other cytotoxic reagent.

The resulting cells produce all the components for the immunoglobulin containing the protection protein. These components are properly assembled to produce a functional immunoglobulin containing a protection protein.

Example 11

Engineering a Protection Protein Fused to a Portion of the Cytoplasmic Domain of the Rabbit Polyimmunoglobulin Receptor The construction of DNA segments encoding a protection protein fused to a segment encoding a segment of the cytoplasmic domain of the rabbit polyimmunoglobulin receptor is produced as follows. Protection protein cDNA encoding from the first amino acid of the signal sequence $(MET_{-18})$ to $GLU_{606}$ is ligated into any plant expression vector, such as the pMON530 vector (digested with Bgl II and Xho I) as a Bgl II-Xho I fragment. This protection protein derivative is obtained by PCR amplification using the appropriate oligonucleotide primers containing either a Bgl II or Xho I recognition sequence which are also complementary to DNA encoding residues −18 to −13 and residues 601 to 606 of the rabbit polyimmunoglobulin receptor respectively. The same procedure is performed in order to obtain a protection protein cDNA encoding from $MET_{-18}$ to $ALA_{628}$ except that the oligonucleotide containing an Xho site is also complementary to the protection protein cDNA encoding residues 623 to 628.

The cDNA encoding the rabbit polyimmunoglobulin receptor cytoplasmic domain fragment is obtained, also by PCR amplification, as a Xho I fragment. The oligonucleotides employed are complementary to DNA encoding from $ARG_{653}$ to $ALA_{755}$ both containing Xho I recognition sequences. This fragment is then ligated into the pMON530 vectors which contain the either of the protection protein cDNAs described above. The appropriate orientation of the cytoplasmic domain cDNA is determined by restriction digestions and by sequence analysis of plasmids obtained from transformed bacterial colonies.

The oligonucleotides employed for PCR amplification contain the appropriate number of nucleotides to ensure that the resulting cDNAs are in frame and capable of being translated as a continuous fusion protein containing both protection protein and cytoplasmic domain.

The resulting constructs in the appropriate orientation encode a protection protein fused directly to the polyimmunoglobulin receptor cytoplasmic domain with no functional transmembrane segment, operably linked to a DNA segment (promoter) enabling expression in a plant cell. The constructs encode two additional amino acids (SER-TRP) which are derived from introduction of the Xho I restriction site and which serve as a linker between the protection protein and the cytoplasmic domain.

These vectors are then used to transform *Agrobacterium* as previously described which in turn is used to transform plant cells. The same techniques described in the above Examples are used to produce a plant expressing this protein as part of an immunoglobulin.

We claim:

1. An isolated immunoglobulin comprising a protection protein wherein the protection protein comprises a portion of a human, rat, mouse, rabbit or bovine polyimmunoglobulin receptor as defined in Table I.

2. The immunoglobulin of claim 1 wherein said immunoglobulin is isolated from a plant.

3. An isolated immunoglobulin comprising a protection protein in association with an immunoglobulin heavy chain having at least a portion of an antigen binding domain, wherein the protection protein comprises a portion of a polyimmunoglobulin receptor as defined in Table I.

* * * * *

SEQUENCE LISTING (1) GENERAL INFORMATION:

(iii) NUMBER OF SEQUENCES: 19

(2) INFORMATION FOR SEQ ID NO: 1:

```
    (i) SEQUENCE CHARACTERISTICS:
        (A) LENGTH: 3517 base pairs
        (B) TYPE: nucleic acid
        (C) STRANDEDNESS: single
        (D) TOPOLOGY: linear
            DESCRIPTION:    Rabbit polyimmunoglobulin receptor (ix) FEATURE:
        (A) NAME/KEY: Coding Sequence
        (B) LOCATION: 124....2445

(xi) SEQUENCE DESCRIPTION: SEQ ID NO: 1:

GGCCGGGGTT ACGGGCTGGC CAGCAGGCTG TGCCCCCGAG TCCGGTCAGC AGGAGGGGAA      60

GAAGTGGCCT AAAATCTCTC CCGCATCGGC AGCCCAGGCC TAGTGCCCTA CCAGCCACCA     120

GCC ATG GCT CTC TTC TTG CTC ACC TGC CTG CTG GCT GTC TTT TCA GCG      168
    Met Ala Leu Phe Leu Leu Thr Cys Leu Leu Ala Val Phe Ser Ala
    1               5                   10                  15

GCC ACG GCA CAA AGC TCC TTA TTG GGT CCC AGC TCC ATA TTT GGT CCC      216
Ala Thr Ala Gln Ser Ser Leu Leu Gly Pro Ser Ser Ile Phe Gly Pro
                20                  25                  30

GGG GAG GTG AAT GTT TTG GAA GGC GAC TCG GTG TCC ATC ACA TGC TAC      264
Gly Glu Val Asn Val Leu Glu Gly Asp Ser Val Ser Ile Thr Cys Tyr
            35                  40                  45

TAC CCA ACA ACC TCC GTC ACC CGG CAC AGC CGG AAG TTC TGG TGC CGG      312
Tyr Pro Thr Thr Ser Val Thr Arg His Ser Arg Lys Phe Trp Cys Arg
        50                  55                  60

GAA GAG GAG AGC GGC CGC TGC GTG ACG CTT GCC TCG ACC GGC TAC ACG      360
Glu Glu Glu Ser Gly Arg Cys Val Thr Leu Ala Ser Thr Gly Tyr Thr
    65                  70                  75

TCC CAG GAA TAC TCC GGG AGA GGC AAG CTC ACC GAC TTC CCT GAT AAA      408
Ser Gln Glu Tyr Ser Gly Arg Gly Lys Leu Thr Asp Phe Pro Asp Lys
80                  85                  90                  95

GGG GAG TTT GTG GTG ACT GTT GAC CAA CTC ACC CAG AAC GAC TCA GGG      456
Gly Glu Phe Val Val Thr Val Asp Gln Leu Thr Gln Asn Asp Ser Gly
                100                 105                 110

AGC TAC AAG TGT GGC GTG GGA GTC AAC GGC CGT GGC CTG GAC TTC GGT      504
Ser Tyr Lys Cys Gly Val Gly Val Asn Gly Arg Gly Leu Asp Phe Gly
            115                 120                 125

GTC AAC GTG CTG GTC AGC CAG AAG CCA GAG CCT GAT GAC GTT GTT TAC      552
Val Asn Val Leu Val Ser Gln Lys Pro Glu Pro Asp Asp Val Val Tyr
        130                 135                 140

AAA CAA TAT GAG AGT TAT ACA GTA ACC ATC ACC TGC CCT TTC ACA TAT      600
Lys Gln Tyr Glu Ser Tyr Thr Val Thr Ile Thr Cys Pro Phe Thr Tyr
    145                 150                 155

GCG ACT AGG CAA CTA AAG AAG TCC TTT TAC AAG GTG GAA GAC GGG GAA      648
Ala Thr Arg Gln Leu Lys Lys Ser Phe Tyr Lys Val Glu Asp Gly Glu
160                 165                 170                 175

CTT GTA CTC ATC ATT GAT TCC AGC AGT AAG GAG GCA AAG GAC CCC AGG      696
Leu Val Leu Ile Ile Asp Ser Ser Ser Lys Glu Ala Lys Asp Pro Arg
                180                 185                 190

TAT AAG GGC AGA ATA ACG TTG CAG ATC CAA AGT ACC ACA GCA AAA GAA      744
Tyr Lys Gly Arg Ile Thr Leu Gln Ile Gln Ser Thr Thr Ala Lys Glu
            195                 200                 205

TTC ACA GTC ACC ATC AAG CAT TTG CAG CTC AAT GAT GCT GGG CAG TAT      792
Phe Thr Val Thr Ile Lys His Leu Gln Leu Asn Asp Ala Gly Gln Tyr
        210                 215                 220

GTC TGC CAG AGT GGA AGC GAC CCC ACT GCT GAA GAA CAG AAC GTT GAC      840
Val Cys Gln Ser Gly Ser Asp Pro Thr Ala Glu Glu Gln Asn Val Asp
    225                 230                 235

CTC CGA CTG CTA ACT CCT GGT CTG CTC TAT GGA AAC CTG GGG GGC TCG      888
```

```
                                                              -continued

Leu Arg Leu Leu Thr Pro Gly Leu Leu Tyr Gly Asn Leu Gly Gly Ser
240                 245                 250                 255

GTG ACC TTT GAA TGT GCC CTG GAC TCT GAA GAC GCA AAC GCG GTA GCA        936
Val Thr Phe Glu Cys Ala Leu Asp Ser Glu Asp Ala Asn Ala Val Ala
                    260                 265                 270

TCC TTG CGC CAG GTT AGG GGT GGC AAT GTG GTC ATT GAC AGC CAG GGG        984
Ser Leu Arg Gln Val Arg Gly Gly Asn Val Val Ile Asp Ser Gln Gly
                275                 280                 285

ACA ATA GAT CCA GCC TTC GAG GGC AGG ATC CTG TTC ACC AAG GCT GAG       1032
Thr Ile Asp Pro Ala Phe Glu Gly Arg Ile Leu Phe Thr Lys Ala Glu
            290                 295                 300

AAC GGC CAC TTC AGT GTA GTG ATC GCA GGC CTG AGG AAG GAA GAC ACA       1080
Asn Gly His Phe Ser Val Val Ile Ala Gly Leu Arg Lys Glu Asp Thr
        305                 310                 315

GGG AAC TAT CTG TGC GGA GTC CAG TCC AAT GGT CAG TCT GGG GAT GGG       1128
Gly Asn Tyr Leu Cys Gly Val Gln Ser Asn Gly Gln Ser Gly Asp Gly
320                 325                 330                 335

CCC ACC CAG CTT CGG CAA CTC TTC GTC AAT GAA GAG ATC GAC GTG TCC       1176
Pro Thr Gln Leu Arg Gln Leu Phe Val Asn Glu Glu Ile Asp Val Ser
                    340                 345                 350

CGC AGC CCC CCT GTG TTG AAG GGC TTT CCA GGA GGC TCC GTG ACC ATA       1224
Arg Ser Pro Pro Val Leu Lys Gly Phe Pro Gly Gly Ser Val Thr Ile
                355                 360                 365

CGC TGC CCC TAC AAC CCG AAG AGA AGC GAC AGC CAC CTG CAG CTG TAT       1272
Arg Cys Pro Tyr Asn Pro Lys Arg Ser Asp Ser His Leu Gln Leu Tyr
            370                 375                 380

CTC TGG GAA GGG AGT CAA ACC CGC CAT CTG CTG GTG GAC AGC GGC GAG       1320
Leu Trp Glu Gly Ser Gln Thr Arg His Leu Leu Val Asp Ser Gly Glu
385                 390                 395

GGG CTG GTT CAG AAA GAC TAC ACA GGC AGG CTG GCC CTG TTC GAA GAG       1368
Gly Leu Val Gln Lys Asp Tyr Thr Gly Arg Leu Ala Leu Phe Glu Glu
400                 405                 410                 415

CCT GGC AAT GGC ACC TTC TCA GTC GTC CTC AAC CAG CTC ACT GCC GAG       1416
Pro Gly Asn Gly Thr Phe Ser Val Val Leu Asn Gln Leu Thr Ala Glu
                    420                 425                 430

GAT GAA GGC TTC TAC TGG TGT GTC AGC GAT GAC GAT GAG TCC CTG ACG       1464
Asp Glu Gly Phe Tyr Trp Cys Val Ser Asp Asp Asp Glu Ser Leu Thr
                435                 440                 445

ACT TCG GTG AAG CTC CAG ATC GTT GAC GGA GAA CCA AGC CCC ACG ATC       1512
Thr Ser Val Lys Leu Gln Ile Val Asp Gly Glu Pro Ser Pro Thr Ile
            450                 455                 460

GAC AAG TTC ACT GCT GTG CAG GGA GAG CCT GTT GAG ATC ACC TGC CAC       1560
Asp Lys Phe Thr Ala Val Gln Gly Glu Pro Val Glu Ile Thr Cys His
465                 470                 475

TTC CCA TGC AAA TAC TTC TCC TCC GAG AAG TAC TGG TGC AAG TGG AAT       1608
Phe Pro Cys Lys Tyr Phe Ser Ser Glu Lys Tyr Trp Cys Lys Trp Asn
480                 485                 490                 495

GAC CAT GGC TGC GAG GAC CTG CCC ACT AAG CTC AGC TCC AGC GGC GAC       1656
Asp His Gly Cys Glu Asp Leu Pro Thr Lys Leu Ser Ser Ser Gly Asp
                    500                 505                 510

CTT GTG AAA TGC AAC AAC AAC CTG GTC CTC ACC CTG ACC TTG GAC TCG       1704
Leu Val Lys Cys Asn Asn Asn Leu Val Leu Thr Leu Thr Leu Asp Ser
                515                 520                 525

GTC AGC GAA GAT GAC GAG GGC TGG TAC TGG TGT GGC GCG AAA GAC GGG       1752
Val Ser Glu Asp Asp Glu Gly Trp Tyr Trp Cys Gly Ala Lys Asp Gly
            530                 535                 540

CAC GAG TTT GAA GAG GTT GCG GCC GTC AGG GTG GAG CTG ACA GAG CCA       1800
His Glu Phe Glu Glu Val Ala Ala Val Arg Val Glu Leu Thr Glu Pro
545                 550                 555
```

```
GCC AAG GTA GCT GTC GAG CCA GCC AAG GTA CCT GTC GAC CCA GCC AAG          1848
Ala Lys Val Ala Val Glu Pro Ala Lys Val Pro Val Asp Pro Ala Lys
560             565             570             575

GCA GCC CCC GCG CCT GCT GAG GAG AAG GCC AAG GCG CGG TGC CCA GTG          1896
Ala Ala Pro Ala Pro Ala Glu Glu Lys Ala Lys Ala Arg Cys Pro Val
            580             585             590

CCC AGG AGA AGG CAG TGG TAC CCA TTG TCA AGG AAG CTG AGA ACA AGT          1944
Pro Arg Arg Arg Gln Trp Tyr Pro Leu Ser Arg Lys Leu Arg Thr Ser
        595             600             605

TGT CCA GAA CCT CGG CTC CTT GCG GAG GAG GTA GCA GTG CAG AGT GCG          1992
Cys Pro Glu Pro Arg Leu Leu Ala Glu Glu Val Ala Val Gln Ser Ala
    610             615             620

GAA GAC CCA GCC AGT GGG AGC AGA GCG TCT GTG GAT GCC AGC AGT GCT          2040
Glu Asp Pro Ala Ser Gly Ser Arg Ala Ser Val Asp Ala Ser Ser Ala
625             630             635

TCG GGA CAA AGC GGG AGT GCC AAA GTA CTG ATC TCC ACC CTG GTG CCC          2088
Ser Gly Gln Ser Gly Ser Ala Lys Val Leu Ile Ser Thr Leu Val Pro
640             645             650             655

TTG GGG CTG GTG CTG GCA GCG GGG GCC ATG GCC GTG GCC ATA GCC AGA          2136
Leu Gly Leu Val Leu Ala Ala Gly Ala Met Ala Val Ala Ile Ala Arg
            660             665             670

GCC CGG CAC AGG AGG AAC GTG GAC CGA GTT TCC ATC GGA AGC TAC AGG          2184
Ala Arg His Arg Arg Asn Val Asp Arg Val Ser Ile Gly Ser Tyr Arg
        675             680             685

ACA GAC ATT AGC ATG TCA GAC TTG GAG AAC TCC AGG GAG TTC GGA GCC          2232
Thr Asp Ile Ser Met Ser Asp Leu Glu Asn Ser Arg Glu Phe Gly Ala
    690             695             700

ATT GAC AAC CCA AGC GCC TGC CCC GAT GCC CGG GAG ACG GCC CTC GGA          2280
Ile Asp Asn Pro Ser Ala Cys Pro Asp Ala Arg Glu Thr Ala Leu Gly
705             710             715

GGA AAG GAT GAG TTA GCG ACG GCC ACC GAG AGC ACC GTG GAG ATT GAG          2328
Gly Lys Asp Glu Leu Ala Thr Ala Thr Glu Ser Thr Val Glu Ile Glu
720             725             730             735

GAG CCC AAG AAG GCA AAA CGG TCA TCC AAG GAA GAA GCC GAC CTG GCC          2376
Glu Pro Lys Lys Ala Lys Arg Ser Ser Lys Glu Glu Ala Asp Leu Ala
            740             745             750

TAC TCA GCT TTC CTG CTC CAA TCC AAC ACC ATA GCT GCT GAG CAC CAA          2424
Tyr Ser Ala Phe Leu Leu Gln Ser Asn Thr Ile Ala Ala Glu His Gln
        755             760             765

GAT GGC CCC AAG GAG GCC TAG GCACAGCCGG CCACCGCCGC CGCCGCCACC GCCGC        2480
Asp Gly Pro Lys Glu Ala
            770

CGCCGCCGCC ACCTGTGAAA ATCACCTTCC AGAATCACGT TGATCCTCGG GGTCCCCAGA        2540

GCCGGGGGCT CAACCGCCCT GCACCCCCCA TGTCCCCACC ACCTAAACTT CCCTACCTGT        2600

GCCCAGAGGT GTGCTGGTCC CCTCCTCCAC GGCATCCAGG CCTGGCTCAA TGTTCCCGTT        2660

GGGGTGGGGG TGTGAGGGGT TCCTACTTGC AGCCCGGTTC TCCCGAGAGA AGCTAAGGAT        2720

CCAGGTCCTG AGGGAGGGGC CTCTCGAAGG CAGACAGACC AGAGAGGGGG GAGGAGCCCT        2780

TGGATGGGAG GCCAGAGGCG CTTTCCGGCC ACCCCCTCCC TCCCTGCCCC CACCCTCCTT        2840

CCTTCATTCA AAAGTCCCAG TGGCTGCTGC CTAGGGTCCA GGCGCTGGCC GCACGCCTCC        2900

TCGAAGCCGT TGTGCAAACA TCACTGGAGG AAGCCAGGGC TCCTCCCGGG CTGTGTATCC        2960

TCACTCAGGC ATCCTGTCCT CCCCAGTATC AGGAGATGTC AAGCGTCTGA AGGCTGTGTG        3020

CCCTGGGCGT GTCTGCAAGT CACCCCAGAC ACATGTTCTC GCCATTTTAC AGATGAGAAC        3080

ACTGAGGTTG TACTCAAGGG CACCCTGCGA GATGGAGCAA CAGCAAACTA GATGGGCTTC        3140

TGCTGTCCTC TTGGCCAGAG GTCTCTCCAC AGGAGCCCCT GCCCCTGTAG AAGCAGAGT         3200
```

-continued

```
TTTAGAACAT GGAAGAAGAA GAGGGGGATG GCCCTGGACG CTGACCTCTC CCAAGCCCCC    3260

ACGGGGGAAA AGGCCCCCTC CTTTTCTGTC ACTCTCGGGG ACCTGCGGAG TTGAGCATTC    3320

GTGCCCCGTG TGTCTGAAGA GTTCCCAGTG GAAAGAAGAA AAGAGGGTGT TTGTCAGTGC    3380

CGGGGAGGGC CTGATCCCCA GACAGCTGAA GTTTAAGGTC CTTGTCCCTG TGAGCTTTAA    3440

CCAGCACCTC CGGGCTGACC CTTGCTAACA CATCAGAAAT GTGATTTAAT CATTAAACAT    3500

TGTGATTGCC ACTGGGA                                                   3517
```

(2) INFORMATION FOR SEQ ID NO: 2:

(i) SEQUENCE CHARACTERISTICS:
        (A) LENGTH: 773 amino acids
        (B) TYPE: amino acid
        (C) STRANDEDNESS: single
        (D) TOPOLOGY: linear
            DESCRIPTION:    Rabbit polyimmunoglobulin receptor (xi) SEQUENCE DESCRIPTION: SEQ ID NO: 2:

```
Met Ala Leu Phe Leu Leu Thr Cys Leu Leu Ala Val Phe Ser Ala Ala
1               5                   10                  15

Thr Ala Gln Ser Ser Leu Leu Gly Pro Ser Ser Ile Phe Gly Pro Gly
            20                  25                  30

Glu Val Asn Val Leu Glu Gly Asp Ser Val Ser Ile Thr Cys Tyr Tyr
        35                  40                  45

Pro Thr Thr Ser Val Thr Arg His Ser Arg Lys Phe Trp Cys Arg Glu
50                  55                  60

Glu Ser Gly Arg Cys Val Thr Leu Ala Ser Thr Gly Tyr Thr Ser
65                  70                  75                  80

Gln Glu Tyr Ser Gly Arg Gly Lys Leu Thr Asp Phe Pro Asp Lys Gly
                85                  90                  95

Glu Phe Val Val Thr Val Asp Gln Leu Thr Gln Asn Asp Ser Gly Ser
            100                 105                 110

Tyr Lys Cys Gly Val Gly Val Asn Gly Arg Gly Leu Asp Phe Gly Val
        115                 120                 125

Asn Val Leu Val Ser Gln Lys Pro Glu Pro Asp Asp Val Val Tyr Lys
130                 135                 140

Gln Tyr Glu Ser Tyr Thr Val Thr Ile Thr Cys Pro Phe Thr Tyr Ala
145                 150                 155                 160

Thr Arg Gln Leu Lys Lys Ser Phe Tyr Lys Val Glu Asp Gly Glu Leu
                165                 170                 175

Val Leu Ile Ile Asp Ser Ser Lys Glu Ala Lys Asp Pro Arg Tyr
            180                 185                 190

Lys Gly Arg Ile Thr Leu Gln Ile Gln Ser Thr Thr Ala Lys Glu Phe
        195                 200                 205

Thr Val Thr Ile Lys His Leu Gln Leu Asn Asp Ala Gly Gln Tyr Val
    210                 215                 220

Cys Gln Ser Gly Ser Asp Pro Thr Ala Glu Glu Gln Asn Val Asp Leu
225                 230                 235                 240

Arg Leu Leu Thr Pro Gly Leu Leu Tyr Gly Asn Leu Gly Gly Ser Val
                245                 250                 255

Thr Phe Glu Cys Ala Leu Asp Ser Glu Asp Ala Asn Ala Val Ala Ser
            260                 265                 270

Leu Arg Gln Val Arg Gly Gly Asn Val Val Ile Asp Ser Gln Gly Thr
        275                 280                 285
```

-continued

```
Ile Asp Pro Ala Phe Glu Gly Arg Ile Leu Phe Thr Lys Ala Glu Asn
    290                 295                 300

Gly His Phe Ser Val Val Ile Ala Gly Leu Arg Lys Glu Asp Thr Gly
305                 310                 315                 320

Asn Tyr Leu Cys Gly Val Gln Ser Asn Gly Gln Ser Gly Asp Gly Pro
                325                 330                 335

Thr Gln Leu Arg Gln Leu Phe Val Asn Glu Glu Ile Asp Val Ser Arg
                340                 345                 350

Ser Pro Pro Val Leu Lys Gly Phe Pro Gly Gly Ser Val Thr Ile Arg
            355                 360                 365

Cys Pro Tyr Asn Pro Lys Arg Ser Asp Ser His Leu Gln Leu Tyr Leu
    370                 375                 380

Trp Glu Gly Ser Gln Thr Arg His Leu Leu Val Asp Ser Gly Glu Gly
385                 390                 395                 400

Leu Val Gln Lys Asp Tyr Thr Gly Arg Leu Ala Leu Phe Glu Glu Pro
                405                 410                 415

Gly Asn Gly Thr Phe Ser Val Val Leu Asn Gln Leu Thr Ala Glu Asp
                420                 425                 430

Glu Gly Phe Tyr Trp Cys Val Ser Asp Asp Glu Ser Leu Thr Thr
                435                 440                 445

Ser Val Lys Leu Gln Ile Val Asp Gly Glu Pro Ser Pro Thr Ile Asp
450                 455                 460

Lys Phe Thr Ala Val Gln Gly Glu Pro Val Glu Ile Thr Cys His Phe
465                 470                 475                 480

Pro Cys Lys Tyr Phe Ser Ser Glu Lys Tyr Trp Cys Lys Trp Asn Asp
                485                 490                 495

His Gly Cys Glu Asp Leu Pro Thr Lys Leu Ser Ser Ser Gly Asp Leu
                500                 505                 510

Val Lys Cys Asn Asn Asn Leu Val Leu Thr Leu Thr Leu Asp Ser Val
        515                 520                 525

Ser Glu Asp Asp Glu Gly Trp Tyr Trp Cys Gly Ala Lys Asp Gly His
    530                 535                 540

Glu Phe Glu Glu Val Ala Val Arg Val Glu Leu Thr Glu Pro Ala
545                 550                 555                 560

Lys Val Ala Val Glu Pro Ala Lys Val Pro Val Asp Pro Ala Lys Ala
                565                 570                 575

Ala Pro Ala Pro Ala Glu Glu Lys Ala Lys Ala Arg Cys Pro Val Pro
            580                 585                 590

Arg Arg Arg Gln Trp Tyr Pro Leu Ser Arg Lys Leu Arg Thr Ser Cys
    595                 600                 605

Pro Glu Pro Arg Leu Leu Ala Glu Glu Val Ala Val Gln Ser Ala Glu
    610                 615                 620

Asp Pro Ala Ser Gly Ser Arg Ala Ser Val Asp Ala Ser Ser Ala Ser
625                 630                 635                 640

Gly Gln Ser Gly Ser Ala Lys Val Leu Ile Ser Thr Leu Val Pro Leu
                645                 650                 655

Gly Leu Val Leu Ala Ala Gly Ala Met Ala Val Ala Ile Ala Arg Ala
            660                 665                 670

Arg His Arg Arg Asn Val Asp Arg Val Ser Ile Gly Ser Tyr Arg Thr
        675                 680                 685

Asp Ile Ser Met Ser Asp Leu Glu Asn Ser Arg Glu Phe Gly Ala Ile
    690                 695                 700

Asp Asn Pro Ser Ala Cys Pro Asp Ala Arg Glu Thr Ala Leu Gly Gly
```

-continued

```
          705                 710                 715                 720
Lys Asp Glu Leu Ala Thr Ala Thr Glu Ser Thr Val Glu Ile Glu Glu
                    725                 730                 735

Pro Lys Lys Ala Lys Arg Ser Ser Lys Glu Glu Ala Asp Leu Ala Tyr
            740                 745                 750

Ser Ala Phe Leu Leu Gln Ser Asn Thr Ile Ala Ala Glu His Gln Asp
                755                 760                 765

Gly Pro Lys Glu Ala
        770
```

(2) INFORMATION FOR SEQ ID NO: 3:

(i) SEQUENCE CHARACTERISTICS:
        (A) LENGTH: 2919 base pairs
        (B) TYPE: nucleic acid
        (C) STRANDEDNESS: single
        (D) TOPOLOGY: linear
            DESCRIPTION:    Human polyimmunoglobulin Receptor (ix) FEATURE:
        (A) NAME/KEY: Coding Sequence
        (B) LOCATION: 235....2472

(xi) SEQUENCE DESCRIPTION: SEQ ID NO: 3:

```
AGAGTTTCAG TTTTGGCAGC AGCGTCCAGT GCCCTGCCAG TAGCTCCTAG AGAGGCAGGG      60

GTTACCAACT GGCCAGCAGG CTGTGTCCCT GAAGTCAGAT CAACGGGAGA GAAGGAAGTG     120

GCTAAAACAT TGCACAGGAG AAGTCGGCCT GAGTGGTGCG GCGCTCGGGA CCCACCAGCA     180

ATGCTGCTCT TCGTGCTCAC CTGCCTGCTG GCGGTCTTCC CAGCCATCTC CACG AAG      237
                                                            Lys
                                                              1

AGT CCC ATA TTT GGT CCC GAG GAG GTG AAT AGT GTG GAA GGT AAC TCA      285
Ser Pro Ile Phe Gly Pro Glu Glu Val Asn Ser Val Glu Gly Asn Ser
            5                  10                  15

GTG TCC ATC ACG TGC TAC TAC CCA CCC ACC TCT GTC AAC CGG CAC ACC      333
Val Ser Ile Thr Cys Tyr Tyr Pro Pro Thr Ser Val Asn Arg His Thr
         20                  25                  30

CGG AAG TAC TGG TGC CGG CAG GGA GCT AGA GGT GGC TGC ATA ACC CTC      381
Arg Lys Tyr Trp Cys Arg Gln Gly Ala Arg Gly Gly Cys Ile Thr Leu
 35                  40                  45

ATC TCC TCG GAG GGC TAC GTC TCC AGC AAA TAT GCA GGC AGG GCT AAC      429
Ile Ser Ser Glu Gly Tyr Val Ser Ser Lys Tyr Ala Gly Arg Ala Asn
 50                  55                  60                  65

CTC ACC AAC TTC CCG GAG AAC GGC ACA TTT GTG GTG AAC ATT GCC CAG      477
Leu Thr Asn Phe Pro Glu Asn Gly Thr Phe Val Val Asn Ile Ala Gln
             70                  75                  80

CTG AGC CAG GAT GAC TCC GGG CGC TAC AAG TGT GGC CTG GGC ATC AAT      525
Leu Ser Gln Asp Asp Ser Gly Arg Tyr Lys Cys Gly Leu Gly Ile Asn
         85                  90                  95

AGC CGA GGC CTG TCC TTT GAT GTC AGC CTG GAG GTC AGC CAG GGT CCT      573
Ser Arg Gly Leu Ser Phe Asp Val Ser Leu Glu Val Ser Gln Gly Pro
            100                 105                 110

GGG CTC CTA AAT GAC ACT AAA GTC TAC ACA GTG GAC CTG GGC AGA ACG      621
Gly Leu Leu Asn Asp Thr Lys Val Tyr Thr Val Asp Leu Gly Arg Thr
115                 120                 125

GTG ACC ATC AAC TGC CCT TTC AAG ACT GAG AAT GCT CAA AAG AGG AAG      669
Val Thr Ile Asn Cys Pro Phe Lys Thr Glu Asn Ala Gln Lys Arg Lys
130                 135                 140                 145

TCC TTG TAC AAG CAG ATA GGC CTG TAC CCT GTG CTG GTC ATC GAC TCC      717
Ser Leu Tyr Lys Gln Ile Gly Leu Tyr Pro Val Leu Val Ile Asp Ser
            150                 155                 160
```

```
AGT GGT TAT GTG AAT CCC AAC TAT ACA GGA AGA ATA CGC CTT GAT ATT        765
Ser Gly Tyr Val Asn Pro Asn Tyr Thr Gly Arg Ile Arg Leu Asp Ile
            165                 170                 175

CAG GGT ACT GGC CAG TTA CTG TTC AGC GTT GTC ATC AAC CAA CTC AGG        813
Gln Gly Thr Gly Gln Leu Leu Phe Ser Val Val Ile Asn Gln Leu Arg
        180                 185                 190

CTC AGC GAT GCT GGG CAG TAT CTC TGC CAG GCT GGG GAT GAT TCC AAT        861
Leu Ser Asp Ala Gly Gln Tyr Leu Cys Gln Ala Gly Asp Asp Ser Asn
    195                 200                 205

AGT AAT AAG AAG AAT GCT GAC CTC CAA GTG CTA AAG CCC GAG CCC GAG        909
Ser Asn Lys Lys Asn Ala Asp Leu Gln Val Leu Lys Pro Glu Pro Glu
210                 215                 220                 225

CTG GTT TAT GAA GAC CTG AGG GGC TCA GTG ACC TTC CAC TGT GCC CTG        957
Leu Val Tyr Glu Asp Leu Arg Gly Ser Val Thr Phe His Cys Ala Leu
                230                 235                 240

GGC CCT GAG GTG GCA AAC GTG GCC AAA TTT CTG TGC CGA CAG AGC AGT       1005
Gly Pro Glu Val Ala Asn Val Ala Lys Phe Leu Cys Arg Gln Ser Ser
            245                 250                 255

GGG GAA AAC TGT GAC GTG GTC GTC AAC ACC CTG GGG AAG AGG GCC CCA       1053
Gly Glu Asn Cys Asp Val Val Val Asn Thr Leu Gly Lys Arg Ala Pro
        260                 265                 270

GCC TTT GAG GGC AGG ATC CTG CTC AAC CCC CAG GAC AAG GAT GGC TCA       1101
Ala Phe Glu Gly Arg Ile Leu Leu Asn Pro Gln Asp Lys Asp Gly Ser
    275                 280                 285

TTC AGT GTG GTG ATC ACA GGC CTG AGG AAG GAG GAT GCA GGG CGC TAC       1149
Phe Ser Val Val Ile Thr Gly Leu Arg Lys Glu Asp Ala Gly Arg Tyr
290                 295                 300                 305

CTG TGT GGA GCC CAT TCG GAT GGT CAG CTG CAG GAA GGC TCG CCT ATC       1197
Leu Cys Gly Ala His Ser Asp Gly Gln Leu Gln Glu Gly Ser Pro Ile
                310                 315                 320

CAG GCC TGG CAA CTC TTC GTC AAT GAG GAG TCC ACG ATT CCC CGC AGC       1245
Gln Ala Trp Gln Leu Phe Val Asn Glu Glu Ser Thr Ile Pro Arg Ser
            325                 330                 335

CCC ACT GTG GTG AAG GGG GTG GCA GGA AGC TCT GTG GCC GTG CTC TGC       1293
Pro Thr Val Val Lys Gly Val Ala Gly Ser Ser Val Ala Val Leu Cys
        340                 345                 350

CCC TAC AAC CGT AAG GAA AGC AAA AGC ATC AAG TAC TGG TGT CTC TGG       1341
Pro Tyr Asn Arg Lys Glu Ser Lys Ser Ile Lys Tyr Trp Cys Leu Trp
    355                 360                 365

GAA GGG GCC CAG AAT GGC CGC TGC CCC CTG CTG GTG GAC AGC GAG GGG       1389
Glu Gly Ala Gln Asn Gly Arg Cys Pro Leu Leu Val Asp Ser Glu Gly
370                 375                 380                 385

TGG GTT AAG GCC CAG TAC GAG GGC CGC CTC TCC CTG CTG GAG GAG CCA       1437
Trp Val Lys Ala Gln Tyr Glu Gly Arg Leu Ser Leu Leu Glu Glu Pro
                390                 395                 400

GGC AAC GGC ACC TTC ACT GTC ATC CTC AAC CAG CTC ACC AGC CGG GAC       1485
Gly Asn Gly Thr Phe Thr Val Ile Leu Asn Gln Leu Thr Ser Arg Asp
            405                 410                 415

GCC GGC TTC TAC TGG TGT CTG ACC AAC GGC GAT ACT CTC TGG AGG ACC       1533
Ala Gly Phe Tyr Trp Cys Leu Thr Asn Gly Asp Thr Leu Trp Arg Thr
        420                 425                 430

ACC GTG GAG ATC AAG ATT ATC GAA GGA GAA CCA AAC CTC AAG GTA CCA       1581
Thr Val Glu Ile Lys Ile Ile Glu Gly Glu Pro Asn Leu Lys Val Pro
    435                 440                 445

GGG AAT GTC ACG GCT GTG CTG GGA GAG ACT CTC AAG GTC CCC TGT CAC       1629
Gly Asn Val Thr Ala Val Leu Gly Glu Thr Leu Lys Val Pro Cys His
450                 455                 460                 465

TTT CCA TGC AAA TTC TCC TCG TAC GAG AAA TAC TGG TGC AAG TGG AAT       1677
Phe Pro Cys Lys Phe Ser Ser Tyr Glu Lys Tyr Trp Cys Lys Trp Asn
```

```
                    470             475             480
AAC ACG GGC TGC CAG GCC CTG CCC AGC CAA GAC GAA GGC CCC AGC AAG   1725
Asn Thr Gly Cys Gln Ala Leu Pro Ser Gln Asp Glu Gly Pro Ser Lys
            485                 490                 495

GCC TTC GTG AAC TGT GAC GAG AAC AGC CGG CTT GTC TCC CTG ACC CTG   1773
Ala Phe Val Asn Cys Asp Glu Asn Ser Arg Leu Val Ser Leu Thr Leu
            500                 505                 510

AAC CTG GTG ACC AGG GCT GAT GAG GGC TGG TAC TGG TGT GGA GTG AAG   1821
Asn Leu Val Thr Arg Ala Asp Glu Gly Trp Tyr Trp Cys Gly Val Lys
            515                 520                 525

CAG GGC CAC TTC TAT GGA GAG ACT GCA GCC GTC TAT GTG GCA GTT GAA   1869
Gln Gly His Phe Tyr Gly Glu Thr Ala Ala Val Tyr Val Ala Val Glu
530                 535                 540                 545

GAG AGG AAG GCA GCG GGG TCC CGC GAT GTC AGC CTA GCG AAG GCA GAC   1917
Glu Arg Lys Ala Ala Gly Ser Arg Asp Val Ser Leu Ala Lys Ala Asp
                550                 555                 560

GCT GCT CCT GAT GAG AAG GTG CTA GAC TCT GGT TTT CGG GAG ATT GAG   1965
Ala Ala Pro Asp Glu Lys Val Leu Asp Ser Gly Phe Arg Glu Ile Glu
                565                 570                 575

AAC AAA GCC ATT CAG GAT CCC AGG CTT TTT GCA GAG GAA AAG GCG GTG   2013
Asn Lys Ala Ile Gln Asp Pro Arg Leu Phe Ala Glu Glu Lys Ala Val
            580                 585                 590

GCA GAT ACA AGA GAT CAA GCC GAT GGG AGC AGA GCA TCT GTG GAT TCC   2061
Ala Asp Thr Arg Asp Gln Ala Asp Gly Ser Arg Ala Ser Val Asp Ser
595                 600                 605

GGC AGC TCT GAG GAA CAA GGT GGA AGC TCC AGA GCG CTG GTC TCC ACC   2109
Gly Ser Ser Glu Glu Gln Gly Gly Ser Ser Arg Ala Leu Val Ser Thr
610                 615                 620                 625

CTG GTG CCC CTG GGC CTG GTG CTG GCA GTG GGA GCC GTG GCT GTG GGG   2157
Leu Val Pro Leu Gly Leu Val Leu Ala Val Gly Ala Val Ala Val Gly
                630                 635                 640

GTG GCC AGA GCC CGG CAC AGG AAG AAC GTC GAC CGA GTT TCA ATC AGA   2205
Val Ala Arg Ala Arg His Arg Lys Asn Val Asp Arg Val Ser Ile Arg
            645                 650                 655

AGC TAC AGG ACA GAC ATT AGC ATG TCA GAC TTC GAG AAC TCC AGG GAA   2253
Ser Tyr Arg Thr Asp Ile Ser Met Ser Asp Phe Glu Asn Ser Arg Glu
            660                 665                 670

TTT GGA GCC AAT GAC AAC ATG GGA GCC TCT TCG ATC ACT CAG GAG ACA   2301
Phe Gly Ala Asn Asp Asn Met Gly Ala Ser Ser Ile Thr Gln Glu Thr
675                 680                 685

TCC CTC GGA GGA AAA GAA GAG TTT GTT GCC ACC ACT GAG AGC ACC ACA   2349
Ser Leu Gly Gly Lys Glu Glu Phe Val Ala Thr Thr Glu Ser Thr Thr
690                 695                 700                 705

GAG ACC AAA GAA CCC AAG AAG GCA AAA AGG TCA TCC AAG GAG GAA GCC   2397
Glu Thr Lys Glu Pro Lys Lys Ala Lys Arg Ser Ser Lys Glu Glu Ala
                710                 715                 720

GAG ATG GCC TAC AAA GAC TTC CTG CTC CAG TCC AGC ACC GTG GCC GCC   2445
Glu Met Ala Tyr Lys Asp Phe Leu Leu Gln Ser Ser Thr Val Ala Ala
                725                 730                 735

GAG GCC CAG GAC GGC CCC CAG GAA GCC TAGACGGTGT CGCCGCCTGC TCCCTGCA   2500
Glu Ala Gln Asp Gly Pro Gln Glu Ala
                740                 745

CCCATGACAA TCACCTTCAG AATCATGTCG ATCCTGGGGG CCCTCAGCTC CTGGGGACCC    2560

CACTCCCTGC TCTAACACCT GCCTAGGTTT TTCCTACTGT CCTCAGAGGC GTGCTGGTCC    2620

CCTCCTCAGT GACATCAAAG CCTGGCCTAA TTGTTCCTAT TGGGGATGAG GGTGGCATGA    2680

GGAGGTCCCA CTTGCAACTT CTTTCTGTTG AGAGAACCTC AGGTACGGAG AAGAATAGAG    2740

GTCCTCATGG GTCCCTTGAA GGAAGAGGGA CCAGGGTGGG AGAGCTGATT GCAGAAAGGA    2800
```

-continued

```
GAGACGTGCA GCGCCCCTCT GCACCCTTAT CATGGGATGT CAACAGAATT TTTTCCCTCC    2860

ACTCCATCCC TCCCTCCCGT CCTTCCCCTC TTCTTCTTTC CTTACCATCA AAAGATGTA     2919
```

(2) INFORMATION FOR SEQ ID NO: 4:

(i) SEQUENCE CHARACTERISTICS:
        (A) LENGTH: 746 amino acids
        (B) TYPE: amino acid
        (C) STRANDEDNESS: single
        (D) TOPOLOGY: linear
            DESCRIPTION: Human Polyimmunoglbulin Receptor (xi) SEQUENCE DESCRIPTION: SEQ ID NO: 4:

```
Lys Ser Pro Ile Phe Gly Pro Glu Glu Val Asn Ser Val Glu Gly Asn
 1               5                  10                  15

Ser Val Ser Ile Thr Cys Tyr Tyr Pro Pro Thr Ser Val Asn Arg His
             20                  25                  30

Thr Arg Lys Tyr Trp Cys Arg Gln Gly Ala Arg Gly Gly Cys Ile Thr
         35                  40                  45

Leu Ile Ser Ser Glu Gly Tyr Val Ser Lys Tyr Ala Gly Arg Ala
 50                  55                  60

Asn Leu Thr Asn Phe Pro Glu Asn Gly Thr Phe Val Val Asn Ile Ala
 65                  70                  75                  80

Gln Leu Ser Gln Asp Asp Ser Gly Arg Tyr Lys Cys Gly Leu Gly Ile
                 85                  90                  95

Asn Ser Arg Gly Leu Ser Phe Asp Val Ser Leu Glu Val Ser Gln Gly
            100                 105                 110

Pro Gly Leu Leu Asn Asp Thr Lys Val Tyr Thr Val Asp Leu Gly Arg
        115                 120                 125

Thr Val Thr Ile Asn Cys Pro Phe Lys Thr Glu Asn Ala Gln Lys Arg
130                 135                 140

Lys Ser Leu Tyr Lys Gln Ile Gly Leu Tyr Pro Val Leu Val Ile Asp
145                 150                 155                 160

Ser Ser Gly Tyr Val Asn Pro Asn Tyr Thr Gly Arg Ile Arg Leu Asp
                165                 170                 175

Ile Gln Gly Thr Gly Gln Leu Leu Phe Ser Val Val Ile Asn Gln Leu
            180                 185                 190

Arg Leu Ser Asp Ala Gly Gln Tyr Leu Cys Gln Ala Gly Asp Asp Ser
        195                 200                 205

Asn Ser Asn Lys Lys Asn Ala Asp Leu Gln Val Leu Lys Pro Glu Pro
210                 215                 220

Glu Leu Val Tyr Glu Asp Leu Arg Gly Ser Val Thr Phe His Cys Ala
225                 230                 235                 240

Leu Gly Pro Glu Val Ala Asn Val Ala Lys Phe Leu Cys Arg Gln Ser
                245                 250                 255

Ser Gly Glu Asn Cys Asp Val Val Asn Thr Leu Gly Lys Arg Ala
            260                 265                 270

Pro Ala Phe Glu Gly Arg Ile Leu Leu Asn Pro Gln Asp Lys Asp Gly
        275                 280                 285

Ser Phe Ser Val Val Ile Thr Gly Leu Arg Lys Glu Asp Ala Gly Arg
290                 295                 300

Tyr Leu Cys Gly Ala His Ser Asp Gly Gln Leu Gln Glu Gly Ser Pro
305                 310                 315                 320

Ile Gln Ala Trp Gln Leu Phe Val Asn Glu Glu Ser Thr Ile Pro Arg
                325                 330                 335
```

-continued

```
Ser Pro Thr Val Val Lys Gly Val Ala Gly Ser Ser Val Ala Val Leu
            340                 345                 350

Cys Pro Tyr Asn Arg Lys Glu Ser Lys Ser Ile Lys Tyr Trp Cys Leu
            355                 360                 365

Trp Glu Gly Ala Gln Asn Gly Arg Cys Pro Leu Leu Val Asp Ser Glu
            370                 375                 380

Gly Trp Val Lys Ala Gln Tyr Glu Gly Arg Leu Ser Leu Leu Glu Glu
385                 390                 395                 400

Pro Gly Asn Gly Thr Phe Thr Val Ile Leu Asn Gln Leu Thr Ser Arg
                405                 410                 415

Asp Ala Gly Phe Tyr Trp Cys Leu Thr Asn Gly Asp Thr Leu Trp Arg
                420                 425                 430

Thr Thr Val Glu Ile Lys Ile Ile Glu Gly Glu Pro Asn Leu Lys Val
            435                 440                 445

Pro Gly Asn Val Thr Ala Val Leu Gly Glu Thr Leu Lys Val Pro Cys
            450                 455                 460

His Phe Pro Cys Lys Phe Ser Ser Tyr Glu Lys Tyr Trp Cys Lys Trp
465                 470                 475                 480

Asn Asn Thr Gly Cys Gln Ala Leu Pro Ser Gln Asp Glu Gly Pro Ser
                485                 490                 495

Lys Ala Phe Val Asn Cys Asp Glu Asn Ser Arg Leu Val Ser Leu Thr
                500                 505                 510

Leu Asn Leu Val Thr Arg Ala Asp Glu Gly Trp Tyr Trp Cys Gly Val
            515                 520                 525

Lys Gln Gly His Phe Tyr Gly Glu Thr Ala Ala Val Tyr Val Ala Val
            530                 535                 540

Glu Glu Arg Lys Ala Ala Gly Ser Arg Asp Val Ser Leu Ala Lys Ala
545                 550                 555                 560

Asp Ala Ala Pro Asp Glu Lys Val Leu Asp Ser Gly Phe Arg Glu Ile
                565                 570                 575

Glu Asn Lys Ala Ile Gln Asp Pro Arg Leu Phe Ala Glu Lys Ala
                580                 585                 590

Val Ala Asp Thr Arg Asp Gln Ala Asp Gly Ser Arg Ala Ser Val Asp
            595                 600                 605

Ser Gly Ser Ser Glu Glu Gln Gly Gly Ser Ser Arg Ala Leu Val Ser
            610                 615                 620

Thr Leu Val Pro Leu Gly Leu Val Leu Ala Val Gly Ala Val Ala Val
625                 630                 635                 640

Gly Val Ala Arg Ala Arg His Arg Lys Asn Val Asp Arg Val Ser Ile
                645                 650                 655

Arg Ser Tyr Arg Thr Asp Ile Ser Met Ser Asp Phe Glu Asn Ser Arg
                660                 665                 670

Glu Phe Gly Ala Asn Asp Asn Met Gly Ala Ser Ser Ile Thr Gln Glu
            675                 680                 685

Thr Ser Leu Gly Gly Lys Glu Glu Phe Val Ala Thr Thr Glu Ser Thr
            690                 695                 700

Thr Glu Thr Lys Glu Pro Lys Lys Ala Lys Arg Ser Ser Lys Glu Glu
705                 710                 715                 720

Ala Glu Met Ala Tyr Lys Asp Phe Leu Leu Gln Ser Ser Thr Val Ala
                725                 730                 735

Ala Glu Ala Gln Asp Gly Pro Gln Glu Ala
            740                 745
```

(2) INFORMATION FOR SEQ ID NO: 5:

(i) SEQUENCE CHARACTERISTICS:
        (A) LENGTH: 3630 base pairs
        (B) TYPE: nucleic acid
        (C) STRANDEDNESS: single
        (D) TOPOLOGY: linear
            DESCRIPTION: Bovine Polyimmunoglobulin Receptor (ix) FEATURE:
        (A) NAME/KEY: Coding Sequence
        (B) LOCATION: 152....2425

(xi) SEQUENCE DESCRIPTION: SEQ ID NO: 5:

```
GATCTCCTCG AGGGTCGTG  CAGCGGCCCT GGGTCCCTGC CGGCACCAGT ACTTGCGCGT      60

GTGCTCCCAA AGCTGACGGG ATAGGAGGAA GGAGCTCAAA CAACCACACA GGACGGTGGC     120

TGGCGGCAGA GACCCGCGGG AGCCCCCAGC G ATG TCG CGC CTG TTC CTC GCC       172
                                 Met Ser Arg Leu Phe Leu Ala
                                   1               5

TGC CTG CTG GCC ATC TTC CCA GTG GTC TCC ATG AAG AGT CCC ATC TTC      220
Cys Leu Leu Ala Ile Phe Pro Val Val Ser Met Lys Ser Pro Ile Phe
         10                  15                  20

GGT CCC GAG GAG GTG AGC AGC GTG GAA GGC CGC TCA GTG TCC ATC AAG      268
Gly Pro Glu Glu Val Ser Ser Val Glu Gly Arg Ser Val Ser Ile Lys
 25                  30                  35

TGC TAC TAC CCG CCC ACC TCC GTC AAC CGG CAC ACG CGC AAG TAC TGG      316
Cys Tyr Tyr Pro Pro Thr Ser Val Asn Arg His Thr Arg Lys Tyr Trp
 40                  45                  50                  55

TGC CGG CAG GGA GCC CAG GGC CGC TGC ACG ACC CTC ATC TCC TCG GAG      364
Cys Arg Gln Gly Ala Gln Gly Arg Cys Thr Thr Leu Ile Ser Ser Glu
             60                  65                  70

GGC TAC GTC TCC GAC GAC TAC GTG GGC AGA GCC AAC CTC ACC AAC TTC      412
Gly Tyr Val Ser Asp Asp Tyr Val Gly Arg Ala Asn Leu Thr Asn Phe
         75                  80                  85

CCG GAG AGC GGC ACG TTT GTG GTG GAC ATC AGC CAT CTC ACC CAT AAA      460
Pro Glu Ser Gly Thr Phe Val Val Asp Ile Ser His Leu Thr His Lys
 90                  95                 100

GAC TCA GGG CGC TAC AAG TGT GGC CTG GGC ATT AGC AGC CGT GGC CTT      508
Asp Ser Gly Arg Tyr Lys Cys Gly Leu Gly Ile Ser Ser Arg Gly Leu
105                 110                 115

AAC TTC GAT GTG AGC CTG GAG GTC AGC CAA GAT CCT GCA CAG GCA AGT      556
Asn Phe Asp Val Ser Leu Glu Val Ser Gln Asp Pro Ala Gln Ala Ser
120                 125                 130                 135

CAT GCC CAC GTC TAC ACT ATA GAC CTG GGC AGG ACT GTG ACC ATC AAC      604
His Ala His Val Tyr Thr Ile Asp Leu Gly Arg Thr Val Thr Ile Asn
             140                 145                 150

TGC CCT TTC ACG CGT GCG AAT TCT GAG AAG AGA AAA TCC TTG TGC AAG      652
Cys Pro Phe Thr Arg Ala Asn Ser Glu Lys Arg Lys Ser Leu Cys Lys
         155                 160                 165

AAG ACA ATC CAG GAC TGT TTC CAA GTT GTC GAC TCC ACC GGG TAT GTG      700
Lys Thr Ile Gln Asp Cys Phe Gln Val Val Asp Ser Thr Gly Tyr Val
 170                 175                 180

AGC AAC AGC TAT AAA GAC AGA GCA CAT ATC AGT ATC CTA GGT ACC AAC      748
Ser Asn Ser Tyr Lys Asp Arg Ala His Ile Ser Ile Leu Gly Thr Asn
185                 190                 195

ACA TTA GTG TTC AGC GTT GTC ATC AAC CGA GTC AAG CTC AGT GAT GCT      796
Thr Leu Val Phe Ser Val Val Ile Asn Arg Val Lys Leu Ser Asp Ala
200                 205                 210                 215

GGG ATG TAT GTC TGC CAG GCT GGG GAC GAT GCC AAA GCC GAT AAA ATC      844
Gly Met Tyr Val Cys Gln Ala Gly Asp Asp Ala Lys Ala Asp Lys Ile
                 220                 225                 230
```

| | |
|---|---|
| AAC ATT GAC CTC CAG GTG CTG GAG CCT GAG CCT GAG CTG GTT TAT GGA<br>Asn Ile Asp Leu Gln Val Leu Glu Pro Glu Pro Glu Leu Val Tyr Gly<br>               235                       240                    245 | 892 |
| GAC TTG AGG AGC TCG GTG ACC TTT GAC TGT TCC CTG GGC CCC GAG GTG<br>Asp Leu Arg Ser Ser Val Thr Phe Asp Cys Ser Leu Gly Pro Glu Val<br>               250                       255                    260 | 940 |
| GCA AAT GTG CCC AAA TTT CTG TGC CAG AAG AAG AAT GGG GGA GCT TGC<br>Ala Asn Val Pro Lys Phe Leu Cys Gln Lys Lys Asn Gly Gly Ala Cys<br>265                     270                       275 | 988 |
| AAT GTA GTC ATC AAC ACG TTG GGG AAG AAG GCT CAG GAC TTC CAG GGC<br>Asn Val Val Ile Asn Thr Leu Gly Lys Lys Ala Gln Asp Phe Gln Gly<br>280                     285                     290                    295 | 1036 |
| AGG ATC GTG TCC GTG CCC AAG GAC AAT GGT GTC TTC AGT GTG CAC ATT<br>Arg Ile Val Ser Val Pro Lys Asp Asn Gly Val Phe Ser Val His Ile<br>                       300                       305                    310 | 1084 |
| ACC AGC CTG AGG AAA GAG GAC GCA GGG CGC TAC GTG TGC GGG GCC CAG<br>Thr Ser Leu Arg Lys Glu Asp Ala Gly Arg Tyr Val Cys Gly Ala Gln<br>               315                       320                    325 | 1132 |
| CCT GAG GGT GAG CCC CAG GAC GGC TGG CCT GTG CAG GCC TGG CAA CTC<br>Pro Glu Gly Glu Pro Gln Asp Gly Trp Pro Val Gln Ala Trp Gln Leu<br>               330                       335                    340 | 1180 |
| TTC GTC AAT GAA GAG ACG GCA ATC CCC GCA AGC CCC TCC GTG GTG AAA<br>Phe Val Asn Glu Glu Thr Ala Ile Pro Ala Ser Pro Ser Val Val Lys<br>345                     350                       355 | 1228 |
| GGT GTG AGG GGA GGC TCT GTG ACT GTA TCT TGC CCC TAC AAC CCT AAG<br>Gly Val Arg Gly Gly Ser Val Thr Val Ser Cys Pro Tyr Asn Pro Lys<br>360                     365                       370                    375 | 1276 |
| GAT GCC AAC AGC GCG AAG TAC TGG TGT CAC TGG GAA GAG GCT CAA AAC<br>Asp Ala Asn Ser Ala Lys Tyr Trp Cys His Trp Glu Glu Ala Gln Asn<br>                       380                       385                    390 | 1324 |
| GGC CGC TGC CCG CGG CTG GTG GAG AGC CGG GGG CTG ATG AAG GAG CAG<br>Gly Arg Cys Pro Arg Leu Val Glu Ser Arg Gly Leu Met Lys Glu Gln<br>               395                       400                    405 | 1372 |
| TAC GAG GGC AGG CTG GTG CTG CTC ACC GAG CCG GGC AAC GGC ACC TAC<br>Tyr Glu Gly Arg Leu Val Leu Leu Thr Glu Pro Gly Asn Gly Thr Tyr<br>               410                       415                    420 | 1420 |
| ACC GTC ATC CTC AAC CAG CTC ACC GAT CAG GAC GCC GGC TTC TAC TGG<br>Thr Val Ile Leu Asn Gln Leu Thr Asp Gln Asp Ala Gly Phe Tyr Trp<br>               425                       430                    435 | 1468 |
| TGC GTG ACC GAC GGC GAC ACG CGC TGG ATC TCC ACA GTG GAG CTC AAG<br>Cys Val Thr Asp Gly Asp Thr Arg Trp Ile Ser Thr Val Glu Leu Lys<br>440                     445                       450                    455 | 1516 |
| GTT GTC CAA GGA GAA CCA AGC CTC AAG GTA CCC AAG AAC GTC ACG GCT<br>Val Val Gln Gly Glu Pro Ser Leu Lys Val Pro Lys Asn Val Thr Ala<br>               460                       465                    470 | 1564 |
| TGG CTG GGA GAG CCC TTA AAG CTC TCC TGC CAC TTC CCC TGC AAA TTC<br>Trp Leu Gly Glu Pro Leu Lys Leu Ser Cys His Phe Pro Cys Lys Phe<br>               475                       480                    485 | 1612 |
| TAC TCC TTT GAG AAG TAC TGG TGT AAG TGG AGC AAC AGA GGC TGC AGC<br>Tyr Ser Phe Glu Lys Tyr Trp Cys Lys Trp Ser Asn Arg Gly Cys Ser<br>               490                       495                    500 | 1660 |
| GCC CTG CCC ACC CAG AAC GAC GGC CCC AGC CAG GCC TTT GTG AGC TGC<br>Ala Leu Pro Thr Gln Asn Asp Gly Pro Ser Gln Ala Phe Val Ser Cys<br>505                     510                       515 | 1708 |
| GAC CAG AAC AGC CAG GTC GTC TCC CTG AAC CTG GAC ACA GTC ACC AAG<br>Asp Gln Asn Ser Gln Val Val Ser Leu Asn Leu Asp Thr Val Thr Lys<br>520                     525                       530                    535 | 1756 |
| GAG GAT GAA GGC TGG TAC TGG TGT GGA GTG AAG GAA GGC CCC CGA TAC<br>Glu Asp Glu Gly Trp Tyr Trp Cys Gly Val Lys Glu Gly Pro Arg Tyr | 1804 |

```
                540             545             550
GGG GAG ACG GCG GCT GTC TAC GTG GCA GTG GAG AGC AGG GTG AAG GGG    1852
Gly Glu Thr Ala Ala Val Tyr Val Ala Val Glu Ser Arg Val Lys Gly
            555             560             565

TCC CAA GGC GCC AAG CAA GTG AAA GCT GCC CCT GCG GGG GCG GCA ATA    1900
Ser Gln Gly Ala Lys Gln Val Lys Ala Ala Pro Ala Gly Ala Ala Ile
        570             575             580

CAG TCG AGG GCC GGG GAG ATC CAG AAC AAA GCC CTT CTG GAC CCC AGC    1948
Gln Ser Arg Ala Gly Glu Ile Gln Asn Lys Ala Leu Leu Asp Pro Ser
    585             590             595

TTT TTC GCA AAG GAA AGT GTG AAG GAC GCT GCT GGT GGA CCC GGA GCA    1996
Phe Phe Ala Lys Glu Ser Val Lys Asp Ala Ala Gly Gly Pro Gly Ala
600             605             610             615

CCT GCA GAT CCT GGC CGC CCT ACA GGA TAC AGC GGG AGC TCC AAA GCA    2044
Pro Ala Asp Pro Gly Arg Pro Thr Gly Tyr Ser Gly Ser Ser Lys Ala
            620             625             630

CTG GTC TCC ACC CTG GTG CCC CTG GCC CTG GTC CTG GTC GCA GGG GTC    2092
Leu Val Ser Thr Leu Val Pro Leu Ala Leu Val Leu Val Ala Gly Val
        635             640             645

GTG GCG ATC GGG GTG GTC CGA GCC CGG CAC AGG AAG AAC GTC GAC CGG    2140
Val Ala Ile Gly Val Val Arg Ala Arg His Arg Lys Asn Val Asp Arg
    650             655             660

ATT TCA ATC AGG AGC TAC CGG ACA GAT ATC AGC ATG TCA GAC TTT GAG    2188
Ile Ser Ile Arg Ser Tyr Arg Thr Asp Ile Ser Met Ser Asp Phe Glu
665             670             675

AAC TCC AGG GAT TTT GAA GGA CGT GAC AAC ATG GGA GCC TCT CCA GAG    2236
Asn Ser Arg Asp Phe Glu Gly Arg Asp Asn Met Gly Ala Ser Pro Glu
680             685             690             695

GCC CAA GAG ACG TCT CTC GGA GGG AAG GAC GAG TTT GCC ACC ACT ACC    2284
Ala Gln Glu Thr Ser Leu Gly Gly Lys Asp Glu Phe Ala Thr Thr Thr
            700             705             710

GAG GAC ACC GTG GAG AGC AAA GAA CCC AAG AAG GCA AAG AGG TCG TCC    2332
Glu Asp Thr Val Glu Ser Lys Glu Pro Lys Lys Ala Lys Arg Ser Ser
        715             720             725

AAG GAG GAA GCC GAC GAG GCC TTC ACC ACC TTC CTC CTC CAG GCC AAA    2380
Lys Glu Glu Ala Asp Glu Ala Phe Thr Thr Phe Leu Leu Gln Ala Lys
    730             735             740

AAC CTG GCC TCC GCC GCA ACC CAG AAC GGC CCG ACA GAA GCC TAG ACGGAG 2431
Asn Leu Ala Ser Ala Ala Thr Gln Asn Gly Pro Thr Glu Ala
745             750             755

CCCTGGGCGC CCCTTCCCTC CGCACGTGGC AATCACGCTC CGAATCACGC TGATCCTCAG    2491

GGCCCTCAGC TCGGGGGGCT CCACTGCCTG CACTCACACC CCGCCTAGGC TTCTCCTGTC    2551

TGTCCTCAGA GGGTGTGCTG GTTCCTTCTT GGTGGCATCC AAGCCTGGCT TACTTGTTCC    2611

TATTGGGGGT GAGGTGGTAC GAGGAGTTCC CACCTGCAGC TTATTCGAAC GAGAGAACTA    2671

AAGGTGTGGA GGAGAATTAA GATCGCAGAG GGGCCTCTCA GAAAGAAAAG GAGTGGGTGG    2731

GGAGACAACC GCAGAAAGGG GGCCATTCAG CGCTTCCCTG TCCCCTTATT TGGGGATGTC    2791

AGTGGAATCC TCCCTTCCAC CCCATCTCTG CACCTCTCCA TCCCCACTCC ATTCCATCTT    2851

CTCTTCTTCT TTCCCTCATT AAAAATGTGC ATTTGGTTAC TCACTAGATT CCAGGGACTC    2911

TGCTAGACAC TGGGATAGGT AGGCCGCAAT CCCAGGCGGC AGCCTTCCGC AAACATCAAG    2971

GAGCCCCTGG AGCCCACAGC ATCTCTTCAC GTGTACACTC ACTGACCTCT GCCTCTGCTG    3031

GGAGAAATCA TAAAGGGTCT GCAGCCCTGA GGCCTTAGGG ATTATGTAAC ACAGGCATAC    3091

ACACAAGGCA CCATCAACAC ATTCTTACCA TTTCACAGGT GAGAAAGCCG AGGTCCTGAG    3151

AGGTGGAGAG GTTTGCTCAG AGTCAGCAAG TGAGATGTAC GAGTCTCAAG CTAAAGATTT    3211
```

-continued

```
GACACCTGCT GTCCCTACAG GAGGGCCTCC TCTCTCCAGA TGAGACAGCA TTCCATAGGA    3271

AGGAGAAGAA AAATGTAAAT AAGACTGGTC TTTCACAGGC CCCACATCAG GGAAGATACC    3331

CCTTTCCCTG TCTGTCACTC ACAGAGACCT AATAGGATAA GAGAATGGTC AACACTCAAA    3391

CCCCCGAATG TGAAGAGTTC TAAGTGGAAA GGGAGGAAAA AGGGGGGATT TGATGGTGCC    3451

AGGGAGGGGC TGATCTCCAA AGAACTAAGG TTTAAGTTTT TTTGTTTTTT TTTTTCCTTC    3511

TTCTAAGCTC TGCACTTCAA CTAGCATCTA TGAGCTGGCA CTTGCTAACA AATCAAAAAT    3571

GTGAATTAAT TAATAATTAA AGACCATGAT TTCCTCCAAA AAAAAAAAAA AAAAAAAA     3630
```

(2) INFORMATION FOR SEQ ID NO: 6:

(i) SEQUENCE CHARACTERISTICS:
        (A) LENGTH: 757 amino acids
        (B) TYPE: amino acid
        (C) STRANDEDNESS: single
        (D) TOPOLOGY: linear
            DESCRIPTION:   Bovine Polyimmunoglobulin Receptor (xi) SEQUENCE DESCRIPTION: SEQ ID NO: 6:

```
Met Ser Arg Leu Phe Leu Ala Cys Leu Leu Ala Ile Phe Pro Val Val
 1               5                  10                  15

Ser Met Lys Ser Pro Ile Phe Gly Pro Glu Glu Val Ser Ser Val Glu
             20                  25                  30

Gly Arg Ser Val Ser Ile Lys Cys Tyr Tyr Pro Thr Ser Val Asn
             35                  40                  45

Arg His Thr Arg Lys Tyr Trp Cys Arg Gln Gly Ala Gln Gly Arg Cys
         50                  55                  60

Thr Thr Leu Ile Ser Ser Glu Gly Tyr Val Ser Asp Asp Tyr Val Gly
65                  70                  75                  80

Arg Ala Asn Leu Thr Asn Phe Pro Glu Ser Gly Thr Phe Val Val Asp
                 85                  90                  95

Ile Ser His Leu Thr His Lys Asp Ser Gly Arg Tyr Lys Cys Gly Leu
             100                 105                 110

Gly Ile Ser Ser Arg Gly Leu Asn Phe Asp Val Ser Leu Glu Val Ser
             115                 120                 125

Gln Asp Pro Ala Gln Ala Ser His Ala His Val Tyr Thr Ile Asp Leu
         130                 135                 140

Gly Arg Thr Val Thr Ile Asn Cys Pro Phe Thr Arg Ala Asn Ser Glu
145                 150                 155                 160

Lys Arg Lys Ser Leu Cys Lys Lys Thr Ile Gln Asp Cys Phe Gln Val
                 165                 170                 175

Val Asp Ser Thr Gly Tyr Val Ser Asn Ser Tyr Lys Asp Arg Ala His
             180                 185                 190

Ile Ser Ile Leu Gly Thr Asn Thr Leu Val Phe Ser Val Val Ile Asn
         195                 200                 205

Arg Val Lys Leu Ser Asp Ala Gly Met Tyr Val Cys Gln Ala Gly Asp
     210                 215                 220

Asp Ala Lys Ala Asp Lys Ile Asn Ile Asp Leu Gln Val Leu Glu Pro
225                 230                 235                 240

Glu Pro Glu Leu Val Tyr Gly Asp Leu Arg Ser Ser Val Thr Phe Asp
                 245                 250                 255

Cys Ser Leu Gly Pro Glu Val Ala Asn Val Pro Lys Phe Leu Cys Gln
             260                 265                 270

Lys Lys Asn Gly Gly Ala Cys Asn Val Val Ile Asn Thr Leu Gly Lys
```

-continued

```
                275                 280                 285
Lys Ala Gln Asp Phe Gln Gly Arg Ile Val Ser Val Pro Lys Asp Asn
290                 295                 300
Gly Val Phe Ser Val His Ile Thr Ser Leu Arg Lys Glu Asp Ala Gly
305                 310                 315                 320
Arg Tyr Val Cys Gly Ala Gln Pro Glu Gly Glu Pro Gln Asp Gly Trp
                325                 330                 335
Pro Val Gln Ala Trp Gln Leu Phe Val Asn Glu Glu Thr Ala Ile Pro
                340                 345                 350
Ala Ser Pro Ser Val Val Lys Gly Val Arg Gly Gly Ser Val Thr Val
                355                 360                 365
Ser Cys Pro Tyr Asn Pro Lys Asp Ala Asn Ser Ala Lys Tyr Trp Cys
        370                 375                 380
His Trp Glu Glu Ala Gln Asn Gly Arg Cys Pro Arg Leu Val Glu Ser
385                 390                 395                 400
Arg Gly Leu Met Lys Glu Gln Tyr Glu Gly Arg Leu Val Leu Leu Thr
                405                 410                 415
Glu Pro Gly Asn Gly Thr Tyr Thr Val Ile Leu Asn Gln Leu Thr Asp
                420                 425                 430
Gln Asp Ala Gly Phe Tyr Trp Cys Val Thr Asp Gly Asp Thr Arg Trp
                435                 440                 445
Ile Ser Thr Val Glu Leu Lys Val Val Gln Gly Glu Pro Ser Leu Lys
        450                 455                 460
Val Pro Lys Asn Val Thr Ala Trp Leu Gly Glu Pro Leu Lys Leu Ser
465                 470                 475                 480
Cys His Phe Pro Cys Lys Phe Tyr Ser Phe Glu Lys Tyr Trp Cys Lys
                485                 490                 495
Trp Ser Asn Arg Gly Cys Ser Ala Leu Pro Thr Gln Asn Asp Gly Pro
                500                 505                 510
Ser Gln Ala Phe Val Ser Cys Asp Gln Asn Ser Gln Val Val Ser Leu
                515                 520                 525
Asn Leu Asp Thr Val Thr Lys Glu Asp Glu Gly Trp Tyr Trp Cys Gly
        530                 535                 540
Val Lys Glu Gly Pro Arg Tyr Gly Glu Thr Ala Ala Val Tyr Val Ala
545                 550                 555                 560
Val Glu Ser Arg Val Lys Gly Ser Gln Gly Ala Lys Gln Val Lys Ala
                565                 570                 575
Ala Pro Ala Gly Ala Ala Ile Gln Ser Arg Ala Gly Glu Ile Gln Asn
                580                 585                 590
Lys Ala Leu Leu Asp Pro Ser Phe Phe Ala Lys Glu Ser Val Lys Asp
                595                 600                 605
Ala Ala Gly Gly Pro Gly Ala Pro Ala Asp Pro Gly Arg Pro Thr Gly
                610                 615                 620
Tyr Ser Gly Ser Ser Lys Ala Leu Val Ser Thr Leu Val Pro Leu Ala
625                 630                 635                 640
Leu Val Leu Val Ala Gly Val Val Ala Ile Gly Val Val Arg Ala Arg
                645                 650                 655
His Arg Lys Asn Val Asp Arg Ile Ser Ile Arg Ser Tyr Arg Thr Asp
                660                 665                 670
Ile Ser Met Ser Asp Phe Glu Asn Ser Arg Asp Phe Glu Gly Arg Asp
                675                 680                 685
Asn Met Gly Ala Ser Pro Glu Ala Gln Glu Thr Ser Leu Gly Gly Lys
                690                 695                 700
```

```
Asp Glu Phe Ala Thr Thr Thr Glu Asp Thr Val Glu Ser Lys Glu Pro
705                 710                 715                 720

Lys Lys Ala Lys Arg Ser Ser Lys Glu Glu Ala Asp Glu Ala Phe Thr
            725                 730                 735

Thr Phe Leu Leu Gln Ala Lys Asn Leu Ala Ser Ala Ala Thr Gln Asn
        740                 745                 750

Gly Pro Thr Glu Ala
        755
```

(2) INFORMATION FOR SEQ ID NO: 7:

(i) SEQUENCE CHARACTERISTICS:
        (A) LENGTH: 3095 base pairs
        (B) TYPE: nucleic acid
        (C) STRANDEDNESS: single
        (D) TOPOLOGY: linear
            DESCRIPTION:    Mouse Polyimmunoglobulin Receptor (ix) FEATURE:
        (A) NAME/KEY: Coding Sequence
        (B) LOCATION: 85....2400

(xi) SEQUENCE DESCRIPTION: SEQ ID NO: 7:

```
TCACCTGGAG AGAAGGAAGT AGCTAAAACA TTCTCATACA AGAAGCCAAC CTGAGCGGCA         60

CAGCCCCCCT GGAAGCCACA AGCA ATG AGG CTC TAC TTG TTC ACG CTC TTG          111
                          Met Arg Leu Tyr Leu Phe Thr Leu Leu
                            1               5

GTA ACT GTC TTT TCA GGG GTC TCC ACA AAA AGC CCC ATA TTT GGT CCC         159
Val Thr Val Phe Ser Gly Val Ser Thr Lys Ser Pro Ile Phe Gly Pro
 10              15                  20                  25

CAG GAG GTG AGT AGT ATA GAA GGC GAC TCT GTT TCC ATC ACG TGC TAC         207
Gln Glu Val Ser Ser Ile Glu Gly Asp Ser Val Ser Ile Thr Cys Tyr
                 30                  35                  40

TAC CCA GAC ACC TCT GTC AAC CGG CAC ACC CGG AAA TAC TGG TGC CGA         255
Tyr Pro Asp Thr Ser Val Asn Arg His Thr Arg Lys Tyr Trp Cys Arg
             45                  50                  55

CAA GGA GCC AGC GGC ATG TGC ACA ACG CTC ATC TCT TCA AAT GGC TAC         303
Gln Gly Ala Ser Gly Met Cys Thr Thr Leu Ile Ser Ser Asn Gly Tyr
         60                  65                  70

CTC TCC AAG GAG TAT TCA GGC AGA GCC AAC CTC ATC AAC TTC CCA GAG         351
Leu Ser Lys Glu Tyr Ser Gly Arg Ala Asn Leu Ile Asn Phe Pro Glu
     75                  80                  85

AAC AAC ACA TTT GTG ATT AAC ATT GAG CAG CTC ACC CAG GAC GAC ACT         399
Asn Asn Thr Phe Val Ile Asn Ile Glu Gln Leu Thr Gln Asp Asp Thr
 90                  95                 100                 105

GGG AGC TAC AAG TGT GGC CTG GGT ACC AGT AAC CGA GGC CTG TCC TTC         447
Gly Ser Tyr Lys Cys Gly Leu Gly Thr Ser Asn Arg Gly Leu Ser Phe
                110                 115                 120

GAT GTC AGC CTG GAG GTC AGC CAG GTT CCT GAG TTG CCG AGT GAC ACC         495
Asp Val Ser Leu Glu Val Ser Gln Val Pro Glu Leu Pro Ser Asp Thr
            125                 130                 135

CAC GTC TAC ACA AAG GAC ATA GGC AGA AAT GTG ACC ATT GAA TGC CCT         543
His Val Tyr Thr Lys Asp Ile Gly Arg Asn Val Thr Ile Glu Cys Pro
        140                 145                 150

TTC AAA AGG GAG AAT GTT CCC AGC AAG AAA TCC CTG TGT AAG AAG ACA         591
Phe Lys Arg Glu Asn Val Pro Ser Lys Lys Ser Leu Cys Lys Lys Thr
    155                 160                 165

AAC CAG TCC TGC GAA CTT GTC ATT GAC TCT ACT GAG AAG GTG AAC CCC         639
Asn Gln Ser Cys Glu Leu Val Ile Asp Ser Thr Glu Lys Val Asn Pro
170                 175                 180                 185
```

```
AGC TAT ATA GGC AGA GCA AAA CTT TTT ATG AAA GGG ACC GAC CTA ACT        687
Ser Tyr Ile Gly Arg Ala Lys Leu Phe Met Lys Gly Thr Asp Leu Thr
            190                 195                 200

GTA TTC TAT GTC AAC ATT AGT CAC CTA ACG CAC AAT GAT GCT GGG CTG        735
Val Phe Tyr Val Asn Ile Ser His Leu Thr His Asn Asp Ala Gly Leu
                205                 210                 215

TAC ATC TGC CAA GCT GGA GAA GGT CCT AGT GCT GAT AAG AAG AAT GTT        783
Tyr Ile Cys Gln Ala Gly Glu Gly Pro Ser Ala Asp Lys Lys Asn Val
                220                 225                 230

GAC CTC CAG GTG CTA GCG CCT GAG CCA GAG CTG CTT TAT AAA GAC CTG        831
Asp Leu Gln Val Leu Ala Pro Glu Pro Glu Leu Leu Tyr Lys Asp Leu
            235                 240                 245

AGG TCC TCA GTG ACT TTT GAA TGT GAC CTG GGC CGT GAG GTG GCA AAC        879
Arg Ser Ser Val Thr Phe Glu Cys Asp Leu Gly Arg Glu Val Ala Asn
250                 255                 260                 265

GAG GCC AAA TAT CTG TGC CGG ATG AAT AAG GAA ACC TGT GAT GTG ATC        927
Glu Ala Lys Tyr Leu Cys Arg Met Asn Lys Glu Thr Cys Asp Val Ile
                270                 275                 280

ATT AAC ACC CTG GGG AAG AGG GAT CCA GAC TTT GAG GGC AGG ATC CTG        975
Ile Asn Thr Leu Gly Lys Arg Asp Pro Asp Phe Glu Gly Arg Ile Leu
                285                 290                 295

ATA ACC CCC AAG GAT GAC AAT GGC CGC TTC AGT GTG TTG ATC ACA GGC       1023
Ile Thr Pro Lys Asp Asp Asn Gly Arg Phe Ser Val Leu Ile Thr Gly
            300                 305                 310

CTG AGG AAG GAG GAT GCA GGG CAC TAC CAG TGT GGA GCC CAC AGT TCT       1071
Leu Arg Lys Glu Asp Ala Gly His Tyr Gln Cys Gly Ala His Ser Ser
            315                 320                 325

GGT TTG CCT CAA GAA GGC TGG CCC ATC CAG ACT TGG CAA CTC TTT GTC       1119
Gly Leu Pro Gln Glu Gly Trp Pro Ile Gln Thr Trp Gln Leu Phe Val
330                 335                 340                 345

AAT GAA GAG TCT ACC ATT CCC AAT CGT CGC TCT GTT GTG AAG GGA GTC       1167
Asn Glu Glu Ser Thr Ile Pro Asn Arg Arg Ser Val Val Lys Gly Val
                350                 355                 360

ACA GGA GGC TCT GTG GCC ATC GCC TGT CCC TAT AAC CCC AAG GAA AGC       1215
Thr Gly Gly Ser Val Ala Ile Ala Cys Pro Tyr Asn Pro Lys Glu Ser
            365                 370                 375

AGC AGC CTC AAG TAC TGG TGT CGC TGG GAA GGG GAC GGA AAT GGA CAT       1263
Ser Ser Leu Lys Tyr Trp Cys Arg Trp Glu Gly Asp Gly Asn Gly His
            380                 385                 390

TGC CCC GCG CTT GTG GGG ACC CAG GCC CAG GTG CAA GAA GAG TAT GAA       1311
Cys Pro Ala Leu Val Gly Thr Gln Ala Gln Val Gln Glu Glu Tyr Glu
395                 400                 405

GGC CGA CTG GCA CTG TTT GAT CAG CCA GGC AAT GGT ACT TAC ACT GTC       1359
Gly Arg Leu Ala Leu Phe Asp Gln Pro Gly Asn Gly Thr Tyr Thr Val
410                 415                 420                 425

ATC CTC AAC CAG CTC ACC ACC GAG GAT GCT GGC TTC TAT TGG TGT CTT       1407
Ile Leu Asn Gln Leu Thr Thr Glu Asp Ala Gly Phe Tyr Trp Cys Leu
                430                 435                 440

ACC AAT GGT GAC TCT CGC TGG AGA ACC ACA ATA GAA CTC CAG GTT GCC       1455
Thr Asn Gly Asp Ser Arg Trp Arg Thr Thr Ile Glu Leu Gln Val Ala
            445                 450                 455

GAA GCT ACA AGG GAG CCA AAC CTT GAG GTG ACG CCA CAG AAC GCA ACA       1503
Glu Ala Thr Arg Glu Pro Asn Leu Glu Val Thr Pro Gln Asn Ala Thr
            460                 465                 470

GCA GTA CTA GGA GAG ACC TTC ACC GTT TCC TGC CAC TAT CCG TGC AAA       1551
Ala Val Leu Gly Glu Thr Phe Thr Val Ser Cys His Tyr Pro Cys Lys
            475                 480                 485

TTC TAC TCC CAG GAG AAA TAC TGG TGC AAG TGG AGC AAC AAG GGT TGC       1599
Phe Tyr Ser Gln Glu Lys Tyr Trp Cys Lys Trp Ser Asn Lys Gly Cys
490                 495                 500                 505
```

```
CAC ATC CTG CCA AGC CAT GAC GAA GGT GCC CGC CAA TCT TCT GTG AGC    1647
His Ile Leu Pro Ser His Asp Glu Gly Ala Arg Gln Ser Ser Val Ser
            510                 515                 520

TGC GAC CAG AGC AGC CAG CTG GTC TCC ATG ACC CTG AAC CCG GTC AGT    1695
Cys Asp Gln Ser Ser Gln Leu Val Ser Met Thr Leu Asn Pro Val Ser
            525                 530                 535

AAG GAA GAT GAA GGC TGG TAC TGG TGT GGG GTA AAG CAA GGC CAG ACC    1743
Lys Glu Asp Glu Gly Trp Tyr Trp Cys Gly Val Lys Gln Gly Gln Thr
            540                 545                 550

TAT GGA GAA ACT ACC GCC ATC TAT ATA GCA GTT GAA GAG AGG ACC AGA    1791
Tyr Gly Glu Thr Thr Ala Ile Tyr Ile Ala Val Glu Glu Arg Thr Arg
            555                 560                 565

GGG TCA TCC CAT GTC AAC CCA ACA GAT GCA AAT GCA CGT GCC AAA GTC    1839
Gly Ser Ser His Val Asn Pro Thr Asp Ala Asn Ala Arg Ala Lys Val
570                 575                 580                 585

GCT CTG GAA GAA GAG GTA GTG GAC TCC TCC ATC AGT GAA AAA GAG AAC    1887
Ala Leu Glu Glu Glu Val Val Asp Ser Ser Ile Ser Glu Lys Glu Asn
            590                 595                 600

AAA GCC ATT CCA AAT CCC GGG CCT TTT GCC AAC GAA AGA GAG ATA CAG    1935
Lys Ala Ile Pro Asn Pro Gly Pro Phe Ala Asn Glu Arg Glu Ile Gln
            605                 610                 615

AAT GTG AGA GAC CAA GCT CAG GAG AAC AGA GCA TCT GGG GAT GCT GGC    1983
Asn Val Arg Asp Gln Ala Gln Glu Asn Arg Ala Ser Gly Asp Ala Gly
            620                 625                 630

AGT GCT GAT GGA CAA AGC AGG AGC TCC AGC TCC AAA GTG CTG TTC TCC    2031
Ser Ala Asp Gly Gln Ser Arg Ser Ser Ser Ser Lys Val Leu Phe Ser
            635                 640                 645

ACC CTG GTG CCC CTG GGT CTG GTG CTG GCA GTG GGT GCT ATA GCT GTG    2079
Thr Leu Val Pro Leu Gly Leu Val Leu Ala Val Gly Ala Ile Ala Val
650                 655                 660                 665

TGG GTG GCC AGA GTC CGA CAT CGG AAG AAT GTA GAC CGC ATG TCA ATC    2127
Trp Val Ala Arg Val Arg His Arg Lys Asn Val Asp Arg Met Ser Ile
            670                 675                 680

AGC AGC TAC AGG ACA GAC ATT AGC ATG GCA GAC TTC AAG AAC TCC AGA    2175
Ser Ser Tyr Arg Thr Asp Ile Ser Met Ala Asp Phe Lys Asn Ser Arg
            685                 690                 695

GAT TTG GGA GGC AAT GAC AAC ATG GGG GCC TCT CCA GAC ACA CAG CAA    2223
Asp Leu Gly Gly Asn Asp Asn Met Gly Ala Ser Pro Asp Thr Gln Gln
            700                 705                 710

ACA GTC ATC GAA GGA AAA GAT GAA ATC GTG ACT ACC ACG GAG TGC ACC    2271
Thr Val Ile Glu Gly Lys Asp Glu Ile Val Thr Thr Thr Glu Cys Thr
            715                 720                 725

GCT GAG CCA GAA GAA TCC AAG AAA GCA AAA AGG TCA TCC AAG GAG GAA    2319
Ala Glu Pro Glu Glu Ser Lys Lys Ala Lys Arg Ser Ser Lys Glu Glu
730                 735                 740                 745

GCT GAC ATG GCC TAC TCG GCA TTC CTG CTT CAG TCC AGC ACC ATA GCT    2367
Ala Asp Met Ala Tyr Ser Ala Phe Leu Leu Gln Ser Ser Thr Ile Ala
            750                 755                 760

GCA CAG GTC CAC GAT GGT CCC CAG GAA GCC TAG GCAGTGCTGA CCACCCACCC   2420
Ala Gln Val His Asp Gly Pro Gln Glu Ala
            765                 770

TTGCCTGTGA CAATCAACTT GAGAATCACA CTGATCCGCT CGCAGCCCAC ACTCACCCAT   2480

CACCTCCGCT CTTCCCTCCT GTCCTCAGAG GTGTGCTGGT TCCTTCCTCG GCCATGGAAG   2540

CCTGGCCTAG TTACGCCTGT TTAGGAGAGA GTGTGAGGCG TTCTTTTCTC TATGAAGAGA   2600

GTGAGGTGGA AATGAGGAGG AGGTGAACCT GAGAGACATC TCTGGAGGAA GAGGGTTGAG   2660

AATAGGGGCT CGTTTCAGGA GAAAAGGCCA TTTGAATCTT CTTTATAACC ATATGATAGG   2720
```

-continued

```
ATGTCAGCGT AACTCTTCTC TCCTCCATCT CTCCTTTCCT ATCCTCTTGA TTCAAACAAC    2780

ACATCTGAGA ACTCACTAGG CTTCAGTGCC TACTAAATGC TGAGAGCCAG GCCACAATCT    2840

TTCTATAAAT ATTACTGGAA GAGATGCCAT CTCCTCCCAG ATTCTGTCTT TTCATTAAGA    2900

TAAGACATCA TTACCAGGCA TACCTCCTGC CTCTGTGCCT CATAGGCATA CACAAGCCAT    2960

AAGGGCATCA TGATTTTCAG ATGAGAAGAG ATGTTTCTCA AGAGTGCCTA GTGAGATAGA    3020

CTAGCGTCAA ACCAGATGTG GCAACTCCTG GCTCTTGGCC TACGATCTGT CTTCAAGAAA    3080

AAAAAAAAAA AAAAA                                                     3095
```

(2) INFORMATION FOR SEQ ID NO: 8:

(i) SEQUENCE CHARACTERISTICS:
        (A) LENGTH: 771 amino acids
        (B) TYPE: amino acid
        (C) STRANDEDNESS: single
        (D) TOPOLOGY: linear
            DESCRIPTION:    Mouse Polyimmunoglobulin Receptor (xi) SEQUENCE DESCRIPTION: SEQ ID NO: 8:

```
Met Arg Leu Tyr Leu Phe Thr Leu Leu Val Thr Val Phe Ser Gly Val
 1               5                  10                  15

Ser Thr Lys Ser Pro Ile Phe Gly Pro Gln Glu Val Ser Ser Ile Glu
                20                  25                  30

Gly Asp Ser Val Ser Ile Thr Cys Tyr Tyr Pro Asp Thr Ser Val Asn
            35                  40                  45

Arg His Thr Arg Lys Tyr Trp Cys Arg Gln Gly Ala Ser Gly Met Cys
        50                  55                  60

Thr Thr Leu Ile Ser Ser Asn Gly Tyr Leu Ser Lys Glu Tyr Ser Gly
65                  70                  75                  80

Arg Ala Asn Leu Ile Asn Phe Pro Glu Asn Asn Thr Phe Val Ile Asn
                85                  90                  95

Ile Glu Gln Leu Thr Gln Asp Asp Thr Gly Ser Tyr Lys Cys Gly Leu
            100                 105                 110

Gly Thr Ser Asn Arg Gly Leu Ser Phe Asp Val Ser Leu Glu Val Ser
        115                 120                 125

Gln Val Pro Glu Leu Pro Ser Asp Thr His Val Tyr Thr Lys Asp Ile
    130                 135                 140

Gly Arg Asn Val Thr Ile Glu Cys Pro Phe Lys Arg Glu Asn Val Pro
145                 150                 155                 160

Ser Lys Lys Ser Leu Cys Lys Lys Thr Asn Gln Ser Cys Glu Leu Val
                165                 170                 175

Ile Asp Ser Thr Glu Lys Val Asn Pro Ser Tyr Ile Gly Arg Ala Lys
            180                 185                 190

Leu Phe Met Lys Gly Thr Asp Leu Thr Val Phe Tyr Val Asn Ile Ser
        195                 200                 205

His Leu Thr His Asn Asp Ala Gly Leu Tyr Ile Cys Gln Ala Gly Glu
    210                 215                 220

Gly Pro Ser Ala Asp Lys Lys Asn Val Asp Leu Gln Val Leu Ala Pro
225                 230                 235                 240

Glu Pro Glu Leu Leu Tyr Lys Asp Leu Arg Ser Ser Val Thr Phe Glu
                245                 250                 255

Cys Asp Leu Gly Arg Glu Val Ala Asn Glu Ala Lys Tyr Leu Cys Arg
            260                 265                 270

Met Asn Lys Glu Thr Cys Asp Val Ile Ile Asn Thr Leu Gly Lys Arg
        275                 280                 285
```

```
Asp Pro Asp Phe Glu Gly Arg Ile Leu Ile Thr Pro Lys Asp Asp Asn
290                 295                 300

Gly Arg Phe Ser Val Leu Ile Thr Gly Leu Arg Lys Glu Asp Ala Gly
305                 310                 315                 320

His Tyr Gln Cys Gly Ala His Ser Ser Gly Leu Pro Gln Glu Gly Trp
                325                 330                 335

Pro Ile Gln Thr Trp Gln Leu Phe Val Asn Glu Glu Ser Thr Ile Pro
                340                 345                 350

Asn Arg Arg Ser Val Val Lys Gly Val Thr Gly Gly Ser Val Ala Ile
                355                 360                 365

Ala Cys Pro Tyr Asn Pro Lys Glu Ser Ser Ser Leu Lys Tyr Trp Cys
370                 375                 380

Arg Trp Glu Gly Asp Gly Asn Gly His Cys Pro Ala Leu Val Gly Thr
385                 390                 395                 400

Gln Ala Gln Val Gln Glu Glu Tyr Glu Gly Arg Leu Ala Leu Phe Asp
                405                 410                 415

Gln Pro Gly Asn Gly Thr Tyr Thr Val Ile Leu Asn Gln Leu Thr Thr
                420                 425                 430

Glu Asp Ala Gly Phe Tyr Trp Cys Leu Thr Asn Gly Asp Ser Arg Trp
                435                 440                 445

Arg Thr Thr Ile Glu Leu Gln Val Ala Glu Ala Thr Arg Glu Pro Asn
450                 455                 460

Leu Glu Val Thr Pro Gln Asn Ala Thr Ala Val Leu Gly Glu Thr Phe
465                 470                 475                 480

Thr Val Ser Cys His Tyr Pro Cys Lys Phe Tyr Ser Gln Glu Lys Tyr
                485                 490                 495

Trp Cys Lys Trp Ser Asn Lys Gly Cys His Ile Leu Pro Ser His Asp
                500                 505                 510

Glu Gly Ala Arg Gln Ser Ser Val Ser Cys Asp Gln Ser Ser Gln Leu
                515                 520                 525

Val Ser Met Thr Leu Asn Pro Val Ser Lys Glu Asp Glu Gly Trp Tyr
530                 535                 540

Trp Cys Gly Val Lys Gln Gly Gln Thr Tyr Gly Glu Thr Thr Ala Ile
545                 550                 555                 560

Tyr Ile Ala Val Glu Glu Arg Thr Arg Gly Ser Ser His Val Asn Pro
                565                 570                 575

Thr Asp Ala Asn Ala Arg Ala Lys Val Ala Leu Glu Glu Val Val
                580                 585                 590

Asp Ser Ser Ile Ser Glu Lys Glu Asn Lys Ala Ile Pro Asn Pro Gly
                595                 600                 605

Pro Phe Ala Asn Glu Arg Glu Ile Gln Asn Val Arg Asp Gln Ala Gln
                610                 615                 620

Glu Asn Arg Ala Ser Gly Asp Ala Gly Ser Ala Asp Gly Gln Ser Arg
625                 630                 635                 640

Ser Ser Ser Ser Lys Val Leu Phe Ser Thr Leu Val Pro Leu Gly Leu
                645                 650                 655

Val Leu Ala Val Gly Ala Ile Ala Val Trp Val Ala Arg Val Arg His
                660                 665                 670

Arg Lys Asn Val Asp Arg Met Ser Ile Ser Ser Tyr Arg Thr Asp Ile
                675                 680                 685

Ser Met Ala Asp Phe Lys Asn Ser Arg Asp Leu Gly Gly Asn Asp Asn
690                 695                 700
```

```
Met Gly Ala Ser Pro Asp Thr Gln Gln Thr Val Ile Glu Gly Lys Asp
705                 710                 715                 720

Glu Ile Val Thr Thr Thr Glu Cys Thr Ala Glu Pro Glu Glu Ser Lys
            725                 730                 735

Lys Ala Lys Arg Ser Ser Lys Glu Glu Ala Asp Met Ala Tyr Ser Ala
        740                 745                 750

Phe Leu Leu Gln Ser Ser Thr Ile Ala Ala Gln Val His Asp Gly Pro
    755                 760                 765

Gln Glu Ala
    770

(2) INFORMATION FOR SEQ ID NO: 9:

(i) SEQUENCE CHARACTERISTICS:
        (A) LENGTH: 3269 base pairs
        (B) TYPE: nucleic acid
        (C) STRANDEDNESS: single
        (D) TOPOLOGY: linear
            DESCRIPTION:    Rat Polyimmunoglobulin Receptor (ix) FEATURE:
        (A) NAME/KEY: Coding Sequence
        (B) LOCATION: 74....2383

(xi) SEQUENCE DESCRIPTION: SEQ ID NO: 9:

GGCAACGAAG GTACCATGGA TCTTATACAA GAAGTGAACC AACATGCCGC AACCTCCTTG         60

GAAGCCACAA GCG ATG AGG CTC TCC TTG TTC GCC CTC TTG GTA ACT GTC          109
            Met Arg Leu Ser Leu Phe Ala Leu Leu Val Thr Val
            1               5                   10

TTC TCA GGG GTC TCC ACA CAA AGC CCC ATA TTT GGT CCC CAG GAT GTG         157
Phe Ser Gly Val Ser Thr Gln Ser Pro Ile Phe Gly Pro Gln Asp Val
        15                  20                  25

AGT AGT ATT GAA GGT AAC TCG GTC TCC ATC ACG TGC TAC TAC CCA GAC         205
Ser Ser Ile Glu Gly Asn Ser Val Ser Ile Thr Cys Tyr Tyr Pro Asp
    30                  35                  40

ACC TCT GTC AAC CGG CAC ACC CGG AAA TAC TGG TGC CGA CAA GGA GCC         253
Thr Ser Val Asn Arg His Thr Arg Lys Tyr Trp Cys Arg Gln Gly Ala
45                  50                  55                  60

AAC GGC TAC TGC GCA ACC CTC ATC TCT TCA AAT GGC TAC CTC TCG AAG         301
Asn Gly Tyr Cys Ala Thr Leu Ile Ser Ser Asn Gly Tyr Leu Ser Lys
                65                  70                  75

GAG TAT TCA GGC AGA GCC AGC CTC ATC AAC TTC CCA GAG AAT AGC ACA         349
Glu Tyr Ser Gly Arg Ala Ser Leu Ile Asn Phe Pro Glu Asn Ser Thr
            80                  85                  90

TTT GTG ATT AAC ATT GCA CAT CTC ACC CAG GAG GAC ACT GGG AGC TAC         397
Phe Val Ile Asn Ile Ala His Leu Thr Gln Glu Asp Thr Gly Ser Tyr
        95                  100                 105

AAG TGT GGT CTG GGT ACC ACT AAC CGA GGC CTG TTT TTC GAT GTC AGC         445
Lys Cys Gly Leu Gly Thr Thr Asn Arg Gly Leu Phe Phe Asp Val Ser
    110                 115                 120

CTG GAG GTC AGC CAG GTT CCT GAG TTC CCA AAT GAC ACC CAT GTC TAC         493
Leu Glu Val Ser Gln Val Pro Glu Phe Pro Asn Asp Thr His Val Tyr
125                 130                 135                 140

ACA AAG GAC ATA GGC AGA ACT GTG ACC ATC GAA TGC CGT TTC AAA GAG         541
Thr Lys Asp Ile Gly Arg Thr Val Thr Ile Glu Cys Arg Phe Lys Glu
                145                 150                 155

GGG AAT GCT CAT AGC AAG AAA TCC CTG TGT AAG AAG AGA GGA GAG GCC         589
Gly Asn Ala His Ser Lys Lys Ser Leu Cys Lys Lys Arg Gly Glu Ala
            160                 165                 170

TGC GAA GTT GTC ATC GAC TCT ACT GAG TAC GTG GAC CCC AGC TAT AAG         637
Cys Glu Val Val Ile Asp Ser Thr Glu Tyr Val Asp Pro Ser Tyr Lys
```

```
                175                 180                 185
GAC AGA GCA ATC CTT TTT ATG AAA GGG ACC AGC CGC GAT ATA TTC TAT    685
Asp Arg Ala Ile Leu Phe Met Lys Gly Thr Ser Arg Asp Ile Phe Tyr
    190                 195                 200

GTC AAC ATT AGC CAC CTA ATA CCC AGT GAT GCT GGA CTG TAT GTT TGC    733
Val Asn Ile Ser His Leu Ile Pro Ser Asp Ala Gly Leu Tyr Val Cys
205                 210                 215                 220

CAA GCT GGA GAA GGC CCC AGT GCT GAT AAA AAT AAT GCT GAC CTC CAG    781
Gln Ala Gly Glu Gly Pro Ser Ala Asp Lys Asn Asn Ala Asp Leu Gln
            225                 230                 235

GTG CTA GAG CCT GAG CCA GAG CTG CTT TAT AAA GAC CTG AGG TCC TCA    829
Val Leu Glu Pro Glu Pro Glu Leu Leu Tyr Lys Asp Leu Arg Ser Ser
                240                 245                 250

GTG ACT TTT GAA TGT GAC CTG GGC CGT GAA GTG GCA AAT GAT GCC AAA    877
Val Thr Phe Glu Cys Asp Leu Gly Arg Glu Val Ala Asn Asp Ala Lys
        255                 260                 265

TAT CTG TGT CGG AAG AAC AAG GAA ACC TGT GAT GTC ATC ATC AAC ACC    925
Tyr Leu Cys Arg Lys Asn Lys Glu Thr Cys Asp Val Ile Ile Asn Thr
270                 275                 280

CTG GGG AAG AGA GAT CCA GCC TTT GAA GGC AGG ATC CTG CTA ACC CCC    973
Leu Gly Lys Arg Asp Pro Ala Phe Glu Gly Arg Ile Leu Leu Thr Pro
285                 290                 295                 300

AGG GAT GAC AAT GGC CGC TTC AGT GTG TTG ATC ACA GGC CTG AGG AAG   1021
Arg Asp Asp Asn Gly Arg Phe Ser Val Leu Ile Thr Gly Leu Arg Lys
                305                 310                 315

GAG GAT GCA GGG CAC TAC CAG TGT GGA GCG CAC AGT TCT GGT TTG CCT   1069
Glu Asp Ala Gly His Tyr Gln Cys Gly Ala His Ser Ser Gly Leu Pro
            320                 325                 330

CAA GAA GGC TGG CCC GTC CAG GCT TGG CAA CTC TTT GTC AAT GAA GAG   1117
Gln Glu Gly Trp Pro Val Gln Ala Trp Gln Leu Phe Val Asn Glu Glu
                335                 340                 345

TCC ACG ATT CCC AAT AGT CGC TCT GTT GTG AAG GGT GTC ACA GGA GGC   1165
Ser Thr Ile Pro Asn Ser Arg Ser Val Val Lys Gly Val Thr Gly Gly
        350                 355                 360

TCT GTG GCC ATC GTC TGT CCC TAT AAC CCC AAG GAA AGC AGC AGC CTC   1213
Ser Val Ala Ile Val Cys Pro Tyr Asn Pro Lys Glu Ser Ser Ser Leu
365                 370                 375                 380

AAG TAC TGG TGT CAC TGG GAA GCC GAC GAG AAT GGA CGC TGC CCG GTG   1261
Lys Tyr Trp Cys His Trp Glu Ala Asp Glu Asn Gly Arg Cys Pro Val
                385                 390                 395

CTC GTG GGG ACC CAG GCC CTG GTG CAA GAA GGA TAT GAA GGC CGA CTG   1309
Leu Val Gly Thr Gln Ala Leu Val Gln Glu Gly Tyr Glu Gly Arg Leu
            400                 405                 410

GCA CTG TTC GAT CAG CCG GGC AGT GGC GCC TAC ACT GTC ATC CTC AAC   1357
Ala Leu Phe Asp Gln Pro Gly Ser Gly Ala Tyr Thr Val Ile Leu Asn
                415                 420                 425

CAG CTC ACC ACC CAG GAT TCT GGC TTC TAC TGG TGT CTT ACC GAT GGT   1405
Gln Leu Thr Thr Gln Asp Ser Gly Phe Tyr Trp Cys Leu Thr Asp Gly
        430                 435                 440

GAC TCT CGC TGG AGA ACC ACG ATA GAA CTG CAG GTT GCT GAA GCT ACA   1453
Asp Ser Arg Trp Arg Thr Thr Ile Glu Leu Gln Val Ala Glu Ala Thr
445                 450                 455                 460

AAG AAG CCA GAC CTT GAG GTG ACA CCA CAG AAC GCG ACC GCG GTG ATA   1501
Lys Lys Pro Asp Leu Glu Val Thr Pro Gln Asn Ala Thr Ala Val Ile
                465                 470                 475

GGA GAG ACC TTC ACA ATC TCC TGC CAC TAT CCG TGC AAA TTC TAC TCC   1549
Gly Glu Thr Phe Thr Ile Ser Cys His Tyr Pro Cys Lys Phe Tyr Ser
            480                 485                 490

CAG GAG AAA TAC TGG TGC AAG TGG AGC AAC GAC GGC TGC CAC ATC CTG   1597
```

```
                Gln Glu Lys Tyr Trp Cys Lys Trp Ser Asn Asp Gly Cys His Ile Leu
                        495                 500                 505

CCG AGC CAT GAT GAA GGT GCC CGC CAG TCC TCT GTG AGC TGT GAC CAG              1645
Pro Ser His Asp Glu Gly Ala Arg Gln Ser Ser Val Ser Cys Asp Gln
    510                 515                 520

AGC AGC CAG ATC GTC TCC ATG ACC CTG AAC CCG GTC AAA AAG GAA GAT              1693
Ser Ser Gln Ile Val Ser Met Thr Leu Asn Pro Val Lys Lys Glu Asp
525                 530                 535                 540

GAA GGC TGG TAC TGG TGT GGG GTA AAA GAA GGT CAG GTC TAT GGA GAA              1741
Glu Gly Trp Tyr Trp Cys Gly Val Lys Glu Gly Gln Val Tyr Gly Glu
                545                 550                 555

ACT ACA GCC ATC TAT GTA GCA GTT GAA GAG AGG ACC AGA GGG TCA CCC              1789
Thr Thr Ala Ile Tyr Val Ala Val Glu Glu Arg Thr Arg Gly Ser Pro
            560                 565                 570

CAC ATC AAC CCG ACA GAT GCA AAC GCA CGT GCA AAA GAT GCT CCA GAG              1837
His Ile Asn Pro Thr Asp Ala Asn Ala Arg Ala Lys Asp Ala Pro Glu
        575                 580                 585

GAA GAG GCA ATG GAA TCC TCT GTC AGG GAG GAT GAA AAC AAG GCC AAT              1885
Glu Glu Ala Met Glu Ser Ser Val Arg Glu Asp Glu Asn Lys Ala Asn
    590                 595                 600

CTG GAC CCC AGG CTT TTT GCA GAC GAA AGA GAG ATA CAG AAT GCG GGA              1933
Leu Asp Pro Arg Leu Phe Ala Asp Glu Arg Glu Ile Gln Asn Ala Gly
605                 610                 615                 620

GAC CAA GCT CAG GAG AAC AGA GCA TCT GGG AAT GCT GGC AGT GCT GGT              1981
Asp Gln Ala Gln Glu Asn Arg Ala Ser Gly Asn Ala Gly Ser Ala Gly
                625                 630                 635

GGA CAA AGC GGG AGC TCC AAA GTC CTA TTC TCC ACC CTG GTG CCC CTG              2029
Gly Gln Ser Gly Ser Ser Lys Val Leu Phe Ser Thr Leu Val Pro Leu
            640                 645                 650

GGT TTG GTG CTG GCA GTG GGT GCT GTG GCT GTG TGG GTG GCC AGA GTC              2077
Gly Leu Val Leu Ala Val Gly Ala Val Ala Val Trp Val Ala Arg Val
        655                 660                 665

CGA CAT CGG AAG AAT GTA GAC CGC ATG TCA ATC AGC AGC TAC AGG ACA              2125
Arg His Arg Lys Asn Val Asp Arg Met Ser Ile Ser Ser Tyr Arg Thr
    670                 675                 680

GAC ATT AGC ATG GGA GAC TTC AGG AAC TCC AGG GAT TTG GGA GGC AAT              2173
Asp Ile Ser Met Gly Asp Phe Arg Asn Ser Arg Asp Leu Gly Gly Asn
685                 690                 695                 700

GAC AAC ATG GGC GCC ACT CCA GAC ACA CAA GAA ACA GTC CTC GAA GGA              2221
Asp Asn Met Gly Ala Thr Pro Asp Thr Gln Glu Thr Val Leu Glu Gly
                705                 710                 715

AAA GAT GAA ATA GAG ACT ACC ACC GAG TGT ACC ACC GAG CCA GAG GAA              2269
Lys Asp Glu Ile Glu Thr Thr Thr Glu Cys Thr Thr Glu Pro Glu Glu
            720                 725                 730

TCC AAG AAA GCA AAA AGG TCA TCC AAG GAG GAA GCT GAC ATG GCC TAC              2317
Ser Lys Lys Ala Lys Arg Ser Ser Lys Glu Glu Ala Asp Met Ala Tyr
        735                 740                 745

TCA GCA TTC CTG TTT CAG TCC AGC ACA ATA GCT GCG CAG GTC CAT GAT              2365
Ser Ala Phe Leu Phe Gln Ser Ser Thr Ile Ala Ala Gln Val His Asp
    750                 755                 760

GGT CCC CAG GAA GCC TAG GCAGTGCTGA CCACCTACCC CTGCCTGTGA CAATCAACT          2422
Gly Pro Gln Glu Ala
765

TGAGAATCAC ATTGATCCAC TCGCAGCCCA CCCTCGCCCA TCACCCAGGC TCTTCCCTCC            2482

TGTTCTCAGA GGTGTGCTGG TTCCTCCCTC AGTCGTGGAA GCCTGGCCTA CTTATGCCTG            2542

TTTAGGAGAG AGCGTGAGGA GTTCTTTTTG CTGTTAAAGA GTAAGGTGGA AATGAGTTGA            2602

GCCCAAGAGG TGTCTCTGAG AGACGAGGGT TCAGAGCAGG GGCTCATTTC AGGAGGAAGA            2662
```

-continued

```
GCCATTTGAA GCCTCTTTAT ACACATATGC TAGGATGTCA GGATAGCTCT TCTCCTCCAT    2722

CTCTCCTTTC TTCTCTTCTT GATTCAGACA ACAGATCCGA AAACTCACTA GGCTTCCGGT    2782

GTCTACTAAA TGCTGAGAGT CAGGCCACAG CCTTTCTATA ACATCACTG GAAGAGACAC     2842

CACCTCGTCC CAGATTCTGT CTTTTCCCTA AGCTATCAAT CATTACCGGG GATTCCCTTT    2902

GCCTCTGCAC CTCATAGGCA ACAAAAGAAA CATAAGTCCT GCAGTCTAAG CATACCCAA     2962

GCCATAAGGG CACCACGAGA CTCAGATGAG AAGAGATTTT TCTCCAGAGT ACTCAGTGAG    3022

ATAGACTAGT GTCAAGCCAG ATGGGGCAAC TCCTGGCTCT TGGCCTGGGA CTTGTCTTCA    3082

AGATCTCTGC TCTTATTAGA GAAAGAACTT TAGCATGAGG AAAAGTAAGA GAAAACAAGT    3142

TACATGGGCA TGGTGGTGTG CTCCTGCAAT CCCAATATTA AGAGGTTAAA AAATAGGACC    3202

AGAAGTTTAA AGTAATCCTT GGCTACCTAG TGAGTGTAAG GCCAGCCTGG AATCAATAAG    3262

AGTTGGT                                                              3269
```

(2) INFORMATION FOR SEQ ID NO: 10:

(i) SEQUENCE CHARACTERISTICS:
        (A) LENGTH: 769 amino acids
        (B) TYPE: amino acid
        (C) STRANDEDNESS: single
        (D) TOPOLOGY: linear
            DESCRIPTION:    Rat Polyimmunoglobulin Receptor (xi) SEQUENCE DESCRIPTION: SEQ ID NO: 10:

```
Met Arg Leu Ser Leu Phe Ala Leu Leu Val Thr Val Phe Ser Gly Val
 1               5                  10                  15

Ser Thr Gln Ser Pro Ile Phe Gly Pro Gln Asp Val Ser Ser Ile Glu
            20                  25                  30

Gly Asn Ser Val Ser Ile Thr Cys Tyr Tyr Pro Asp Thr Ser Val Asn
        35                  40                  45

Arg His Thr Arg Lys Tyr Trp Cys Arg Gln Gly Ala Asn Gly Tyr Cys
    50                  55                  60

Ala Thr Leu Ile Ser Ser Asn Gly Tyr Leu Ser Lys Glu Tyr Ser Gly
65                  70                  75                  80

Arg Ala Ser Leu Ile Asn Phe Pro Glu Asn Ser Thr Phe Val Ile Asn
                85                  90                  95

Ile Ala His Leu Thr Gln Glu Asp Thr Gly Ser Tyr Lys Cys Gly Leu
            100                 105                 110

Gly Thr Thr Asn Arg Gly Leu Phe Phe Asp Val Ser Leu Glu Val Ser
        115                 120                 125

Gln Val Pro Glu Phe Pro Asn Asp Thr His Val Tyr Thr Lys Asp Ile
    130                 135                 140

Gly Arg Thr Val Thr Ile Glu Cys Arg Phe Lys Glu Gly Asn Ala His
145                 150                 155                 160

Ser Lys Lys Ser Leu Cys Lys Lys Arg Gly Glu Ala Cys Glu Val Val
                165                 170                 175

Ile Asp Ser Thr Glu Tyr Val Asp Pro Ser Tyr Lys Asp Arg Ala Ile
            180                 185                 190

Leu Phe Met Lys Gly Thr Ser Arg Asp Ile Phe Tyr Val Asn Ile Ser
        195                 200                 205

His Leu Ile Pro Ser Asp Ala Gly Leu Tyr Val Cys Gln Ala Gly Glu
    210                 215                 220

Gly Pro Ser Ala Asp Lys Asn Asn Ala Asp Leu Gln Val Leu Glu Pro
225                 230                 235                 240
```

```
Glu Pro Glu Leu Leu Tyr Lys Asp Leu Arg Ser Ser Val Thr Phe Glu
            245                 250                 255

Cys Asp Leu Gly Arg Glu Val Ala Asn Asp Ala Lys Tyr Leu Cys Arg
            260                 265                 270

Lys Asn Lys Glu Thr Cys Asp Val Ile Ile Asn Thr Leu Gly Lys Arg
            275                 280                 285

Asp Pro Ala Phe Glu Gly Arg Ile Leu Leu Thr Pro Arg Asp Asp Asn
290                     295                 300

Gly Arg Phe Ser Val Leu Ile Thr Gly Leu Arg Lys Glu Asp Ala Gly
305                 310                 315                 320

His Tyr Gln Cys Gly Ala His Ser Ser Gly Leu Pro Gln Glu Gly Trp
                325                 330                 335

Pro Val Gln Ala Trp Gln Leu Phe Val Asn Glu Glu Ser Thr Ile Pro
            340                 345                 350

Asn Ser Arg Ser Val Val Lys Gly Val Thr Gly Gly Ser Val Ala Ile
            355                 360                 365

Val Cys Pro Tyr Asn Pro Lys Glu Ser Ser Ser Leu Lys Tyr Trp Cys
    370                 375                 380

His Trp Glu Ala Asp Glu Asn Gly Arg Cys Pro Val Leu Val Gly Thr
385                 390                 395                 400

Gln Ala Leu Val Gln Glu Gly Tyr Glu Gly Arg Leu Ala Leu Phe Asp
                405                 410                 415

Gln Pro Gly Ser Gly Ala Tyr Thr Val Ile Leu Asn Gln Leu Thr Thr
            420                 425                 430

Gln Asp Ser Gly Phe Tyr Trp Cys Leu Thr Asp Gly Asp Ser Arg Trp
            435                 440                 445

Arg Thr Thr Ile Glu Leu Gln Val Ala Glu Ala Thr Lys Lys Pro Asp
            450                 455                 460

Leu Glu Val Thr Pro Gln Asn Ala Thr Ala Val Ile Gly Glu Thr Phe
465                 470                 475                 480

Thr Ile Ser Cys His Tyr Pro Cys Lys Phe Tyr Ser Gln Glu Lys Tyr
                485                 490                 495

Trp Cys Lys Trp Ser Asn Asp Gly Cys His Ile Leu Pro Ser His Asp
            500                 505                 510

Glu Gly Ala Arg Gln Ser Ser Val Ser Cys Asp Gln Ser Ser Gln Ile
            515                 520                 525

Val Ser Met Thr Leu Asn Pro Val Lys Lys Glu Asp Glu Gly Trp Tyr
    530                 535                 540

Trp Cys Gly Val Lys Glu Gly Gln Val Tyr Gly Glu Thr Thr Ala Ile
545                 550                 555                 560

Tyr Val Ala Val Glu Glu Arg Thr Arg Gly Ser Pro His Ile Asn Pro
                565                 570                 575

Thr Asp Ala Asn Ala Arg Ala Lys Asp Ala Pro Glu Glu Ala Met
            580                 585                 590

Glu Ser Ser Val Arg Glu Asp Glu Asn Lys Ala Asn Leu Asp Pro Arg
            595                 600                 605

Leu Phe Ala Asp Glu Arg Glu Ile Gln Asn Ala Gly Asp Gln Ala Gln
            610                 615                 620

Glu Asn Arg Ala Ser Gly Asn Ala Gly Ser Ala Gly Gln Ser Gly
625                 630                 635                 640

Ser Ser Lys Val Leu Phe Ser Thr Leu Val Pro Leu Gly Leu Val Leu
            645                 650                 655

Ala Val Gly Ala Val Ala Val Trp Val Ala Arg Val Arg His Arg Lys
```

```
                    660               665               670
Asn Val Asp Arg Met Ser Ile Ser Ser Tyr Arg Thr Asp Ile Ser Met
            675               680               685
Gly Asp Phe Arg Asn Ser Arg Asp Leu Gly Gly Asn Asp Asn Met Gly
            690               695               700
Ala Thr Pro Asp Thr Gln Glu Thr Val Leu Glu Gly Lys Asp Glu Ile
705               710               715               720
Glu Thr Thr Thr Glu Cys Thr Thr Glu Pro Glu Glu Ser Lys Lys Ala
                    725               730               735
Lys Arg Ser Ser Lys Glu Glu Ala Asp Met Ala Tyr Ser Ala Phe Leu
                    740               745               750
Phe Gln Ser Ser Thr Ile Ala Ala Gln Val His Asp Gly Pro Gln Glu
            755               760               765
Ala
```

(2) INFORMATION FOR SEQ ID NO: 11:

(i) SEQUENCE CHARACTERISTICS:
        (A) LENGTH: 322 base pairs
        (B) TYPE: nucleic acid
        (C) STRANDEDNESS: single
        (D) TOPOLOGY: linear
            DESCRIPTION: Guy's 13 Kappa (ix) FEATURE:
        (A) NAME/KEY: Coding Sequence
        (B) LOCATION: 8....320

(xi) SEQUENCE DESCRIPTION: SEQ ID NO: 11:

```
CTCGAGC GAC ATT GTG ATG ACC CAG TCT CCA GCA ATC ATG TCT GCA TCT        49
        Asp Ile Val Met Thr Gln Ser Pro Ala Ile Met Ser Ala Ser
          1               5                  10
CCA GGG GAG AAG GTC ACC ATA ACC TGC AGT GCC AGC TCA AGT GTA AGT        97
Pro Gly Glu Lys Val Thr Ile Thr Cys Ser Ala Ser Ser Ser Val Ser
15              20                  25                  30
TAC ATG CAC TGG TTC CAG CAG AAG CCA GGC ACT TCT CCC AAA CTC TGG       145
Tyr Met His Trp Phe Gln Gln Lys Pro Gly Thr Ser Pro Lys Leu Trp
                35                  40                  45
CTT TAT AGC ACA TCC AAC CTG GCT TCT GGA GTC CCT GCT CGC TTC AGT       193
Leu Tyr Ser Thr Ser Asn Leu Ala Ser Gly Val Pro Ala Arg Phe Ser
            50                  55                  60
GGC AGT GGA TCT GGG ACC TCT TAC TCT CTC ACA ATC AGC CGA ATG GAG       241
Gly Ser Gly Ser Gly Thr Ser Tyr Ser Leu Thr Ile Ser Arg Met Glu
        65                  70                  75
GCT GAA GAT GCT GCC ACT TAT TAC TGC CAT CAA AGG ACT AGT TAC CCG       289
Ala Glu Asp Ala Ala Thr Tyr Tyr Cys His Gln Arg Thr Ser Tyr Pro
    80                  85                  90
TAC ACG TTC GGA GGG GGG ACC AAG CTG GAA A TA                          322
Tyr Thr Phe Gly Gly Gly Thr Lys Leu Glu Ile
95                  100                 105
```

(2) INFORMATION FOR SEQ ID NO: 12:

(i) SEQUENCE CHARACTERISTICS:
        (A) LENGTH: 105 amino acids
        (B) TYPE: amino acid
        (C) STRANDEDNESS: single
        (D) TOPOLOGY: linear
            DESCRIPTION: Guy's 13 Kappa (xi) SEQUENCE DESCRIPTION: SEQ ID NO: 12:

Asp Ile Val Met Thr Gln Ser Pro Ala Ile Met Ser Ala Ser Pro Gly

```
  1               5                   10                  15
Glu Lys Val Thr Ile Thr Cys Ser Ala Ser Ser Val Ser Tyr Met
             20                  25                  30

His Trp Phe Gln Gln Lys Pro Gly Thr Ser Pro Lys Leu Trp Leu Tyr
             35                  40                  45

Ser Thr Ser Asn Leu Ala Ser Gly Val Pro Ala Arg Phe Ser Gly Ser
             50                  55                  60

Gly Ser Gly Thr Ser Tyr Ser Leu Thr Ile Ser Arg Met Glu Ala Glu
65                   70                  75                  80

Asp Ala Ala Thr Tyr Tyr Cys His Gln Arg Thr Ser Tyr Pro Tyr Thr
                 85                  90                  95

Phe Gly Gly Gly Thr Lys Leu Glu Ile
                100                 105
```

(2) INFORMATION FOR SEQ ID NO: 13:

(i) SEQUENCE CHARACTERISTICS:
        (A) LENGTH: 402 base pairs
        (B) TYPE: nucleic acid
        (C) STRANDEDNESS: single
        (D) TOPOLOGY: linear
            DESCRIPTION:    Guy's 13 Gamma 1

(ix) FEATURE:
        (A) NAME/KEY: Coding Sequence
        (B) LOCATION: 7...402

(xi) SEQUENCE DESCRIPTION: SEQ ID NO: 13:

```
CTCGAG ATG GAA TGG ACC TGG GTT TTT CTC TTC CTC CTG TCA GGA ACT       48
       Met Glu Trp Thr Trp Val Phe Leu Phe Leu Leu Ser Gly Thr
        1               5                  10

GCA GGC GTC CAC TCT GGG GTC CAG CTT CAG CAG TCA GGA CCT GAC CTG      96
Ala Gly Val His Ser Gly Val Gln Leu Gln Gln Ser Gly Pro Asp Leu
15              20                  25                  30

GTG AAA CCT GGG GCC TCA GTG AAG ATA TCC TGC AAG GCT TCT GGA TAC     144
Val Lys Pro Gly Ala Ser Val Lys Ile Ser Cys Lys Ala Ser Gly Tyr
                35                  40                  45

ACA TTC ACT GAC TAC AAC ATA CAC TGG GTG AAG CAG AGC CGT GGA AAG     192
Thr Phe Thr Asp Tyr Asn Ile His Trp Val Lys Gln Ser Arg Gly Lys
                50                  55                  60

AGC CTT GAG TGG ATT GGA TAT ATT TAT CCT TAC AAT GGT AAT ACT TAC     240
Ser Leu Glu Trp Ile Gly Tyr Ile Tyr Pro Tyr Asn Gly Asn Thr Tyr
65                  70                  75

TAC AAC CAG AAG TTC AAG AAC AAG GCC ACA TTG ACT GTA GAC AAT TCC     288
Tyr Asn Gln Lys Phe Lys Asn Lys Ala Thr Leu Thr Val Asp Asn Ser
        80                  85                  90

TCC ACC TCA GCC TAC ATG GAG CTC CGC AGC CTG ACA TCT GAG GAC TCT     336
Ser Thr Ser Ala Tyr Met Glu Leu Arg Ser Leu Thr Ser Glu Asp Ser
95                  100                 105                 110

GCA GTC TAT TAC TGT GCA ACC TAC TTT GAC TAC TGG GGC CAA GGC ACC     384
Ala Val Tyr Tyr Cys Ala Thr Tyr Phe Asp Tyr Trp Gly Gln Gly Thr
                115                 120                 125

ACT CTC ACA GTC TCC TCA                                             402
Thr Leu Thr Val Ser Ser
                130
```

(2) INFORMATION FOR SEQ ID NO: 14:

(i) SEQUENCE CHARACTERISTICS:
        (A) LENGTH: 132 amino acids
        (B) TYPE: amino acid
        (C) STRANDEDNESS: single

```
         (D) TOPOLOGY: linear
            DESCRIPTION:    Guy's 13 Gamma 1

(xi) SEQUENCE DESCRIPTION: SEQ ID NO: 14:

Met Glu Trp Thr Trp Val Phe Leu Phe Leu Leu Ser Gly Thr Ala Gly
 1               5                  10                  15

Val His Ser Gly Val Gln Leu Gln Gln Ser Gly Pro Asp Leu Val Lys
                20                  25                  30

Pro Gly Ala Ser Val Lys Ile Ser Cys Lys Ala Ser Gly Tyr Thr Phe
            35                  40                  45

Thr Asp Tyr Asn Ile His Trp Val Lys Gln Ser Arg Gly Lys Ser Leu
    50                  55                  60

Glu Trp Ile Gly Tyr Ile Tyr Pro Tyr Asn Gly Asn Thr Tyr Tyr Asn
65                  70                  75                  80

Gln Lys Phe Lys Asn Lys Ala Thr Leu Thr Val Asp Asn Ser Ser Thr
                85                  90                  95

Ser Ala Tyr Met Glu Leu Arg Ser Leu Thr Ser Glu Asp Ser Ala Val
            100                 105                 110

Tyr Tyr Cys Ala Thr Tyr Phe Asp Tyr Trp Gly Gln Gly Thr Thr Leu
        115                 120                 125

Thr Val Ser Ser
    130

(2) INFORMATION FOR SEQ ID NO: 15:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 15:

ACCAGATCTA TGGAATGGAC CTGGGTTTTT C                                 31

(2) INFORMATION FOR SEQ ID NO: 16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 16:

CCCAAGCTTG GTTTTGGAGA TGGTTTTCTC                                   30

(2) INFORMATION FOR SEQ ID NO: 17:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 17:

GATAAGCTTG GTCCTACTCC TCCTCCTCCT A                                 31

(2) INFORMATION FOR SEQ ID NO: 18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear
```

```
    (xi) SEQUENCE DESCRIPTION: SEQ ID NO: 18:

AATCTCGAGT CAGTAGCAGA TGCCATCTCC                                              30

(2) INFORMATION FOR SEQ ID NO: 19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 19:

GGAAAGCTTT GTACATATGC AAGGCTTACA                                              30
```